US009598693B2

(12) United States Patent
Esau et al.

(10) Patent No.: US 9,598,693 B2
(45) Date of Patent: Mar. 21, 2017

(54) OLIGOMERIC COMPOUNDS AND COMPOSITIONS FOR THE USE IN MODULATION OF MICRORNAS

(71) Applicant: Ionis Pharmaceuticals, Inc., Carlsbad, CA (US)

(72) Inventors: Christine Esau, La Jolla, CA (US); Eric E. Swayze, Encinitas, CA (US); Balkrishen Bhat, Carlsbad, CA (US); Garth A. Kinberger, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/809,527

(22) Filed: Jul. 27, 2015

(65) Prior Publication Data

US 2015/0322436 A1   Nov. 12, 2015

Related U.S. Application Data

(63) Continuation of application No. 13/353,114, filed on Jan. 18, 2012, now Pat. No. 9,127,272, which is a continuation of application No. 12/161,286, filed as application No. PCT/US2007/061186 on Jan. 27, 2007, now Pat. No. 8,129,515.

(60) Provisional application No. 60/762,721, filed on Jan. 27, 2006, provisional application No. 60/805,204, filed on Jun. 19, 2006.

(51) Int. Cl.
   *C12N 15/113* (2010.01)
   *C12N 15/11* (2006.01)

(52) U.S. Cl.
   CPC .......... *C12N 15/111* (2013.01); *C12N 15/113* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/341* (2013.01); *C12N 2310/346* (2013.01); *C12N 2320/51* (2013.01)

(58) Field of Classification Search
   None
   See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,845,205 A | 7/1989 | Huynh et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,393,878 A | 2/1995 | Leumann |
| 5,399,676 A | 3/1995 | Froehler |
| 5,403,711 A | 4/1995 | Walder et al. |

(Continued)

FOREIGN PATENT DOCUMENTS

| | | |
|---|---|---|
| WO | WO 92/03568 | 3/1992 |
| WO | WO 93/07883 | 4/1993 |

(Continued)

OTHER PUBLICATIONS

Altman et al., "Second Generation of Antisense Oligonucleotides: From Nuclease Resistance to Biological Efficacy in Animals" Chimia (1996) 50:168-176.
Altmann et al., "Second-generation antisense oligonucleotides: structure-activity relationships and the design of improved signal-transduction inhibitors" Biochem. Soc. Trans. (1996) 24:630-637.
Altmann et al., "Second Generation Antisense Oligonucleotides— Inhibition of PKC-a and c-RAF Kinase Expression by Chimeric Oligonucleotides Incorporating 6'-Substituted Carbocyclic Nucleosides and 2'-Ethylene Glycol Substitued Ribonucleosides" Nucleosides Nucleotides (1997) 16(7-9):917-926.
Alvarez-Gacria et al., "MicroRNA functions in animal development and human disease" Development (2005) 132:4653-4662.
Arnott et al., "Optimised Parameters for A-DNA and B-DNA" Biochem. Biophys. Res. Comm. (1972) 47(6):1504.

(Continued)

*Primary Examiner* — Tracy Vivlemore
(74) *Attorney, Agent, or Firm* — Ionis Pharmaceuticals, Inc. Patent Dept.

(57) ABSTRACT

Compounds, compositions and methods are provided for modulating the levels expression, processing and function of miRNAs. The compositions comprise oligomeric compounds targeted to small non-coding RNAs and miRNAs. The oligomeric compounds possess potent miRNA inhibitory activity, and further exhibit improved therapeutic index. Further provided are methods for selectively modulating miRNA activating in a cell.

15 Claims, No Drawings

(56) References Cited

U.S. PATENT DOCUMENTS

| | | |
|---|---|---|
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,614,621 A | 3/1997 | Ravikumar et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,760,209 A | 6/1998 | Cheruvallath et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,007,992 A | 12/1999 | Lin et al. |
| 6,020,475 A | 2/2000 | Capaldi et al. |
| 6,028,183 A | 2/2000 | Lin et al. |
| 6,051,699 A | 4/2000 | Ravikumar |
| 6,121,437 A | 9/2000 | Guzaev et al. |
| 6,147,200 A | 11/2000 | Manoharan et al. |
| 6,169,177 B1 | 1/2001 | Manoharan |
| 6,172,209 B1 | 1/2001 | Manoharan et al. |
| 6,268,490 B1 | 7/2001 | Imanishi et al. |
| 6,326,478 B1 | 12/2001 | Cheruvallath et al. |
| 6,465,628 B1 | 10/2002 | Ravikumar et al. |
| 6,670,461 B1 | 12/2003 | Wengel et al. |
| 2002/0147332 A1 | 10/2002 | Kaneko et al. |
| 2003/0082807 A1 | 5/2003 | Wengel |
| 2003/0087230 A1 | 5/2003 | Wengel |
| 2003/0158403 A1 | 8/2003 | Manoharan et al. |
| 2003/0175906 A1 | 9/2003 | Manoharan et al. |
| 2003/0207804 A1 | 11/2003 | Manoharan et al. |
| 2003/0207841 A1 | 11/2003 | Kaneko et al. |
| 2004/0180351 A1* | 9/2004 | Giese .................. C12N 15/113 435/6.11 |
| 2005/0059005 A1 | 3/2005 | Tuschl et al. |
| 2005/0182005 A1 | 8/2005 | Tuschl et al. |
| 2005/0221293 A1 | 10/2005 | Tuschl et al. |
| 2005/0222399 A1 | 10/2005 | Bentwich |
| 2005/0227934 A1 | 10/2005 | Stoffel et al. |

FOREIGN PATENT DOCUMENTS

| | | |
|---|---|---|
| WO | WO 94/01550 | 1/1994 |
| WO | WO 97/26270 | 7/1997 |
| WO | WO 98/39352 | 9/1998 |
| WO | WO 99/14226 | 3/1999 |
| WO | WO 01/25248 | 4/2001 |
| WO | WO 03/004602 | 1/2003 |
| WO | WO 03/029459 | 4/2003 |
| WO | WO 2004/044138 | 5/2004 |
| WO | WO 2005/013901 | 2/2005 |
| WO | WO 2005/121370 | 12/2005 |
| WO | WO 2007/021896 | 2/2007 |
| WO | WO 2008/094945 | 8/2008 |

OTHER PUBLICATIONS

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Beaucage et al., "The Functionalization of Oligonucleotides via Phosphoramidite Derivatives" Tetrahedron (1993) 49(10):1925-1963.

Berger et al., "Crystal structures of B-DNA with incorporated 2'-deoxy-2'-fluoro-arabino-furanosyl thymines: implications of conformational preorganization for duplex stability" Nucleic Acids Research (1998) 26(10):2473-2480.

Brazma et al., "Gene expression data analysis" FEBS Letters (2000) 480:17-24.

Calin et al., "Frequent deletions and down-regulation of micro-RNA genes miR15 and miR16 at 13q14 in chronic lymphocytic leukemia" PNAS (2002) 99:15524-15529.

Calin et al., "Human microRNA genes are frequently located at fragile sites and genomic regions involved in cancers" PNAS (2004) 101:2999-3004.

Calin et al., "MicronRNA profiling reveals distinct signatures in B cell chronic lymphocytic leukemias" PNAS (2004) 101:11755-11760.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

(56) References Cited

OTHER PUBLICATIONS

Conte et al., "Conformational properties and thermodynamics of the RNA duplex r(CGCAAAUUUGCG)2: comparison with the DNA analogue of d(CGCAAATTGCG)2" Nucleic Acids Res. (1997) 25(13):2627-2634.

Crooke et al., "Kinetic Characteristics of *Escherichia coli* RNase H1: Cleavage of Various Antisense Oligonucleotide-RNA Duplexes" Biochemical Journal (1995) 312(2):599-608.

Davies et al., "Improved targeting of miRNA with antisense oligonucleotides" Nucleic Acids Research (2006) 34(8):2294-2304.

Egli et al., "RNA Hydration: A Detailed Look" Biochemistry (1996) 35:8489-8494.

Esau et al., "miR-122 regulation of lipid metabolism revealed by in vivo antisense targeting" Cell Metabolism (2006) 3(2):87-98.

Fedoroff et al., "Structure of a DNA:RNA Hybrid Duplex: Why RNase H Does Not Cleave Pure RNA" J. Mol. Biol. (1993) 233:509-523.

Flanagan et al., "A cytosine analog that confers enhanced potency to antisense oligonucleotides" PNAS (1999) 96:3513-3518.

Freier et al., "The ups and downs of nucleic acid duplex stability: structure-stability studies on chemically-modified DNA:RNA duplexes" Nucleic Acids Research (1997) 25(22):4429-4443.

Fuchs et al., "Identification of Differentially Expressed Genes by Mutually Subtracted RNA Fingerprinting" Anal. Biochem. (2000) 286:91-98.

Gait et al., Applications of Chemically Synthesized RNA in RNA: Protein Interactions, 1998, pp. 1-36.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Going et al., "Molecular Pathology and Future Developments" Eur. J. Cancer (1999) 35:1895-1904.

Gonzalez et al., "Structure and Dynamics of a DNA-RNA Hybrid Duplex with a Chiral Phosphorothioate Moiety: NMR and Molecular Dynamics with Conventional and Time-Averaged Restraints" Biochemistry (1995) 34:4969-4982.

Guillerm et al., "Synthesis of 4'-Fluoroadenosine as an Inhibitor of 2-Adenosyl-L-Homocysteine Hydrolase" Bioorganic and Medicinal Chemistry Letters (1995) 5:1455-1460.

Harry-O'Kura et al., "A Short, Flexible Route toward 2'-C-Branched Ribonucleosides" J. Org. Chem. (1997) 62(6):1754-1759.

He et al., "A microRNA polycistron as a potential human oncogene" Nature (2005) 435:828-833.

Horton et al., "The Structure of an RNA/DNA Hybrid: A Substrate of the Ribonuclease Activity of HIV-1 Reverse Transcriptase" J. Mol. Biol. (1996) 264:521-533.

Jacobson et al., "Methanocarba Analogues of Purine Nucleosides as Potent and Selective Adenosine Receptor Agonists" J. Med. Chem. Lett. (2000) 43:2196-2203.

Jurecic et al., "Long-distance DD-PCR and cDNA microarrays" Curr. Opin. Microbiol. (2000) 3:316-321.

Kawasaki et al., "Uniformly modified 2'-deoxy-2'-fluorophosphorothioate oligonucleotides as nuclease-resistant antisense compounds with high affinity and specificity for RNA targets" J. Med. Chem. (1993) 36:831-841.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Kurchavov et al., "A New Phosphoramidite Reagent for the Incorporation of Diazaphenoxazinone Nucleoside with Enhanced Base-Pairing Properties into Oligodeoxynucleotides" Nucleosides & Nucleotides (1997) 16(10&11):1837-1846.

Lane et al., "NMR assignments and solution conformation of the DNA-RNA hybrid duplex d(GTGAACTT)-r(AAGUUCAC)" Eur. J. Biochem. (1993) 215:297-306.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" S. Biotech. (2000) 80:143-157.

Lee et al., "Ring-Constrained (N)-Methanocarba Nucleosides as Adenosine Receptor Agonists: Independent 5'-Uronamide and 2'-Deoxy Modifications" Bioorganic & Medicinal Chemistry Letters (2001) 11:1333-1337.

Lee et al., "MicroRNA maturation: stepwise processing and subcellular localization" Embo J. (2002) 21(17):4663-4670.

Lesnik et al., "Relative Thermodynamic Stability of DNA, RNA, and DNA:RNA Hybrid Duplexes: Relationships with Base Composition and Structure" Biochemistry (1995) 34:10807-10815.

Lewis et al., "Conserved Seed Pairing, Often Flanked by Adenosines, Indicates that Thousands of Human Genes are MicroRNA Targets" Cell (2005) 120:15-20.

Lin et al., "Tricyclic 2'-Deoxycytidine Analogs: Syntheses and Incorporation into Oligodeoxynucleotides Which Have Enhanced Binding to Complementary RNA" J. Am. Chem. Soc. (1995) 117:3873-3874.

Lin et al., "A Cytosine Analogue Capable of Clamp-Like Binding to a Guanine in Helical Nucleic Acids" J. Am. Chem. Soc. (1998) 120:8531-8532.

Lok et al., "Potent Gene-Specific Inhibitory Properties of Mixed-Backbone Antisense Oligonucleotides Comprised of 2'-Deoxy-2'-fluoro-D-arabinose and 2'-Deoxyribose Nucleotides" Biochemistry (2002) 41:3457-3467.

Lu et al., "MicroRNA expression profiles classify human cancers" Nature (2005) 435:834.

Madden et al., "Serial analysis of gene expression: from gene discovery to target identification" DDT (2000) 5:415-425.

Martin, "Ein neuer Zugang zu 2'-O-Alkylribonucleosiden and Eigenschaften deren Oligonucleotide" Helv. Chim. Acta. (1995) 78:486-504.

Mcmanus, "MicroRNAs and caner" Seminars in Cancer Biology (2003) 13:252-258.

Owen et al., "4'-Substituted Nucleosides. 3. Synthesis of Some 4'-Fluorouridine Derivatives" J. Org. Chem. (1976) 41(18):3010-3017.

Pillai, "MicroRNA function: Mulitple mechanisms for a tiny RNA?" RNA (2005) 11:1753-1761.

Prashar et al., "Reads: A Method for Display of 3'-End Fragment of Restriction Enzyme-Digested cDNAs for Analysis of Differential Gene Expression" Methods Enzymol. (1999) 303:258-272.

Saenger et al., Principles of Nucleic Acid Structure, 1984, Springer-Verlag; New York, NY.

Sanghvi, Antisense Research and Applications, Chapter 15, Crooke & Lebleu ed., CRC Press, 1993.

Scaringe, "RNA Oligonucleotide Synthesis via 5'-Sily1-2'-Orthoester Chemistry" Methods (2001) 23:206-217.

Searle et al., "On the stability of nucleic acid structures in solution: enthalpy-entropy compensations, internal rotations and reversibility" Nucleic Acids Res. (1993) 21(9):2051-2056.

Singh et al., "LNA (locked nucleic acids): synthesis and high-affinity nucleic acid recognition" Chem. Commun. (1998) 4:455-456.

Sutcliffe et al., "TOGA: An automated parsing technology for analyzing expression of nearly all genes" PNAS (2000) 97:1976-1981.

Tang et al., "2'-C-Branched Ribonucleosides: Synthesis of the Phosphoramidite Derivatives of 2'-C-Beta-Methylcytidine and Their Incorporation into Oligonucleotides" J. Org. Chem. (1999) 64:747-754.

To, "Identification of Differential Gene Expression by High Throughput Analysis" Comb. Chem. High Throughput Screen (2000) 3:235-241.

Wang et al., "Synthesis and binding property of an oligonucleotide containing tetrafluorophenoxazine" Tetrahedron Lett. (1998) 39:8385-8388.

(56) References Cited

OTHER PUBLICATIONS

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122:8595-8602.

International Search Report for application PCT/US2007/061186 dated Jul. 23, 2007.

* cited by examiner

US 9,598,693 B2

OLIGOMERIC COMPOUNDS AND COMPOSITIONS FOR THE USE IN MODULATION OF MICRORNAS

SEQUENCE LISTING

The present application is being filed along with a Sequence Listing in electronic format. The Sequence Listing is provided as a file entitled CORE0066USC2SEQ_ST25.txt, created on Jul. 13, 2015, which is 96 Kb in size. The information in the electronic format of the sequence listing is incorporated herein by reference in its entirety.

FIELD OF THE INVENTION

The present invention provides compositions and methods for modulation of small non-coding RNAs, including microRNA. In particular, this invention relates to oligomeric compounds, particularly chemically modified oligonucleotides, which, in some embodiments, hybridize with or sterically interfere with nucleic acid molecules comprising or encoding small non-coding RNA targets, including microRNAs.

BACKGROUND OF THE INVENTION

MicroRNAs (miRNAs), also known as "mature" miRNA" are small (approximately 21-24 nucleotides in length), non-coding RNA molecules encoded in the genomes of plants and animals. These highly conserved, endogenously expressed RNAs regulate the expression of genes by binding to the 3'-untranslated regions (3'-UTR) of specific mRNAs. More than 500 different miRNAs have been identified in plants and animals. Mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670).

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662).

Links between miRNAs, including miRNA families and clusters, and human disease have been also been identified. Many miRNAs are de-regulated in primary human tumors (Calin et al., Proc. Natl. Acad. Sci, 2002, 99, 15524-15529; Calin et al., Proc. Natl. Acad. Sci, 2004, 101, 11755-11760; He et al., Nature, 2005, 435, 828-833; Lu et al., Nature, 2005, 435, 834). Moreover, many human miRNAs are located at genomic regions linked to cancer (Calin et al., Proc. Natl. Acad. Sci, 2004, 101, 2999-3004; McManus, 2003, Semin. Cancer Biol, 13, 252-258; He et al., Nature, 2005, 435, 828-833). Mir-15a and miR-16-1, which are derived from a polycistronic miRNA, are located within a 30-kb region of chromosome 13q14, a region deleted in more than half of B cell chronic lymphocytic leukemias (B-CLL). Both miR-15a and miR-16-1 are deleted or down-regulated in the majority of CLL cases (Calin et al., Proc. Nat. Acad. Sci, 2002, 99, 15524-15529).

Families of miRNAs can be characterized by nucleotide identity at positions 2-8 of the miRNA, a region known as the seed sequence. Lewis et al. describe several miRNA families, as well as miRNA superfamilies, which are characterized by related seed sequences (Lewis et al. 2005).

MiRNAs are thought to exercise post-transcriptional control in most eukaryotic organisms and have been detected in plants and animals as well as certain viruses. A large number of miRNAs have been identified from several species (see for example PCT Publication WO 03/029459 and Published US Patent Applications 20050222399, 20050227934, 20050059005 and 20050221293, each of which are incorporated herein by reference in their entirety) and many more have been bioinformatically predicted. Many of these miRNA are conserved across species, but species specific miRNA have also been identified (Pillai, RNA, 2005, 11, 1753-1761).

There is a need for agents that regulate gene expression via the mechanisms mediated by small non-coding RNAs. The present invention meets this and other needs.

SUMMARY OF THE INVENTION

The present invention provides, inter alia, chemically modified oligomeric compounds and methods useful for modulating the levels, activity, or function of miRNAs, including those relying on antisense and non-antisense mechanisms.

The present invention provides, inter alia, oligomeric compounds, particularly nucleic acid and nucleic acid-like oligomeric compounds, which are targeted to nucleic acids comprising or encoding small non-coding RNAs, and which act to modulate the levels of small non-coding RNAs, or interfere with their function.

The present invention also provides oligomeric compounds, preferably nucleic acid and nucleic acid-like oligomeric compounds, which are targeted to miRNAs, and which act to modulate the levels of miRNAs, or interfere with their processing or function.

The present invention provides oligomeric compounds comprising a contiguous sequence of about 17 to about 29 nucleosides linked by internucleoside linking groups, said sequence having an internal region located between two external regions, each external region independently comprises from 1 to about 3 nucleosides, each external region comprises a stabilizing nucleoside, the internal region comprises at least 10 β-D-2'-deoxy-2'-fluororibofuranosyl nucleosides, and each of the stabilizing nucleosides provides enhanced nuclease stability relative to a β-D-2'-deoxy-2'-fluororibofuranosyl nucleoside.

The present invention further provides oligomeric compounds comprising a contiguous sequence of about 17 to about 29 nucleosides linked by internucleoside linking groups, said sequence having an internal region located between two external regions, each external region independently comprises from 1 to about 3 nucleosides, each external region comprises a stabilizing modification, and the internal region comprises at least 10 β-D-2'-deoxy-2'-fluororibofuranosyl nucleosides.

In certain embodiments, the oligomeric compounds comprise a contiguous sequence of linked nucleosides defines a gapped oligomeric compound comprising only β-D-2'-deoxy-2'-fluororibofuranosyl nucleosides in the internal region. In other embodiments, the oligomeric compounds comprise a contiguous sequence of linked nucleosides can also define a positionally modified oligomeric compound comprising from 2 to 6 stabilizing nucleosides in the internal region.

In some embodiments, the stabilizing modification comprises a stabilizing nucleoside, a stabilizing internucleoside linkage group, or a combination thereof. In further embodiments, each stabilizing nucleoside provides enhanced nuclease stability relative to a β-D-2'-deoxyribofuranosyl nucleoside.

In some embodiments, each nucleoside in the internal region is, independently, a stabilizing nucleoside or a β-D-2'-deoxy-2'-fluororibofuranosyl nucleoside wherein at least one β-D-2'-deoxy-2'-fluororibofuranosyl nucleoside separates each stabilizing nucleoside in the internal region from each external region.

In certain embodiments, each stabilizing nucleoside is, independently, a 2'-modified nucleoside.

In one embodiment, the 2'-modified nucleoside is a bicyclic sugar modified nucleoside. In other embodiments, each bicyclic sugar modified nucleoside independently comprises a D or L sugar in the alpha or beta configuration.

In some embodiments, each of the 2'-modified nucleosides independently comprises a 2'-substituent group selected from O—$C_1$-$C_{12}$ alkyl, substituted O—$C_1$-$C_{12}$ alkyl, O—$C_2$-$C_{12}$ alkenyl, substituted O—$C_2$-$C_{12}$ alkenyl, O—$C_2$-$C_{12}$ alkynyl, substituted O—$C_2$-$C_{12}$ alkynyl, amino, substituted amino, amide, substituted amide, aralkyl, substituted aralkyl, O-aralkyl, substituted O-aralkyl, $N_3$, SH, CN, OCN, $CF_3$, $OCF_3$, $SOCH_3$, —$SO_2CH_3$, heterocycloalkyl, heterocycloalkaryl, aminoalkylamino and polyalkylamino; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, O—$C_1$-$C_{12}$ alkyl, substituted O—$C_1$-$C_{12}$ alkyl, S—$C_1$-$C_{12}$ alkyl, substituted S—$C_1$-$C_{12}$ alkyl, acyl(C(=O)—H), substituted acyl, amino, substituted amino, amide, substituted amide, $C_1$-$C_{12}$ alkylamino, substituted $C_1$-$C_{12}$ alkylamino, $C_1$-$C_{12}$ aminoalkoxy, substituted $C_1$-$C_{12}$ aminoalkoxy, $C_1$-$C_{12}$ alkylaminooxy, substituted $C_1$-$C_{12}$ alkylaminooxy, guanidinyl, substituted guanidinyl or a protecting group.

In other embodiments, the 2'-modified nucleosides independently comprise a 2'-substituent group selected from $O(CH_2)_{0-2}CH_3$, $O(CH_2)_2OCH_3$, $O(CH_2)_2SCH_3$, $OCH_2C(H)CH_2$, $O(CH_2)_2ON(CH_3)_2$ and $OCH_2C(=O)N(H)CH_3$.

In certain embodiments, each of the bicyclic sugar modified nucleosides independently comprises a bridge group between the 2' and the 4'-carbon atoms comprising from 1 to 8 linked biradical groups independently selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)$_2$—, —S(=O)—, —C(=O)— and —C(=S)—;

each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, each stabilizing internucleoside linkage group is a phosphorothioate internucleoside linkage group.

The present invention provides oligomeric compounds having a contiguous sequence of linked nucleosides and having the following formula:

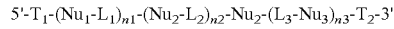

wherein:
each $Nu_1$ and $Nu_3$ is, independently, a stabilizing nucleoside;
at least 10 $Nu_2$ are β-D-2'-deoxy-2'-fluororibofuranosyl nucleosides;
each $L_1$, $L_2$ and $L_3$ is, independently, an internucleoside linking group;
each $T_1$ and $T_2$ is, independently, H, a hydroxyl protecting group, an optionally linked conjugate group or a capping group;
$n_1$ is from 0 to about 3;
$n_2$ is from about 14 to about 22;
$n_3$ is from 0 to about 3; and
provided that if $n_1$ is 0 then $T_1$ is not H or a hydroxyl protecting group, and if $n_3$ is 0, then $T_2$ is not H or a hydroxyl protecting group.

In some embodiments, each stabilizing nucleoside provides enhanced nuclease stability relative to a β-D-2'-deoxy-2'-fluororibofuranosyl nucleoside.

In other embodiments, each $Nu_2$ is a β-D-2'-deoxy-2'-fluororibofuranosyl nucleoside.

In certain embodiments, each $Nu_2$ is, independently, a stabilizing nucleoside or a β-D-2'-deoxy-2'-fluororibofuranosyl nucleoside.

In further embodiments, the $Nu_2$ nucleoside linked to the 3' $Nu_1$ stabilizing nucleoside and the $Nu_2$ nucleoside linked to the 5' $Nu_3$ stabilizing nucleoside are each, independently, a 13-D-2'-deoxy-2'-fluororibofuranosyl nucleoside.

In other embodiments, stabilizing nucleoside is, independently, a 2'-modified nucleoside. In further embodiments, the 2'-modified nucleoside is a bicyclic sugar modified nucleoside. In additional embodiments, each bicyclic sugar modified nucleoside independently comprises a D or L sugar in the alpha or beta configuration.

In certain embodiments, each stabilizing nucleoside increases the binding affinity of the oligomeric compound relative to a β-D-ribofuranosyl nucleoside.

In further embodiments, each 2'-substituent group is independently selected from O—$C_1$-$C_{12}$ alkyl, O—$CH_2$—$CH_2$—$CH_2$—$NH_2$, O—$(CH_2)_2$—O—N($R_6$)$_2$, O—$CH_2$C(=O)—N($R_6$)$_2$, O—$(CH_2)_2$—O—$(CH_2)_2$—N($R_6$)$_2$, O—$CH_2$—$CH_2$—$CH_2$—$NHR_6$, $N_3$, O—$CH_2$—CH=$CH_2$, NHCOR$_6$ or O—$CH_2$—N(H)—C(=N$R_6$)[N($R_6$)$_2$]; wherein each $R_6$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or a protecting group wherein the substituent groups are halogen, hydroxyl, amino, azido, cyano, haloalkyl, alkenyl, alkoxy, thioalkoxy, haloalkoxy or aryl.

In one embodiment, each 2'-substituent group is, independently, $O(CH_2)_{0-2}CH_3$, $O(CH_2)_2$—$OCH_3$, $O(CH_2)_2$ $SCH_3$, $OCH_2C(H)CH_2$, $O(CH_2)_2ON(CH_3)_2$ or $OCH_2C(=O)N(H)CH_3$. In another embodiment, each 2'-substituent group is, independently, $OCH_3$ or O—$(CH_2)_2$—$OCH_3$. In further embodiments, each 2'-substituent group is O—$(CH_2)_2$—$OCH_3$.

In one embodiment, each bicyclic sugar modified nucleoside independently comprises from 1 to 4 of the linked biradical groups. In another embodiment, each bicyclic sugar modified nucleoside independently comprises 2 or 3 of the linked biradical groups. In another embodiment, each bicyclic sugar modified nucleoside comprises 2 of the linked biradical groups.

In one embodiment, each bridge group of a bicyclic sugar modified nucleoside is, independently, —CH$_2$—, —(CH$_2$)$_2$—, —CH$_2$—O—, —(CH$_2$)$_2$—O— or —CH$_2$—N(R$_3$)—O— wherein R$_3$ is H or C$_1$-C$_{12}$ alkyl. In another embodiment, each bridge group is, independently, —CH$_2$—O— or —(CH$_2$)$_2$—O—.

In one embodiment, the sugar configuration of each bicyclic sugar modified nucleoside is, independently, beta-D or alpha-L.

In certain embodiments, each of the stabilizing nucleosides independently has the formula:

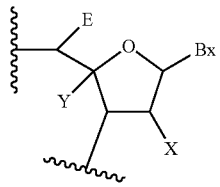

I wherein:
Bx is a heterocyclic base moeity;
E is H, C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl or substituted C$_2$-C$_6$ alkynyl;
Y is H and X is O—C$_1$-C$_{10}$ alkyl, O—C$_2$-C$_{10}$ alkenyl, O—C$_2$-C$_{10}$ alkynyl, substituted O—C$_1$-C$_{10}$ alkyl, substituted O—C$_2$-C$_{10}$ alkenyl, substituted O—C$_2$-C$_{10}$ alkynyl, amino, substituted amino or azido; or
X is H and Y is C$_1$-C$_{10}$ alkyl, substituted C$_1$-C$_{10}$ alkyl, amino or substituted amino; or
Y and X together comprises a bridge group comprising from 1 to 8 linked biradical groups independently selected from —O—, —S—, —N(R$_4$)—, —C(R$_4$)(R$_5$)—, —C(R$_4$)═C(R$_4$)—, —C(R$_4$)═N—, —C(═NR$_4$)—, —Si(R$_4$)$_2$—, —S(═O)$_2$—, —SO—, —C(═O)— and —C(═S)—;
each R$_4$ and R$_5$ is, independently, H, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, substituted oxy (—O—), amino, substituted amino, azido, carboxyl, substituted carboxyl, acyl, substituted acyl, CN, thiol, substituted thiol, sulfonyl (S(═O)$_2$—H), substituted sulfonyl, sulfoxyl (S(═O)—H) or substituted sulfoxyl;
and each substituent group is, independently, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, amino, substituted amino, acyl, substituted acyl, C$_1$-C$_{12}$ aminoalkyl, C$_1$-C$_{12}$ aminoalkoxy, substituted C$_1$-C$_{12}$ aminoalkyl, substituted C$_1$-C$_{12}$ aminoalkoxy or a protecting group.'

In one embodiment, n1 and n3 are each, independently, from 1 to about 3. In another embodiment, n$_1$ and n$_3$ are each, independently, from 2 to about 3. In a further embodiment, n$_1$ is 1 or 2 and n$_3$ is 2 or 3. In another embodiment, n$_1$ and n$_3$ are each 2.

In one embodiments, at least one of n1 and n3 is greater than zero. In another embodiment, n1 and n3 are each greater than zero. In other embodiments, one of n1 and n3 is greater than zero. In further embodiments, one of n1 and n3 is greater than one.

In one embodiment, n$_2$ is from 16 to 20. In another embodiment, n$_2$ is from 17 to 19.

In one embodiment, about 2 to about 8 of the Nu$_2$ nucleosides are stabilizing nucleosides. In another embodiment, from about 2 to about 6 of the Nu$_2$ nucleosides are stabilizing nucleosides. In further embodiments, from about 3 to about 4 of the Nu$_2$ nucleosides are stabilizing nucleosides. In additional embodiments, 3 of the Nu$_2$ nucleosides are stabilizing nucleosides.

In one embodiment, each of the Nu$_2$ stabilizing nucleosides is separated from the Nu$_3$ stabilizing nucleosides by from 2 to about 8 β-D-2'-deoxy-2'-fluororibofuranosyl nucleosides. In other embodiments each of the Nu$_2$ stabilizing nucleosides is separated from the Nu$_3$ stabilizing nucleosides by from 3 to about 8 β-D-2'-deoxy-2'-fluororibofuranosyl nucleosides. In further embodiments each of the Nu$_2$ stabilizing nucleosides is separated from the Nu$_3$ stabilizing nucleosides by from 5 to about 8 β-D-2'-deoxy-2'-fluororibofuranosyl nucleosides.

In one embodiment, oligomeric compounds comprise from 2 to about 6 Nu$_2$ stabilizing nucleosides. In another embodiment, oligomeric compounds comprise 3 Nu$_2$ stabilizing nucleosides.

In one embodiment, each of the Nu$_2$ stabilizing nucleosides are linked together in one contiguous sequence. In another embodiment, at least two of the Nu$_2$ stabilizing nucleosides are separated by at least one of the β-D-2'-deoxy-2'-fluororibofuranosyl nucleosides. In a further embodiment, each of the Nu$_2$ stabilizing nucleosides is separated by at least one of the β-D-2'-deoxy-2'-fluororibofuranosyl nucleosides.

In one embodiment, at least two contiguous sequences of the Nu$_2$ β-D-2'-deoxy-2'-fluororibofuranosyl nucleosides are separated by at least one of the stabilizing nucleosides wherein each of the contiguous sequences have the same number of β-D-2'-deoxy-2'-fluororibofuranosyl nucleosides.

In one embodiment, the oligomeric compound comprises from about 18 to about 26 nucleosides in length. In another embodiment, the oligomeric compound comprises from about 19 to about 24 nucleosides in length.

In one embodiment, T$_1$ and T$_2$ are each, independently, H or a hydroxyl protecting group. In another embodiment, at least one of T$_1$ and T$_2$ is 4,4'-dimethoxytrityl. In a further embodiment, at least one of T$_1$ and T$_2$ is an optionally linked conjugate group. In an additional embodiment, at least one of T$_1$ and T$_2$ is a capping group. In a further embodiment, the capping group is an inverted deoxy abasic group.

In one embodiment, each L$_1$, L$_2$, and L$_3$ is, independently, a phosphodiester or phosphorothioate internucleoside linking group. In another embodiment, each L$_1$, L$_2$, and L$_3$ is a phosphorothioate internucleoside linking group. In a further embodiment, at least one of L$_1$, L$_2$, and L$_3$ is a stabilizing internucleoside linking group that provides enhanced stability to nuclease degradation as compared to stability provided by a phosphodiester internucleoside linking group. In a further embodiment, each L$_1$, L$_2$, and L$_3$ is a stabilizing internucleoside linking group. In additional embodiments, each of the stabilizing internucleoside linking groups is a phosphorus containing internucleoside linking group. In other embodiments, each of the stabilizing internucleoside linking groups is, independently, a phosphorus containing internucleoside linking group or a non-phosphorus containing internucleoside linking group.

The present invention provides oligomeric compounds having a contiguous sequence of nucleotides and having the formula I:

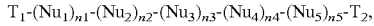

$T_1-(Nu_1)_{n1}-(Nu_2)_{n2}-(Nu_3)_{n3}-(Nu_4)_{n4}-(Nu_5)_{n5}-T_2$, wherein:

$Nu_1$ and $Nu_2$ are, independently, 2' stabilizing nucleosides;

$Nu_1$ and $Nu_4$ are β-D-2'-deoxy-2'-fluororibofuranosyl nucleosides;

$Nu_3$ is a 2'-modified nucleoside;

each of n1 and n5 is, independently, from 0 to 3;

the sum of n2 plus n4 is between 10 and 25;

n3 is from 0 and 5; and each $T_1$ and $T_2$ is, independently, H, a hydroxyl protecting group, an optionally linked conjugate group or a capping group.

In one embodiment, the sum of n2 and n4 is 16 or 17. In another embodiment, n1 is 2; n3 is 2 or 3; and n5 is 2.

In certain embodiments, formula I is selected from:
a) formula I: n1=2, n2=19, n3=0, n4=0, n5=2;
b) formula I: n1=2, n2=2, n3=3, n4=14, n5=2;
c) formula I: n1=2, n2=5, n3=3, n4=11, n5=2;
d) formula I: n1=2, n2=8, n3=3, n4=8, n5=2;
e) formula I: n1=2, n2=11, n3=3, n4=5, n5=2;
f) formula I: n1=2, n2=14, n3=3, n4=2, n5=2;
g) formula I: n1=2, n2=9, n3=3, n4=7, n5=2;
h) formula I: n1=2, n2=10, n3=3, n4=6, n5=2;
i) formula I: n1=2, n2=12, n3=3, n4=4, n5=2;
j) formula I: n1=2, n2=3, n3=3, n4=13, n5=2;
k) formula I: n1=2, n2=4, n3=3, n4=12, n5=2;
l) formula I: n1=2, n2=6, n3=3, n4=10, n5=2;
m) formula I: n1=2, n2=7, n3=3, n4=9, n5=2;
n) formula I: n1=2, n2=13, n3=3, n4=3, n5=2;
o) formula I: n1=2, n2=8, n3=6, n4=5, n5=2;
p) formula I: n1=2, n2=2, n3=2, n4=15, n5=2;
q) formula I: n1=2, n2=3, n3=2, n4=14, n5=2;
r) formula I: n1=2, n2=4, n3=2, n4=13, n5=2;
s) formula I: n1=2, n2=5, n3=2, n4=12, n5=2;
t) formula I: n1=2, n2=6, n3=2, n4=11, n5=2;
u) formula I: n1=2, n2=7, n3=2, n4=10, n5=2;
v) formula I: n1=2, n2=8, n3=2, n4=9, n5=2;
w) formula I: n1=2, n2=9, n3=2, n4=8, n5=2;
x) formula I: n1=2, n2=10, n3=2, n4=7, n5=2;
y) formula I: n1=2, n2=11, n3=2, n4=6, n5=2;
z) formula I: n1=2, n2=12, n3=2, n4=5, n5=2;
aa) formula I: n1=2, n2=13, n3=2, n4=4, n5=2;
bb) formula I: n5=2, n2=14, n3=2, n4=3, n5=2; or
cc) formula I: n1=2, n2=15, n3=2, n4=2, n5=2.

In some embodiments, $Nu_1$ and $Nu_5$ are, independently, 2'-modified nucleosides.

In one embodiment, $Nu_1$ is $O—(CH_2)_2—OCH_3$, $Nu_3$ is $O—(CH_2)_2—OCH_3$, $Nu_5O—(CH_2)_2—OCH_3$, $T_1$ is H and $T_2$ is H, and formula I is selected from:
a) formula I: n1=2, n2=19, n3=0, n4=0, n5=2;
b) formula I: n1=2, n2=2, n3=3, n4=14, n5=2;
c) formula I: n1=2, n2=5, n3=3, n4=11, n5=2;
d) formula I: n1=2, n2=8, n3=3, n4=8, n5=2;
e) formula I: n1=2, n2=11, n3=3, n4=5, n5=2;
f) formula I: n1=2, n2=14, n3=3, n4=2, n5=2;
g) formula I: n1=2, n2=9, n3=3, n4=7, n5=2;
h) formula I: n1=2, n2=10, n3=3, n4=6, n5=2;
i) formula I: n1=2, n2=12, n3=3, n4=4, n5=2;
j) formula I: n1=2, n2=3, n3=3, n4=13, n5=2;
k) formula I: n1=2, n2=4, n3=3, n4=12, n5=2;
l) formula I: n1=2, n2=6, n3=3, n4=10, n5=2;
m) formula I: n1=2, n2=7, n3=3, n4=9, n5=2;
n) formula I: n1=2, n2=13, n3=3, n4=3, n5=2;
o) formula I: n1=2, n2=8, n3=6, n4=5, n5=2;
p) formula I: n1=2, n2=2, n3=2, n4=15, n5=2;
q) formula I: n1=2, n2=3, n3=2, n4=14, n5=2;
r) formula I: n1=2, n2=4, n3=2, n4=13, n5=2;
s) formula I: n1=2, n2=5, n3=2, n4=12, n5=2;
t) formula I: n1=2, n2=6, n3=2, n4=11, n5=2;
u) formula I: n1=2, n2=7, n3=2, n4=10, n5=2;
v) formula I: n1=2, n2=8, n3=2, n4=9, n5=2;
w) formula I: n1=2, n2=9, n3=2, n4=8, n5=2;
x) formula I: n1=2, n2=10, n3=2, n4=7, n5=2;
y) formula I: n1=2, n2=11, n3=2, n4=6, n5=2;
z) formula I: n1=2, n2=12, n3=2, n4=5, n5=2;
aa) formula I: n1=2, n2=13, n3=2, n4=4, n5=2;
bb) formula I: n5=2, n2=14, n3=2, n4=3, n5=2; or
cc) formula I: n1=2, n2=15, n3=2, n4=2, n5=2.

In one embodiment, the oligomeric compounds comprise at least one phosphorothioate internucleoside linkage. In other embodiments, each internucleoside linkage is a phosphorothioate internucleoside linkage.

In one embodiment, T1 is H and T2 is H.

The present invention provides methods of inhibiting miRNA activity, comprising contacting a cell with an oligomeric compound comprising a contiguous sequence of about 17 to about 29 nucleosides linked by internucleoside linking groups, said sequence having an internal region located between two external regions, each external region independently comprises from 1 to about 3 nucleosides, each external region comprises a stabilizing nucleoside, the internal region comprises at least 10 β-D-2'-deoxy-2'-fluororibofuranosyl nucleosides, and each of the stabilizing nucleosides provides enhanced nuclease stability relative to a β-D-2'-deoxy-2'-fluororibofuranosyl nucleoside, wherein the oligomeric compound comprises a sequence substantially complementary to a miRNA.

The present invention further provides methods of inhibiting miRNA activity, comprising contacting a cell with an oligomeric compound having a sequence substantially complementary to a miRA and comprising a contiguous sequence of about 17 to about 29 nucleosides linked by internucleoside linking groups, said sequence having an internal region located between two external regions, each external region independently comprises from 1 to about 3 nucleosides, each external region comprises a stabilizing modification, and the internal region comprises at least 10 β-D-2'-deoxy-2'-fluororibofuranosyl nucleosides.

The present invention additionally provides methods of inhibition miRNA activity comprising contacting a cell with an oligomeric compound with an oligomeric compound comprising a sequence substantially complementary to a miRNA and having the following formula:

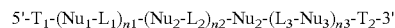

$5'-T_1-(Nu_1-L_1)_{n1}-(Nu_2-L_2)_{n2}-Nu_2-(L_3-Nu_3)_{n3}-T_2-3'$ wherein:

each $Nu_1$ and $Nu_3$ is, independently, a stabilizing nucleoside;

at least 10 $Nu_2$ are β-D-2'-deoxy-2'-fluororibofuranosyl nucleosides;

each $L_1$, $L_2$ and $L_3$ is, independently, an internucleoside linking group;

each $T_1$ and $T_2$ is, independently, H, a hydroxyl protecting group, an optionally linked conjugate group or a capping group;

$n_1$ is from 0 to about 3;

$n_2$ is from about 14 to about 22;

$n_3$ is from 0 to about 3; and provided that if $n_1$ is 0 then $T_1$ is not H or a hydroxyl protecting group, and if $n_3$ is 0, then $T_2$ is not H or a hydroxyl protecting group.

The present invention also provides methods of inhibiting miRNA activity comprising contacting a cell with an oligomeric compound having a sequence substantially complementary to a miRNA and having the following formula I:

$$T_1\text{-}(Nu_1)_{n1}\text{-}(Nu_2)_{n2}\text{-}(Nu_3)_{n3}\text{-}(Nu_4)_{n4}\text{-}(Nu_5)_{n5}\text{-}T_2,$$

wherein:

$Nu_1$ and $Nu_5$ are, independently, 2' stabilizing nucleosides;

$Nu_2$ and $Nu_4$ are β-D-2'-deoxy-2'-fluororibofuranosyl nucleosides;

$Nu_3$ is a 2'-modified nucleoside;

each of n1 and n5 is, independently, from 0 to 3;

the sum of n2 plus n4 is between 10 and 25;

n3 is from 0 and 5; and each $T_1$ and $T_2$ is, independently, H, a hydroxyl protecting group, an optionally linked conjugate group or a capping group.

In one embodiment, the oligomeric compound is fully complementary to a miRNA. In other embodiments, the oligomeric compound comprises a sequence selected from SEQ ID NOs 1 to 470.

In one embodiment, the cell is in vitro. In another embodiment, the cell is in vivo. In other embodiments, contacting the cell comprises administering to an animal.

In one embodiment, the methods comprise inhibition miRNA activity in vivo by contacting an animal with an oligomeric compound of the invention.

The present invention provides methods of inhibiting miR-122 activity in vivo, comprising contacting an animal with the oligomeric compound comprising the nucleobase sequence of SEQ ID NO: 19 and having the formula $T_1\text{-}(Nu_1)_{n1}\text{-}(Nu_2)_{n2}\text{-}(Nu_3)_{n3}\text{-}(Nu_4)_{n4}\text{-}(Nu_5)_{n5}\text{-}T_2$, wherein $Nu_1$ is O—$(CH_2)_2$—$OCH_3$, $Nu_3$ is O—$(CH_2)_2$—$OCH_3$, $Nu_5$O—$(CH_2)_2$—$OCH_3$, $T_1$ is H and $T_2$ is H, and wherein formula I is selected from:

a) formula I: n1=2, n2=19, n3=0, n4=0, n5=2;
b) formula I: n1=2, n2=2, n3=3, n4=14, n5=2;
c) formula I: n1=2, n2=5, n3=3, n4=11, n5=2;
d) formula I: n1=2, n2=8, n3=3, n4=8, n5=2;
e) formula I: n1=2, n2=11, n3=3, n4=5, n5=2;
f) formula I: n1=2, n2=14, n3=3, n4=2, n5=2;
g) formula I: n1=2, n2=9, n3=3, n4=7, n5=2;
h) formula I: n1=2, n2=10, n3=3, n4=6, n5=2;
i) formula I: n1=2, n2=12, n3=3, n4=4, n5=2;
j) formula I: n1=2, n2=3, n3=3, n4=13, n5=2;
k) formula I: n1=2, n2=4, n3=3, n4=12, n5=2;
l) formula I: n1=2, n2=6, n3=3, n4=10, n5=2;
m) formula I: n1=2, n2=7, n3=3, n4=9, n5=2;
n) formula I: n1=2, n2=13, n3=3, n4=3, n5=2;
o) formula I: n1=2, n2=8, n3=6, n4=5, n5=2;
p) formula I: n1=2, n2=2, n3=2, n4=15, n5=2;
q) formula I: n1=2, n2=3, n3=2, n4=14, n5=2;
r) formula I: n1=2, n2=4, n3=2, n4=13, n5=2;
s) formula I: n1=2, n2=5, n3=2, n4=12, n5=2;
t) formula I: n1=2, n2=6, n3=2, n4=11, n5=2;
u) formula I: n1=2, n2=7, n3=2, n4=10, n5=2;
v) formula I: n1=2, n2=8, n3=2, n4=9, n5=2;
w) formula I: n1=2, n2=9, n3=2, n4=8, n5=2;
x) formula I: n1=2, n2=10, n3=2, n4=7, n5=2;
y) formula I: n1=2, n2=11, n3=2, n4=6, n5=2;
z) formula I: n1=2, n2=12, n3=2, n4=5, n5=2;
aa) formula I: n1=2, n2=13, n3=2, n4=4, n5=2;
bb) formula I: n5=2, n2=14, n3=2, n4=3, n5=2; or cc) formula I: n1=2, n2=15, n3=2, n4=2, n5=2.

In one embodiment, the methods inhibiting miR-122 activity in vivo further comprise increasing liver ALDOA mRNA levels. In another embodiment, the methods inhibiting miR-122 activity in vivo further comprised decreasing plasma total cholesterol levels.

In one embodiment, oligomeric compounds comprise 20 to 24 linked nucleosides. In other embodiments, oligomeric compounds comprise 21 linked nucleosides. In further embodiments, oligomeric compounds comprise 22 linked nucleosides. In additional embodiments, oligomeric compounds comprise 23 linked nucleosides.

DETAILED DESCRIPTION

MiRNA have been found to be aberrantly expressed in disease states, i.e. specific miRNAs are present at higher or lower levels in a diseased cell or tissue as compared to healthy cell or tissue. The present invention provides, inter alia, compositions and methods for modulating miRNA activity, including miRNA activity associated with disease states. Certain compositions of the present invention are particularly suited for use in vivo methods due to their potent activity and/or improved therapeutic index.

It has been found that the use of chemically synthesized nucleotides in an oligomeric compound can affect the ability of the oligomeric to bind to, and modulate, small non-coding RNA such as miRNA. It has further been discovered that the arrangement of chemically modified nucleotides in an oligomeric compound can affect the ability of the oligomeric to bind to, and modulate, a small non-coding RNA such as miRNA. Additionally, it has been discovered that the arrangement of chemically modified nucleotides in an oligomeric compound can affect the therapeutic index of the oligomeric compound. The present invention provides, inter alia, oligomeric compounds having potent activity and improved therapeutic index for use in the modulation of small non-coding RNA, such as miRNA.

In vivo testing of an oligomeric compound having 19 β-D-2'-deoxy-2'-fluororibofuranosyl nucleosides flanked on each of the 5' and 3' ends by two 2'-MOE stabilizing nucleosides has demonstrated that the oligomeric compound, while having a Tm similar to that of a 2'-uniform MOE oligomeric compound, had a greatly enhanced ability to inhibit a miRNA in vivo. Accordingly, the present invention provides, inter alia, chemically synthesized oligomeric compounds that each include a contiguous sequence of nucleosides that are linked by internucleoside linking groups. Each oligomeric compound includes about ten β-D-2'-deoxy-2'-fluororibofuranosyl nucleosides and can further include one or more external regions comprising stabilizing nucleotides. In one aspect, each nucleoside in the oligomeric compound is a β-D-2'-deoxy-2'-fluororibofuranosyl nucleoside and one or both of the 3' and 5' terminal nucleosides are attached to a conjugate or capping group. In a further aspect at least ten nucleosides of the oligomeric compound are β-D-2'-deoxy-2'-fluororibofuranosyl nucleosides and one or more additional stabilizing nucleosides are attached to one or both of the 3' and 5' ends.

Further testing demonstrated that the therapeutic index of the oligomeric compound could be improved by incorporating certain nucleotides or nucleosides in the internal region of the oligomeric compound. An oligomeric compound comprising an internal region of β-D-2'-deoxy-2'-fluororibofuranosyl nucleosides flanked on each of the 5' and 3' ends by 2'-MOE stabilizing nucleosides and further comprising a 2'-MOE nucleosides in the internal region was shown to have reduced immunostimulatory activity as compared to the oligomeric compound without the internal 2' MOE nucleosides. Accordingly, the present invention provides, inter alia, an oligomeric compound wherein at least ten nucleosides of the oligomeric compound are β-D-2'-deoxy-2'-fluororibofuranosyl nucleosides, one or more additional stabilizing nucleotides are attached to one or both of the 3' and 5' ends and 2' MOE nucleosides are included at one or more internal positions of the oligomeric compound. In certain embodiments, at least ten nucleosides of the oligomeric compound are β-D-2'-deoxy-2'-fluororibofuranosyl nucleosides, one or more additional stabilizing nucleosides are attached to one or both of the 3' and 5' ends, and 2'-modified nucleosides are included at one or more internal positions of the oligomeric compound. In other embodiments, at least ten nucleosides of the oligomeric compound are β-D-2'-deoxy-2'-fluororibofuranosyl nucleosides, one or more additional stabilizing modifications are attached to one or both of the 3' and 5' ends, and stabilizing nucleosides are included at one or more internal positions of the oligomeric compound. Generally, the stabilizing modifications at the 3' and 5' ends provide enhanced stability relative to an oligomeric compound having only β-D-2'-deoxy-2'-fluororibofuranosyl nucleosides. In certain embodiments, the stabilizing modifications are stabilizing nucleosides and/or stabilizing internucleoside linkage groups.

Oligomeric compounds having potent activity and improved therapeutic index can be described by the following formula: $T_1$-$(Nu_1)_{n1}$-$(Nu_2)_{n2}$-$(Nu_3)_{n3}$-$(Nu_4)_{n4}$-$(Nu_5)_{n5}$-$T_2$, wherein: $Nu_1$ and $Nu_5$ are, independently, 2' stabilizing nucleosides; $Nu_2$ and $Nu_4$ are β-D-2'-deoxy-2'-fluororibofuranosyl nucleosides; $Nu_3$ is a 2'-modified nucleoside; each of n1 and n5 is, independently, from 0 to 3; the sum of n2 plus n4 is between 10 and 25; n3 is from 0 and 5; and each $T_1$ and $T_2$ is, independently, H, a hydroxyl protecting group, an optionally linked conjugate group or a capping group.

In one embodiment, the oligomeric compounds can be further described has having a configuration of n1, n2, n3, n4, and n5 as follows:

n1=2, n2=19, n3=0, n4=0, n5=2 (configuration A);
n1=2, n2=2, n3=3, n4=14, n5=2 (configuration B);
n1=2, n2=5, n3=3, n4=11, n5=2 (configuration C);
n1=2, n2=8, n3=3, n4=8, n5=2 (configuration D);
n1=2, n2=11, n3=3, n4=5, n5=2 (configuration E);
n1=2, n2=14, n3=3, n4=2, n5=2 (configuration F);
n1=2, n2=9, n3=3, n4=7, n5=2 (configuration G);
n1=2, n2=10, n3=3, n4=6, n5=2 (configuration H);
n1=2, n2=12, n3=3, n4=4, n5=2 (configuration I);
n1=2, n2=3, n3=3, n4=13, n5=2 (configuration J);
n1=2, n2=4, n3=3, n4=12, n5=2 (configuration K);
n1=2, n2=6, n3=3, n4=10, n5=2 (configuration L);
n1=2, n2=7, n3=3, n4=9, n5=2 (configuration M);
n1=2, n2=13, n3=3, n4=3, n5=2 (configuration N);
n1=2, n2=8, n3=6, n4=5, n5=2 (configuration O);
n1=2, n2=2, n3=2, n4=15, n5=2 (configuration P);
n1=2, n2=3, n3=2, n4=14, n5=2 (configuration Q);
n1=2, n2=4, n3=2, n4=13, n5=2 (configuration R);
n1=2, n2=5, n3=2, n4=12, n5=2 (configuration S);
n1=2, n2=6, n3=2, n4=11, n5=2 (configuration T);
n1=2, n2=7, n3=2, n4=10, n5=2 (configuration U);
n1=2, n2=8, n3=2, n4=9, n5=2 (configuration V);
n1=2, n2=9, n3=2, n4=8, n5=2 (configuration W);
n1=2, n2=10, n3=2, n4=7, n5=2 (configuration X);
n1=2, n2=11, n3=2, n4=6, n5=2 (configuration Y);
n1=2, n2=12, n3=2, n4=5, n5=2 (configuration Z);
n1=2, n2=13, n3=2, n4=4, n5=2 (configuration AA);
n5=2, n2=14, n3=2, n4=3, n5=2 (configuration BB); or
n1=2, n2=15, n3=2, n4=2, n5=2 (configuration CC).

In certain embodiments, oligomeric compounds can have the following pairings of nucleotide sequence and formula I, as shown in Table 1, wherein each nucleoside is linked by phosphorothioate internucleoside linkages. In other embodiments, the examples of formula I shown in Table 1 are applied to any oligomeric compound comprising 23 linked nucleosides.

TABLE 1

| SEQ ID NO | n1 | n2 | n3 | n4 | n5 | $Nu_1$ | $Nu_3$ | $Nu_5$ | $T_1$ | $T_2$ |
|---|---|---|---|---|---|---|---|---|---|---|
| 19 | 2 | 19 | 0 | 0 | 2 | 2'-MOE | 2'-MOE | 2'-MOE | H | H |
| 19 | 2 | 2 | 3 | 14 | 2 | 2'-MOE | 2'-MOE | 2'-MOE | H | H |
| 19 | 2 | 5 | 3 | 11 | 2 | 2'-MOE | 2'-MOE | 2'-MOE | H | H |
| 19 | 2 | 8 | 3 | 8 | 2 | 2'-MOE | 2'-MOE | 2'-MOE | H | H |
| 19 | 2 | 11 | 3 | 5 | 2 | 2'-MOE | 2'-MOE | 2'-MOE | H | H |
| 19 | 2 | 14 | 3 | 2 | 2 | 2'-MOE | 2'-MOE | 2'-MOE | H | H |
| 19 | 2 | 9 | 3 | 7 | 2 | 2'-MOE | 2'-MOE | 2'-MOE | H | H |
| 19 | 2 | 10 | 3 | 6 | 2 | 2'-MOE | 2'-MOE | 2'-MOE | H | H |
| 19 | 2 | 12 | 3 | 4 | 2 | 2'-MOE | 2'-MOE | 2'-MOE | H | H |
| 19 | 2 | 3 | 3 | 13 | 2 | 2'-MOE | 2'-MOE | 2'-MOE | H | H |
| 19 | 2 | 4 | 3 | 12 | 2 | 2'-MOE | 2'-MOE | 2'-MOE | H | H |
| 19 | 2 | 6 | 3 | 10 | 2 | 2'-MOE | 2'-MOE | 2'-MOE | H | H |
| 19 | 2 | 7 | 3 | 9 | 2 | 2'-MOE | 2'-MOE | 2'-MOE | H | H |
| 19 | 2 | 13 | 3 | 3 | 2 | 2'-MOE | 2'-MOE | 2'-MOE | H | H |
| 19 | 2 | 8 | 6 | 5 | 2 | 2'-MOE | 2'-MOE | 2'-MOE | H | H |
| 19 | 2 | 2 | 2 | 15 | 2 | 2'-MOE | 2'-MOE | 2'-MOE | H | H |
| 19 | 2 | 3 | 2 | 14 | 2 | 2'-MOE | 2'-MOE | 2'-MOE | H | H |
| 19 | 2 | 4 | 2 | 13 | 2 | 2'-MOE | 2'-MOE | 2'-MOE | H | H |
| 19 | 2 | 5 | 2 | 12 | 2 | 2'-MOE | 2'-MOE | 2'-MOE | H | H |
| 19 | 2 | 6 | 2 | 11 | 2 | 2'-MOE | 2'-MOE | 2'-MOE | H | H |
| 19 | 2 | 7 | 2 | 10 | 2 | 2'-MOE | 2'-MOE | 2'-MOE | H | H |
| 19 | 2 | 8 | 2 | 9 | 2 | 2'-MOE | 2'-MOE | 2'-MOE | H | H |
| 19 | 2 | 9 | 2 | 8 | 2 | 2'-MOE | 2'-MOE | 2'-MOE | H | H |
| 19 | 2 | 10 | 2 | 7 | 2 | 2'-MOE | 2'-MOE | 2'-MOE | H | H |
| 19 | 2 | 11 | 2 | 6 | 2 | 2'-MOE | 2'-MOE | 2'-MOE | H | H |
| 19 | 2 | 12 | 2 | 5 | 2 | 2'-MOE | 2'-MOE | 2'-MOE | H | H |
| 19 | 2 | 13 | 2 | 4 | 2 | 2'-MOE | 2'-MOE | 2'-MOE | H | H |
| 19 | 2 | 14 | 2 | 3 | 2 | 2'-MOE | 2'-MOE | 2'-MOE | H | H |
| 19 | 2 | 15 | 2 | 2 | 2 | 2'-MOE | 2'-MOE | 2'-MOE | H | H |
| 98 | 2 | 19 | 0 | 0 | 2 | 2'-MOE | 2'-MOE | 2'-MOE | H | H |
| 98 | 2 | 2 | 3 | 14 | 2 | 2'-MOE | 2'-MOE | 2'-MOE | H | H |
| 98 | 2 | 5 | 3 | 11 | 2 | 2'-MOE | 2'-MOE | 2'-MOE | H | H |
| 98 | 2 | 8 | 3 | 8 | 2 | 2'-MOE | 2'-MOE | 2'-MOE | H | H |
| 98 | 2 | 11 | 3 | 5 | 2 | 2'-MOE | 2'-MOE | 2'-MOE | H | H |
| 98 | 2 | 14 | 3 | 2 | 2 | 2'-MOE | 2'-MOE | 2'-MOE | H | H |
| 98 | 2 | 9 | 3 | 7 | 2 | 2'-MOE | 2'-MOE | 2'-MOE | H | H |
| 98 | 2 | 10 | 3 | 6 | 2 | 2'-MOE | 2'-MOE | 2'-MOE | H | H |
| 98 | 2 | 12 | 3 | 4 | 2 | 2'-MOE | 2'-MOE | 2'-MOE | H | H |
| 98 | 2 | 3 | 3 | 13 | 2 | 2'-MOE | 2'-MOE | 2'-MOE | H | H |
| 98 | 2 | 4 | 3 | 12 | 2 | 2'-MOE | 2'-MOE | 2'-MOE | H | H |
| 98 | 2 | 6 | 3 | 10 | 2 | 2'-MOE | 2'-MOE | 2'-MOE | H | H |
| 98 | 2 | 7 | 3 | 9 | 2 | 2'-MOE | 2'-MOE | 2'-MOE | H | H |
| 98 | 2 | 13 | 3 | 3 | 2 | 2'-MOE | 2'-MOE | 2'-MOE | H | H |
| 98 | 2 | 8 | 6 | 5 | 2 | 2'-MOE | 2'-MOE | 2'-MOE | H | H |
| 98 | 2 | 2 | 2 | 15 | 2 | 2'-MOE | 2'-MOE | 2'-MOE | H | H |
| 98 | 2 | 3 | 2 | 14 | 2 | 2'-MOE | 2'-MOE | 2'-MOE | H | H |
| 98 | 2 | 4 | 2 | 13 | 2 | 2'-MOE | 2'-MOE | 2'-MOE | H | H |
| 98 | 2 | 5 | 2 | 12 | 2 | 2'-MOE | 2'-MOE | 2'-MOE | H | H |
| 98 | 2 | 6 | 2 | 11 | 2 | 2'-MOE | 2'-MOE | 2'-MOE | H | H |
| 98 | 2 | 7 | 2 | 10 | 2 | 2'-MOE | 2'-MOE | 2'-MOE | H | H |
| 98 | 2 | 8 | 2 | 9 | 2 | 2'-MOE | 2'-MOE | 2'-MOE | H | H |
| 98 | 2 | 9 | 2 | 8 | 2 | 2'-MOE | 2'-MOE | 2'-MOE | H | H |
| 98 | 2 | 10 | 2 | 7 | 2 | 2'-MOE | 2'-MOE | 2'-MOE | H | H |
| 98 | 2 | 11 | 2 | 6 | 2 | 2'-MOE | 2'-MOE | 2'-MOE | H | H |
| 98 | 2 | 12 | 2 | 5 | 2 | 2'-MOE | 2'-MOE | 2'-MOE | H | H |
| 98 | 2 | 13 | 2 | 4 | 2 | 2'-MOE | 2'-MOE | 2'-MOE | H | H |
| 98 | 2 | 14 | 2 | 3 | 2 | 2'-MOE | 2'-MOE | 2'-MOE | H | H |
| 98 | 2 | 15 | 2 | 2 | 2 | 2'-MOE | 2'-MOE | 2'-MOE | H | H |
| 99 | 2 | 19 | 0 | 0 | 2 | 2'-MOE | 2'-MOE | 2'-MOE | H | H |
| 99 | 2 | 2 | 3 | 14 | 2 | 2'-MOE | 2'-MOE | 2'-MOE | H | H |
| 99 | 2 | 5 | 3 | 11 | 2 | 2'-MOE | 2'-MOE | 2'-MOE | H | H |
| 99 | 2 | 8 | 3 | 8 | 2 | 2'-MOE | 2'-MOE | 2'-MOE | H | H |
| 99 | 2 | 11 | 3 | 5 | 2 | 2'-MOE | 2'-MOE | 2'-MOE | H | H |
| 99 | 2 | 14 | 3 | 2 | 2 | 2'-MOE | 2'-MOE | 2'-MOE | H | H |
| 99 | 2 | 9 | 3 | 7 | 2 | 2'-MOE | 2'-MOE | 2'-MOE | H | H |

TABLE 1-continued

| SEQ ID NO | n1 | n2 | n3 | n4 | n5 | Nu$_1$ | Nu$_3$ | Nu$_5$ | T$_1$ | T$_2$ |
|---|---|---|---|---|---|---|---|---|---|---|
| 99 | 2 | 10 | 3 | 6 | 2 | 2'-MOE | 2'-MOE | 2'-MOE | H | H |
| 99 | 2 | 12 | 3 | 4 | 2 | 2'-MOE | 2'-MOE | 2'-MOE | H | H |
| 99 | 2 | 3 | 3 | 13 | 2 | 2'-MOE | 2'-MOE | 2'-MOE | H | H |
| 99 | 2 | 4 | 3 | 12 | 2 | 2'-MOE | 2'-MOE | 2'-MOE | H | H |
| 99 | 2 | 6 | 3 | 10 | 2 | 2'-MOE | 2'-MOE | 2'-MOE | H | H |
| 99 | 2 | 7 | 3 | 9 | 2 | 2'-MOE | 2'-MOE | 2'-MOE | H | H |
| 99 | 2 | 13 | 3 | 3 | 2 | 2'-MOE | 2'-MOE | 2'-MOE | H | H |
| 99 | 2 | 8 | 6 | 5 | 2 | 2'-MOE | 2'-MOE | 2'-MOE | H | H |
| 99 | 2 | 2 | 2 | 15 | 2 | 2'-MOE | 2'-MOE | 2'-MOE | H | H |
| 99 | 2 | 3 | 2 | 14 | 2 | 2'-MOE | 2'-MOE | 2'-MOE | H | H |
| 99 | 2 | 4 | 2 | 13 | 2 | 2'-MOE | 2'-MOE | 2'-MOE | H | H |
| 99 | 2 | 5 | 2 | 12 | 2 | 2'-MOE | 2'-MOE | 2'-MOE | H | H |
| 99 | 2 | 6 | 2 | 11 | 2 | 2'-MOE | 2'-MOE | 2'-MOE | H | H |
| 99 | 2 | 7 | 2 | 10 | 2 | 2'-MOE | 2'-MOE | 2'-MOE | H | H |
| 99 | 2 | 8 | 2 | 9 | 2 | 2'-MOE | 2'-MOE | 2'-MOE | H | H |
| 99 | 2 | 9 | 2 | 8 | 2 | 2'-MOE | 2'-MOE | 2'-MOE | H | H |
| 99 | 2 | 10 | 2 | 7 | 2 | 2'-MOE | 2'-MOE | 2'-MOE | H | H |
| 99 | 2 | 11 | 2 | 6 | 2 | 2'-MOE | 2'-MOE | 2'-MOE | H | H |
| 99 | 2 | 12 | 2 | 5 | 2 | 2'-MOE | 2'-MOE | 2'-MOE | H | H |
| 99 | 2 | 13 | 2 | 4 | 2 | 2'-MOE | 2'-MOE | 2'-MOE | H | H |
| 99 | 2 | 14 | 2 | 3 | 2 | 2'-MOE | 2'-MOE | 2'-MOE | H | H |
| 99 | 2 | 15 | 2 | 2 | 2 | 2'-MOE | 2'-MOE | 2'-MOE | H | H |
| 102 | 2 | 19 | 0 | 0 | 2 | 2'-MOE | 2'-MOE | 2'-MOE | H | H |
| 102 | 2 | 2 | 3 | 14 | 2 | 2'-MOE | 2'-MOE | 2'-MOE | H | H |
| 102 | 2 | 5 | 3 | 11 | 2 | 2'-MOE | 2'-MOE | 2'-MOE | H | H |
| 102 | 2 | 8 | 3 | 8 | 2 | 2'-MOE | 2'-MOE | 2'-MOE | H | H |
| 102 | 2 | 11 | 3 | 5 | 2 | 2'-MOE | 2'-MOE | 2'-MOE | H | H |
| 102 | 2 | 14 | 3 | 2 | 2 | 2'-MOE | 2'-MOE | 2'-MOE | H | H |
| 102 | 2 | 9 | 3 | 7 | 2 | 2'-MOE | 2'-MOE | 2'-MOE | H | H |
| 102 | 2 | 10 | 3 | 6 | 2 | 2'-MOE | 2'-MOE | 2'-MOE | H | H |
| 102 | 2 | 12 | 3 | 4 | 2 | 2'-MOE | 2'-MOE | 2'-MOE | H | H |
| 102 | 2 | 3 | 3 | 13 | 2 | 2'-MOE | 2'-MOE | 2'-MOE | H | H |
| 102 | 2 | 4 | 3 | 12 | 2 | 2'-MOE | 2'-MOE | 2'-MOE | H | H |
| 102 | 2 | 6 | 3 | 10 | 2 | 2'-MOE | 2'-MOE | 2'-MOE | H | H |
| 102 | 2 | 7 | 3 | 9 | 2 | 2'-MOE | 2'-MOE | 2'-MOE | H | H |
| 102 | 2 | 13 | 3 | 3 | 2 | 2'-MOE | 2'-MOE | 2'-MOE | H | H |
| 102 | 2 | 8 | 6 | 5 | 2 | 2'-MOE | 2'-MOE | 2'-MOE | H | H |
| 102 | 2 | 2 | 2 | 15 | 2 | 2'-MOE | 2'-MOE | 2'-MOE | H | H |
| 102 | 2 | 3 | 2 | 14 | 2 | 2'-MOE | 2'-MOE | 2'-MOE | H | H |
| 102 | 2 | 4 | 2 | 13 | 2 | 2'-MOE | 2'-MOE | 2'-MOE | H | H |
| 102 | 2 | 5 | 2 | 12 | 2 | 2'-MOE | 2'-MOE | 2'-MOE | H | H |
| 102 | 2 | 6 | 2 | 11 | 2 | 2'-MOE | 2'-MOE | 2'-MOE | H | H |
| 102 | 2 | 7 | 2 | 10 | 2 | 2'-MOE | 2'-MOE | 2'-MOE | H | H |
| 102 | 2 | 8 | 2 | 9 | 2 | 2'-MOE | 2'-MOE | 2'-MOE | H | H |
| 102 | 2 | 9 | 2 | 8 | 2 | 2'-MOE | 2'-MOE | 2'-MOE | H | H |
| 102 | 2 | 10 | 2 | 7 | 2 | 2'-MOE | 2'-MOE | 2'-MOE | H | H |
| 102 | 2 | 11 | 2 | 6 | 2 | 2'-MOE | 2'-MOE | 2'-MOE | H | H |
| 102 | 2 | 12 | 2 | 5 | 2 | 2'-MOE | 2'-MOE | 2'-MOE | H | H |
| 102 | 2 | 13 | 2 | 4 | 2 | 2'-MOE | 2'-MOE | 2'-MOE | H | H |
| 102 | 2 | 14 | 2 | 3 | 2 | 2'-MOE | 2'-MOE | 2'-MOE | H | H |
| 102 | 2 | 15 | 2 | 2 | 2 | 2'-MOE | 2'-MOE | 2'-MOE | H | H |
| 111 | 2 | 19 | 0 | 0 | 2 | 2'-MOE | 2'-MOE | 2'-MOE | H | H |
| 111 | 2 | 2 | 3 | 14 | 2 | 2'-MOE | 2'-MOE | 2'-MOE | H | H |
| 111 | 2 | 5 | 3 | 11 | 2 | 2'-MOE | 2'-MOE | 2'-MOE | H | H |
| 111 | 2 | 8 | 3 | 8 | 2 | 2'-MOE | 2'-MOE | 2'-MOE | H | H |
| 111 | 2 | 11 | 3 | 5 | 2 | 2'-MOE | 2'-MOE | 2'-MOE | H | H |
| 111 | 2 | 14 | 3 | 2 | 2 | 2'-MOE | 2'-MOE | 2'-MOE | H | H |
| 111 | 2 | 9 | 3 | 7 | 2 | 2'-MOE | 2'-MOE | 2'-MOE | H | H |
| 111 | 2 | 10 | 3 | 6 | 2 | 2'-MOE | 2'-MOE | 2'-MOE | H | H |
| 111 | 2 | 12 | 3 | 4 | 2 | 2'-MOE | 2'-MOE | 2'-MOE | H | H |
| 111 | 2 | 3 | 3 | 13 | 2 | 2'-MOE | 2'-MOE | 2'-MOE | H | H |
| 111 | 2 | 4 | 3 | 12 | 2 | 2'-MOE | 2'-MOE | 2'-MOE | H | H |
| 111 | 2 | 6 | 3 | 10 | 2 | 2'-MOE | 2'-MOE | 2'-MOE | H | H |
| 111 | 2 | 7 | 3 | 9 | 2 | 2'-MOE | 2'-MOE | 2'-MOE | H | H |
| 111 | 2 | 13 | 3 | 3 | 2 | 2'-MOE | 2'-MOE | 2'-MOE | H | H |
| 111 | 2 | 8 | 6 | 5 | 2 | 2'-MOE | 2'-MOE | 2'-MOE | H | H |
| 111 | 2 | 2 | 2 | 15 | 2 | 2'-MOE | 2'-MOE | 2'-MOE | H | H |
| 111 | 2 | 3 | 2 | 14 | 2 | 2'-MOE | 2'-MOE | 2'-MOE | H | H |
| 111 | 2 | 4 | 2 | 13 | 2 | 2'-MOE | 2'-MOE | 2'-MOE | H | H |
| 111 | 2 | 5 | 2 | 12 | 2 | 2'-MOE | 2'-MOE | 2'-MOE | H | H |
| 111 | 2 | 6 | 2 | 11 | 2 | 2'-MOE | 2'-MOE | 2'-MOE | H | H |
| 111 | 2 | 7 | 2 | 10 | 2 | 2'-MOE | 2'-MOE | 2'-MOE | H | H |
| 111 | 2 | 8 | 2 | 9 | 2 | 2'-MOE | 2'-MOE | 2'-MOE | H | H |
| 111 | 2 | 9 | 2 | 8 | 2 | 2'-MOE | 2'-MOE | 2'-MOE | H | H |
| 111 | 2 | 10 | 2 | 7 | 2 | 2'-MOE | 2'-MOE | 2'-MOE | H | H |
| 111 | 2 | 11 | 2 | 6 | 2 | 2'-MOE | 2'-MOE | 2'-MOE | H | H |
| 111 | 2 | 12 | 2 | 5 | 2 | 2'-MOE | 2'-MOE | 2'-MOE | H | H |
| 111 | 2 | 13 | 2 | 4 | 2 | 2'-MOE | 2'-MOE | 2'-MOE | H | H |
| 111 | 2 | 14 | 2 | 3 | 2 | 2'-MOE | 2'-MOE | 2'-MOE | H | H |
| 111 | 2 | 15 | 2 | 2 | 2 | 2'-MOE | 2'-MOE | 2'-MOE | H | H |
| 112 | 2 | 19 | 0 | 0 | 2 | 2'-MOE | 2'-MOE | 2'-MOE | H | H |
| 112 | 2 | 2 | 3 | 14 | 2 | 2'-MOE | 2'-MOE | 2'-MOE | H | H |
| 112 | 2 | 5 | 3 | 11 | 2 | 2'-MOE | 2'-MOE | 2'-MOE | H | H |
| 112 | 2 | 8 | 3 | 8 | 2 | 2'-MOE | 2'-MOE | 2'-MOE | H | H |
| 112 | 2 | 11 | 3 | 5 | 2 | 2'-MOE | 2'-MOE | 2'-MOE | H | H |
| 112 | 2 | 14 | 3 | 2 | 2 | 2'-MOE | 2'-MOE | 2'-MOE | H | H |
| 112 | 2 | 9 | 3 | 7 | 2 | 2'-MOE | 2'-MOE | 2'-MOE | H | H |
| 112 | 2 | 10 | 3 | 6 | 2 | 2'-MOE | 2'-MOE | 2'-MOE | H | H |
| 112 | 2 | 12 | 3 | 4 | 2 | 2'-MOE | 2'-MOE | 2'-MOE | H | H |
| 112 | 2 | 3 | 3 | 13 | 2 | 2'-MOE | 2'-MOE | 2'-MOE | H | H |
| 112 | 2 | 4 | 3 | 12 | 2 | 2'-MOE | 2'-MOE | 2'-MOE | H | H |
| 112 | 2 | 6 | 3 | 10 | 2 | 2'-MOE | 2'-MOE | 2'-MOE | H | H |
| 112 | 2 | 7 | 3 | 9 | 2 | 2'-MOE | 2'-MOE | 2'-MOE | H | H |
| 112 | 2 | 13 | 3 | 3 | 2 | 2'-MOE | 2'-MOE | 2'-MOE | H | H |
| 112 | 2 | 8 | 6 | 5 | 2 | 2'-MOE | 2'-MOE | 2'-MOE | H | H |
| 112 | 2 | 2 | 2 | 15 | 2 | 2'-MOE | 2'-MOE | 2'-MOE | H | H |
| 112 | 2 | 3 | 2 | 14 | 2 | 2'-MOE | 2'-MOE | 2'-MOE | H | H |
| 112 | 2 | 4 | 2 | 13 | 2 | 2'-MOE | 2'-MOE | 2'-MOE | H | H |
| 112 | 2 | 5 | 2 | 12 | 2 | 2'-MOE | 2'-MOE | 2'-MOE | H | H |
| 112 | 2 | 6 | 2 | 11 | 2 | 2'-MOE | 2'-MOE | 2'-MOE | H | H |
| 112 | 2 | 7 | 2 | 10 | 2 | 2'-MOE | 2'-MOE | 2'-MOE | H | H |
| 112 | 2 | 8 | 2 | 9 | 2 | 2'-MOE | 2'-MOE | 2'-MOE | H | H |
| 112 | 2 | 9 | 2 | 8 | 2 | 2'-MOE | 2'-MOE | 2'-MOE | H | H |
| 112 | 2 | 10 | 2 | 7 | 2 | 2'-MOE | 2'-MOE | 2'-MOE | H | H |
| 112 | 2 | 11 | 2 | 6 | 2 | 2'-MOE | 2'-MOE | 2'-MOE | H | H |
| 112 | 2 | 12 | 2 | 5 | 2 | 2'-MOE | 2'-MOE | 2'-MOE | H | H |
| 112 | 2 | 13 | 2 | 4 | 2 | 2'-MOE | 2'-MOE | 2'-MOE | H | H |
| 112 | 2 | 14 | 2 | 3 | 2 | 2'-MOE | 2'-MOE | 2'-MOE | H | H |
| 112 | 2 | 15 | 2 | 2 | 2 | 2'-MOE | 2'-MOE | 2'-MOE | H | H |

In certain embodiments, oligomeric compounds can have the following pairings of nucleotide sequence and formula I, as shown in Table 2, wherein each nucleoside is linked by phosphorothioate internucleoside linkages. In other embodiments, the examples of formula I shown in Table 2 are applied to any oligomeric compound comprising 22 linked nucleosides.

TABLE 2

| SEQ ID NO | n1 | n2 | n3 | n4 | n5 | Nu$_1$ | Nu$_3$ | Nu$_5$ | T$_1$ | T$_2$ |
|---|---|---|---|---|---|---|---|---|---|---|
| 1 | 2 | 18 | 0 | 0 | 2 | 2'-MOE | 2'-MOE | 2'-MOE | H | H |
| 1 | 2 | 2 | 3 | 13 | 2 | 2'-MOE | 2'-MOE | 2'-MOE | H | H |
| 1 | 2 | 5 | 3 | 10 | 2 | 2'-MOE | 2'-MOE | 2'-MOE | H | H |
| 1 | 2 | 8 | 3 | 7 | 2 | 2'-MOE | 2'-MOE | 2'-MOE | H | H |
| 1 | 2 | 11 | 3 | 4 | 2 | 2'-MOE | 2'-MOE | 2'-MOE | H | H |
| 1 | 2 | 9 | 3 | 6 | 2 | 2'-MOE | 2'-MOE | 2'-MOE | H | H |
| 1 | 2 | 10 | 3 | 5 | 2 | 2'-MOE | 2'-MOE | 2'-MOE | H | H |
| 1 | 2 | 12 | 3 | 3 | 2 | 2'-MOE | 2'-MOE | 2'-MOE | H | H |
| 1 | 2 | 3 | 3 | 12 | 2 | 2'-MOE | 2'-MOE | 2'-MOE | H | H |
| 1 | 2 | 4 | 3 | 11 | 2 | 2'-MOE | 2'-MOE | 2'-MOE | H | H |
| 1 | 2 | 6 | 3 | 9 | 2 | 2'-MOE | 2'-MOE | 2'-MOE | H | H |
| 1 | 2 | 7 | 3 | 8 | 2 | 2'-MOE | 2'-MOE | 2'-MOE | H | H |
| 1 | 2 | 13 | 3 | 2 | 2 | 2'-MOE | 2'-MOE | 2'-MOE | H | H |
| 1 | 2 | 8 | 6 | 4 | 2 | 2'-MOE | 2'-MOE | 2'-MOE | H | H |
| 1 | 2 | 2 | 2 | 14 | 2 | 2'-MOE | 2'-MOE | 2'-MOE | H | H |
| 1 | 2 | 3 | 2 | 13 | 2 | 2'-MOE | 2'-MOE | 2'-MOE | H | H |
| 1 | 2 | 4 | 2 | 12 | 2 | 2'-MOE | 2'-MOE | 2'-MOE | H | H |
| 1 | 2 | 5 | 2 | 11 | 2 | 2'-MOE | 2'-MOE | 2'-MOE | H | H |
| 1 | 2 | 6 | 2 | 10 | 2 | 2'-MOE | 2'-MOE | 2'-MOE | H | H |
| 1 | 2 | 7 | 2 | 9 | 2 | 2'-MOE | 2'-MOE | 2'-MOE | H | H |
| 1 | 2 | 8 | 2 | 8 | 2 | 2'-MOE | 2'-MOE | 2'-MOE | H | H |
| 1 | 2 | 9 | 2 | 7 | 2 | 2'-MOE | 2'-MOE | 2'-MOE | H | H |
| 1 | 2 | 10 | 2 | 6 | 2 | 2'-MOE | 2'-MOE | 2'-MOE | H | H |
| 1 | 2 | 11 | 2 | 5 | 2 | 2'-MOE | 2'-MOE | 2'-MOE | H | H |
| 1 | 2 | 12 | 2 | 4 | 2 | 2'-MOE | 2'-MOE | 2'-MOE | H | H |
| 1 | 2 | 13 | 2 | 3 | 2 | 2'-MOE | 2'-MOE | 2'-MOE | H | H |
| 1 | 2 | 14 | 2 | 2 | 2 | 2'-MOE | 2'-MOE | 2'-MOE | H | H |
| 2 | 2 | 18 | 0 | 0 | 2 | 2'-MOE | 2'-MOE | 2'-MOE | H | H |

TABLE 2-continued

| SEQ ID NO | n1 | n2 | n3 | n4 | n5 | Nu$_1$ | Nu$_3$ | Nu$_5$ | T$_1$ | T$_2$ |
|---|---|---|---|---|---|---|---|---|---|---|
| 2 | 2 | 2 | 3 | 13 | 2 | 2'-MOE | 2'-MOE | 2'-MOE | H | H |
| 2 | 2 | 5 | 3 | 10 | 2 | 2'-MOE | 2'-MOE | 2'-MOE | H | H |
| 2 | 2 | 8 | 3 | 7 | 2 | 2'-MOE | 2'-MOE | 2'-MOE | H | H |
| 2 | 2 | 11 | 3 | 4 | 2 | 2'-MOE | 2'-MOE | 2'-MOE | H | H |
| 2 | 2 | 9 | 3 | 6 | 2 | 2'-MOE | 2'-MOE | 2'-MOE | H | H |
| 2 | 2 | 10 | 3 | 5 | 2 | 2'-MOE | 2'-MOE | 2'-MOE | H | H |
| 2 | 2 | 12 | 3 | 3 | 2 | 2'-MOE | 2'-MOE | 2'-MOE | H | H |
| 2 | 2 | 3 | 3 | 12 | 2 | 2'-MOE | 2'-MOE | 2'-MOE | H | H |
| 2 | 2 | 4 | 3 | 11 | 2 | 2'-MOE | 2'-MOE | 2'-MOE | H | H |
| 2 | 2 | 6 | 3 | 9 | 2 | 2'-MOE | 2'-MOE | 2'-MOE | H | H |
| 2 | 2 | 7 | 3 | 8 | 2 | 2'-MOE | 2'-MOE | 2'-MOE | H | H |
| 2 | 2 | 13 | 3 | 2 | 2 | 2'-MOE | 2'-MOE | 2'-MOE | H | H |
| 2 | 2 | 8 | 6 | 4 | 2 | 2'-MOE | 2'-MOE | 2'-MOE | H | H |
| 2 | 2 | 2 | 2 | 14 | 2 | 2'-MOE | 2'-MOE | 2'-MOE | H | H |
| 2 | 2 | 3 | 2 | 13 | 2 | 2'-MOE | 2'-MOE | 2'-MOE | H | H |
| 2 | 2 | 4 | 2 | 12 | 2 | 2'-MOE | 2'-MOE | 2'-MOE | H | H |
| 2 | 2 | 5 | 2 | 11 | 2 | 2'-MOE | 2'-MOE | 2'-MOE | H | H |
| 2 | 2 | 6 | 2 | 10 | 2 | 2'-MOE | 2'-MOE | 2'-MOE | H | H |
| 2 | 2 | 7 | 2 | 9 | 2 | 2'-MOE | 2'-MOE | 2'-MOE | H | H |
| 2 | 2 | 8 | 2 | 8 | 2 | 2'-MOE | 2'-MOE | 2'-MOE | H | H |
| 2 | 2 | 9 | 2 | 7 | 2 | 2'-MOE | 2'-MOE | 2'-MOE | H | H |
| 2 | 2 | 10 | 2 | 6 | 2 | 2'-MOE | 2'-MOE | 2'-MOE | H | H |
| 2 | 2 | 11 | 2 | 5 | 2 | 2'-MOE | 2'-MOE | 2'-MOE | H | H |
| 2 | 2 | 12 | 2 | 4 | 2 | 2'-MOE | 2'-MOE | 2'-MOE | H | H |
| 2 | 2 | 13 | 2 | 3 | 2 | 2'-MOE | 2'-MOE | 2'-MOE | H | H |
| 2 | 2 | 14 | 2 | 2 | 2 | 2'-MOE | 2'-MOE | 2'-MOE | H | H |
| 6 | 2 | 18 | 0 | 0 | 2 | 2'-MOE | 2'-MOE | 2'-MOE | H | H |
| 6 | 2 | 2 | 3 | 13 | 2 | 2'-MOE | 2'-MOE | 2'-MOE | H | H |
| 6 | 2 | 5 | 3 | 10 | 2 | 2'-MOE | 2'-MOE | 2'-MOE | H | H |
| 6 | 2 | 8 | 3 | 7 | 2 | 2'-MOE | 2'-MOE | 2'-MOE | H | H |
| 6 | 2 | 11 | 3 | 4 | 2 | 2'-MOE | 2'-MOE | 2'-MOE | H | H |
| 6 | 2 | 9 | 3 | 6 | 2 | 2'-MOE | 2'-MOE | 2'-MOE | H | H |
| 6 | 2 | 10 | 3 | 5 | 2 | 2'-MOE | 2'-MOE | 2'-MOE | H | H |
| 6 | 2 | 12 | 3 | 3 | 2 | 2'-MOE | 2'-MOE | 2'-MOE | H | H |
| 6 | 2 | 3 | 3 | 12 | 2 | 2'-MOE | 2'-MOE | 2'-MOE | H | H |
| 6 | 2 | 4 | 3 | 11 | 2 | 2'-MOE | 2'-MOE | 2'-MOE | H | H |
| 6 | 2 | 6 | 3 | 9 | 2 | 2'-MOE | 2'-MOE | 2'-MOE | H | H |
| 6 | 2 | 7 | 3 | 8 | 2 | 2'-MOE | 2'-MOE | 2'-MOE | H | H |
| 6 | 2 | 13 | 3 | 2 | 2 | 2'-MOE | 2'-MOE | 2'-MOE | H | H |
| 6 | 2 | 8 | 6 | 4 | 2 | 2'-MOE | 2'-MOE | 2'-MOE | H | H |
| 6 | 2 | 2 | 2 | 14 | 2 | 2'-MOE | 2'-MOE | 2'-MOE | H | H |
| 6 | 2 | 3 | 2 | 13 | 2 | 2'-MOE | 2'-MOE | 2'-MOE | H | H |
| 6 | 2 | 4 | 2 | 12 | 2 | 2'-MOE | 2'-MOE | 2'-MOE | H | H |
| 6 | 2 | 5 | 2 | 11 | 2 | 2'-MOE | 2'-MOE | 2'-MOE | H | H |
| 6 | 2 | 6 | 2 | 10 | 2 | 2'-MOE | 2'-MOE | 2'-MOE | H | H |
| 6 | 2 | 7 | 2 | 9 | 2 | 2'-MOE | 2'-MOE | 2'-MOE | H | H |
| 6 | 2 | 8 | 2 | 8 | 2 | 2'-MOE | 2'-MOE | 2'-MOE | H | H |
| 6 | 2 | 9 | 2 | 7 | 2 | 2'-MOE | 2'-MOE | 2'-MOE | H | H |
| 6 | 2 | 10 | 2 | 6 | 2 | 2'-MOE | 2'-MOE | 2'-MOE | H | H |
| 6 | 2 | 11 | 2 | 5 | 2 | 2'-MOE | 2'-MOE | 2'-MOE | H | H |
| 6 | 2 | 12 | 2 | 4 | 2 | 2'-MOE | 2'-MOE | 2'-MOE | H | H |
| 6 | 2 | 13 | 2 | 3 | 2 | 2'-MOE | 2'-MOE | 2'-MOE | H | H |
| 6 | 2 | 14 | 2 | 2 | 2 | 2'-MOE | 2'-MOE | 2'-MOE | H | H |
| 20 | 2 | 18 | 0 | 0 | 2 | 2'-MOE | 2'-MOE | 2'-MOE | H | H |
| 20 | 2 | 2 | 3 | 13 | 2 | 2'-MOE | 2'-MOE | 2'-MOE | H | H |
| 20 | 2 | 5 | 3 | 10 | 2 | 2'-MOE | 2'-MOE | 2'-MOE | H | H |
| 20 | 2 | 8 | 3 | 7 | 2 | 2'-MOE | 2'-MOE | 2'-MOE | H | H |
| 20 | 2 | 11 | 3 | 4 | 2 | 2'-MOE | 2'-MOE | 2'-MOE | H | H |
| 20 | 2 | 9 | 3 | 6 | 2 | 2'-MOE | 2'-MOE | 2'-MOE | H | H |
| 20 | 2 | 10 | 3 | 5 | 2 | 2'-MOE | 2'-MOE | 2'-MOE | H | H |
| 20 | 2 | 12 | 3 | 3 | 2 | 2'-MOE | 2'-MOE | 2'-MOE | H | H |
| 20 | 2 | 3 | 3 | 12 | 2 | 2'-MOE | 2'-MOE | 2'-MOE | H | H |
| 20 | 2 | 4 | 3 | 11 | 2 | 2'-MOE | 2'-MOE | 2'-MOE | H | H |
| 20 | 2 | 6 | 3 | 9 | 2 | 2'-MOE | 2'-MOE | 2'-MOE | H | H |
| 20 | 2 | 7 | 3 | 8 | 2 | 2'-MOE | 2'-MOE | 2'-MOE | H | H |
| 20 | 2 | 13 | 3 | 2 | 2 | 2'-MOE | 2'-MOE | 2'-MOE | H | H |
| 20 | 2 | 8 | 6 | 4 | 2 | 2'-MOE | 2'-MOE | 2'-MOE | H | H |
| 20 | 2 | 2 | 2 | 14 | 2 | 2'-MOE | 2'-MOE | 2'-MOE | H | H |
| 20 | 2 | 3 | 2 | 13 | 2 | 2'-MOE | 2'-MOE | 2'-MOE | H | H |
| 20 | 2 | 4 | 2 | 12 | 2 | 2'-MOE | 2'-MOE | 2'-MOE | H | H |
| 20 | 2 | 5 | 2 | 11 | 2 | 2'-MOE | 2'-MOE | 2'-MOE | H | H |
| 20 | 2 | 6 | 2 | 10 | 2 | 2'-MOE | 2'-MOE | 2'-MOE | H | H |
| 20 | 2 | 7 | 2 | 9 | 2 | 2'-MOE | 2'-MOE | 2'-MOE | H | H |
| 20 | 2 | 8 | 2 | 8 | 2 | 2'-MOE | 2'-MOE | 2'-MOE | H | H |
| 20 | 2 | 9 | 2 | 7 | 2 | 2'-MOE | 2'-MOE | 2'-MOE | H | H |
| 20 | 2 | 10 | 2 | 6 | 2 | 2'-MOE | 2'-MOE | 2'-MOE | H | H |
| 20 | 2 | 11 | 2 | 5 | 2 | 2'-MOE | 2'-MOE | 2'-MOE | H | H |
| 20 | 2 | 12 | 2 | 4 | 2 | 2'-MOE | 2'-MOE | 2'-MOE | H | H |
| 20 | 2 | 13 | 2 | 3 | 2 | 2'-MOE | 2'-MOE | 2'-MOE | H | H |
| 20 | 2 | 14 | 2 | 2 | 2 | 2'-MOE | 2'-MOE | 2'-MOE | H | H |
| 45 | 2 | 18 | 0 | 0 | 2 | 2'-MOE | 2'-MOE | 2'-MOE | H | H |
| 45 | 2 | 2 | 3 | 13 | 2 | 2'-MOE | 2'-MOE | 2'-MOE | H | H |
| 45 | 2 | 5 | 3 | 10 | 2 | 2'-MOE | 2'-MOE | 2'-MOE | H | H |
| 45 | 2 | 8 | 3 | 7 | 2 | 2'-MOE | 2'-MOE | 2'-MOE | H | H |
| 45 | 2 | 11 | 3 | 4 | 2 | 2'-MOE | 2'-MOE | 2'-MOE | H | H |
| 45 | 2 | 9 | 3 | 6 | 2 | 2'-MOE | 2'-MOE | 2'-MOE | H | H |
| 45 | 2 | 10 | 3 | 5 | 2 | 2'-MOE | 2'-MOE | 2'-MOE | H | H |
| 45 | 2 | 12 | 3 | 3 | 2 | 2'-MOE | 2'-MOE | 2'-MOE | H | H |
| 45 | 2 | 3 | 3 | 12 | 2 | 2'-MOE | 2'-MOE | 2'-MOE | H | H |
| 45 | 2 | 4 | 3 | 11 | 2 | 2'-MOE | 2'-MOE | 2'-MOE | H | H |
| 45 | 2 | 6 | 3 | 9 | 2 | 2'-MOE | 2'-MOE | 2'-MOE | H | H |
| 45 | 2 | 7 | 3 | 8 | 2 | 2'-MOE | 2'-MOE | 2'-MOE | H | H |
| 45 | 2 | 13 | 3 | 2 | 2 | 2'-MOE | 2'-MOE | 2'-MOE | H | H |
| 45 | 2 | 8 | 6 | 4 | 2 | 2'-MOE | 2'-MOE | 2'-MOE | H | H |
| 45 | 2 | 2 | 2 | 14 | 2 | 2'-MOE | 2'-MOE | 2'-MOE | H | H |
| 45 | 2 | 3 | 2 | 13 | 2 | 2'-MOE | 2'-MOE | 2'-MOE | H | H |
| 45 | 2 | 4 | 2 | 12 | 2 | 2'-MOE | 2'-MOE | 2'-MOE | H | H |
| 45 | 2 | 5 | 2 | 11 | 2 | 2'-MOE | 2'-MOE | 2'-MOE | H | H |
| 45 | 2 | 6 | 2 | 10 | 2 | 2'-MOE | 2'-MOE | 2'-MOE | H | H |
| 45 | 2 | 7 | 2 | 9 | 2 | 2'-MOE | 2'-MOE | 2'-MOE | H | H |
| 45 | 2 | 8 | 2 | 8 | 2 | 2'-MOE | 2'-MOE | 2'-MOE | H | H |
| 45 | 2 | 9 | 2 | 7 | 2 | 2'-MOE | 2'-MOE | 2'-MOE | H | H |
| 45 | 2 | 10 | 2 | 6 | 2 | 2'-MOE | 2'-MOE | 2'-MOE | H | H |
| 45 | 2 | 11 | 2 | 5 | 2 | 2'-MOE | 2'-MOE | 2'-MOE | H | H |
| 45 | 2 | 12 | 2 | 4 | 2 | 2'-MOE | 2'-MOE | 2'-MOE | H | H |
| 45 | 2 | 13 | 2 | 3 | 2 | 2'-MOE | 2'-MOE | 2'-MOE | H | H |
| 45 | 2 | 14 | 2 | 2 | 2 | 2'-MOE | 2'-MOE | 2'-MOE | H | H |
| 60 | 2 | 18 | 0 | 0 | 2 | 2'-MOE | 2'-MOE | 2'-MOE | H | H |
| 60 | 2 | 2 | 3 | 13 | 2 | 2'-MOE | 2'-MOE | 2'-MOE | H | H |
| 60 | 2 | 5 | 3 | 10 | 2 | 2'-MOE | 2'-MOE | 2'-MOE | H | H |
| 60 | 2 | 8 | 3 | 7 | 2 | 2'-MOE | 2'-MOE | 2'-MOE | H | H |
| 60 | 2 | 11 | 3 | 4 | 2 | 2'-MOE | 2'-MOE | 2'-MOE | H | H |
| 60 | 2 | 9 | 3 | 6 | 2 | 2'-MOE | 2'-MOE | 2'-MOE | H | H |
| 60 | 2 | 10 | 3 | 5 | 2 | 2'-MOE | 2'-MOE | 2'-MOE | H | H |
| 60 | 2 | 12 | 3 | 3 | 2 | 2'-MOE | 2'-MOE | 2'-MOE | H | H |
| 60 | 2 | 3 | 3 | 12 | 2 | 2'-MOE | 2'-MOE | 2'-MOE | H | H |
| 60 | 2 | 4 | 3 | 11 | 2 | 2'-MOE | 2'-MOE | 2'-MOE | H | H |
| 60 | 2 | 6 | 3 | 9 | 2 | 2'-MOE | 2'-MOE | 2'-MOE | H | H |
| 60 | 2 | 7 | 3 | 8 | 2 | 2'-MOE | 2'-MOE | 2'-MOE | H | H |
| 60 | 2 | 13 | 3 | 2 | 2 | 2'-MOE | 2'-MOE | 2'-MOE | H | H |
| 60 | 2 | 8 | 6 | 4 | 2 | 2'-MOE | 2'-MOE | 2'-MOE | H | H |
| 60 | 2 | 2 | 2 | 14 | 2 | 2'-MOE | 2'-MOE | 2'-MOE | H | H |
| 60 | 2 | 3 | 2 | 13 | 2 | 2'-MOE | 2'-MOE | 2'-MOE | H | H |
| 60 | 2 | 4 | 2 | 12 | 2 | 2'-MOE | 2'-MOE | 2'-MOE | H | H |
| 60 | 2 | 5 | 2 | 11 | 2 | 2'-MOE | 2'-MOE | 2'-MOE | H | H |
| 60 | 2 | 6 | 2 | 10 | 2 | 2'-MOE | 2'-MOE | 2'-MOE | H | H |
| 60 | 2 | 7 | 2 | 9 | 2 | 2'-MOE | 2'-MOE | 2'-MOE | H | H |
| 60 | 2 | 8 | 2 | 8 | 2 | 2'-MOE | 2'-MOE | 2'-MOE | H | H |
| 60 | 2 | 9 | 2 | 7 | 2 | 2'-MOE | 2'-MOE | 2'-MOE | H | H |
| 60 | 2 | 10 | 2 | 6 | 2 | 2'-MOE | 2'-MOE | 2'-MOE | H | H |
| 60 | 2 | 11 | 2 | 5 | 2 | 2'-MOE | 2'-MOE | 2'-MOE | H | H |
| 60 | 2 | 12 | 2 | 4 | 2 | 2'-MOE | 2'-MOE | 2'-MOE | H | H |
| 60 | 2 | 13 | 2 | 3 | 2 | 2'-MOE | 2'-MOE | 2'-MOE | H | H |
| 60 | 2 | 14 | 2 | 2 | 2 | 2'-MOE | 2'-MOE | 2'-MOE | H | H |
| 80 | 2 | 18 | 0 | 0 | 2 | 2'-MOE | 2'-MOE | 2'-MOE | H | H |
| 80 | 2 | 2 | 3 | 13 | 2 | 2'-MOE | 2'-MOE | 2'-MOE | H | H |
| 80 | 2 | 5 | 3 | 10 | 2 | 2'-MOE | 2'-MOE | 2'-MOE | H | H |
| 80 | 2 | 8 | 3 | 7 | 2 | 2'-MOE | 2'-MOE | 2'-MOE | H | H |
| 80 | 2 | 11 | 3 | 4 | 2 | 2'-MOE | 2'-MOE | 2'-MOE | H | H |
| 80 | 2 | 9 | 3 | 6 | 2 | 2'-MOE | 2'-MOE | 2'-MOE | H | H |
| 80 | 2 | 10 | 3 | 5 | 2 | 2'-MOE | 2'-MOE | 2'-MOE | H | H |
| 80 | 2 | 12 | 3 | 3 | 2 | 2'-MOE | 2'-MOE | 2'-MOE | H | H |
| 80 | 2 | 3 | 3 | 12 | 2 | 2'-MOE | 2'-MOE | 2'-MOE | H | H |
| 80 | 2 | 4 | 3 | 11 | 2 | 2'-MOE | 2'-MOE | 2'-MOE | H | H |
| 80 | 2 | 6 | 3 | 9 | 2 | 2'-MOE | 2'-MOE | 2'-MOE | H | H |
| 80 | 2 | 7 | 3 | 8 | 2 | 2'-MOE | 2'-MOE | 2'-MOE | H | H |
| 80 | 2 | 13 | 3 | 2 | 2 | 2'-MOE | 2'-MOE | 2'-MOE | H | H |
| 80 | 2 | 8 | 6 | 4 | 2 | 2'-MOE | 2'-MOE | 2'-MOE | H | H |
| 80 | 2 | 2 | 2 | 14 | 2 | 2'-MOE | 2'-MOE | 2'-MOE | H | H |
| 80 | 2 | 3 | 2 | 13 | 2 | 2'-MOE | 2'-MOE | 2'-MOE | H | H |
| 80 | 2 | 4 | 2 | 12 | 2 | 2'-MOE | 2'-MOE | 2'-MOE | H | H |
| 80 | 2 | 5 | 2 | 11 | 2 | 2'-MOE | 2'-MOE | 2'-MOE | H | H |
| 80 | 2 | 6 | 2 | 10 | 2 | 2'-MOE | 2'-MOE | 2'-MOE | H | H |
| 80 | 2 | 7 | 2 | 9 | 2 | 2'-MOE | 2'-MOE | 2'-MOE | H | H |

TABLE 2-continued

| SEQ ID NO | n1 | n2 | n3 | n4 | n5 | $Nu_1$ | $Nu_3$ | $Nu_5$ | $T_1$ | $T_2$ |
|---|---|---|---|---|---|---|---|---|---|---|
| 80 | 2 | 8 | 2 | 8 | 2 | 2'-MOE | 2'-MOE | 2'-MOE | H | H |
| 80 | 2 | 9 | 2 | 7 | 2 | 2'-MOE | 2'-MOE | 2'-MOE | H | H |
| 80 | 2 | 10 | 2 | 6 | 2 | 2'-MOE | 2'-MOE | 2'-MOE | H | H |
| 80 | 2 | 11 | 2 | 5 | 2 | 2'-MOE | 2'-MOE | 2'-MOE | H | H |
| 80 | 2 | 12 | 2 | 4 | 2 | 2'-MOE | 2'-MOE | 2'-MOE | H | H |
| 80 | 2 | 13 | 2 | 3 | 2 | 2'-MOE | 2'-MOE | 2'-MOE | H | H |
| 80 | 2 | 14 | 2 | 2 | 2 | 2'-MOE | 2'-MOE | 2'-MOE | H | H |
| 100 | 2 | 18 | 0 | 0 | 2 | 2'-MOE | 2'-MOE | 2'-MOE | H | H |
| 100 | 2 | 2 | 3 | 13 | 2 | 2'-MOE | 2'-MOE | 2'-MOE | H | H |
| 100 | 2 | 5 | 3 | 10 | 2 | 2'-MOE | 2'-MOE | 2'-MOE | H | H |
| 100 | 2 | 8 | 3 | 7 | 2 | 2'-MOE | 2'-MOE | 2'-MOE | H | H |
| 100 | 2 | 11 | 3 | 4 | 2 | 2'-MOE | 2'-MOE | 2'-MOE | H | H |
| 100 | 2 | 9 | 3 | 6 | 2 | 2'-MOE | 2'-MOE | 2'-MOE | H | H |
| 100 | 2 | 10 | 3 | 5 | 2 | 2'-MOE | 2'-MOE | 2'-MOE | H | H |
| 100 | 2 | 12 | 3 | 3 | 2 | 2'-MOE | 2'-MOE | 2'-MOE | H | H |
| 100 | 2 | 3 | 3 | 12 | 2 | 2'-MOE | 2'-MOE | 2'-MOE | H | H |
| 100 | 2 | 4 | 3 | 11 | 2 | 2'-MOE | 2'-MOE | 2'-MOE | H | H |
| 100 | 2 | 6 | 3 | 9 | 2 | 2'-MOE | 2'-MOE | 2'-MOE | H | H |
| 100 | 2 | 7 | 3 | 8 | 2 | 2'-MOE | 2'-MOE | 2'-MOE | H | H |
| 100 | 2 | 13 | 3 | 2 | 2 | 2'-MOE | 2'-MOE | 2'-MOE | H | H |
| 100 | 2 | 8 | 6 | 4 | 2 | 2'-MOE | 2'-MOE | 2'-MOE | H | H |
| 100 | 2 | 2 | 2 | 14 | 2 | 2'-MOE | 2'-MOE | 2'-MOE | H | H |
| 100 | 2 | 3 | 2 | 13 | 2 | 2'-MOE | 2'-MOE | 2'-MOE | H | H |
| 100 | 2 | 4 | 2 | 12 | 2 | 2'-MOE | 2'-MOE | 2'-MOE | H | H |
| 100 | 2 | 5 | 2 | 11 | 2 | 2'-MOE | 2'-MOE | 2'-MOE | H | H |
| 100 | 2 | 6 | 2 | 10 | 2 | 2'-MOE | 2'-MOE | 2'-MOE | H | H |
| 100 | 2 | 7 | 2 | 9 | 2 | 2'-MOE | 2'-MOE | 2'-MOE | H | H |
| 100 | 2 | 8 | 2 | 8 | 2 | 2'-MOE | 2'-MOE | 2'-MOE | H | H |
| 100 | 2 | 9 | 2 | 7 | 2 | 2'-MOE | 2'-MOE | 2'-MOE | H | H |
| 100 | 2 | 10 | 2 | 6 | 2 | 2'-MOE | 2'-MOE | 2'-MOE | H | H |
| 100 | 2 | 11 | 2 | 5 | 2 | 2'-MOE | 2'-MOE | 2'-MOE | H | H |
| 100 | 2 | 12 | 2 | 4 | 2 | 2'-MOE | 2'-MOE | 2'-MOE | H | H |
| 100 | 2 | 13 | 2 | 3 | 2 | 2'-MOE | 2'-MOE | 2'-MOE | H | H |
| 100 | 2 | 14 | 2 | 2 | 2 | 2'-MOE | 2'-MOE | 2'-MOE | H | H |
| 103 | 2 | 18 | 0 | 0 | 2 | 2'-MOE | 2'-MOE | 2'-MOE | H | H |
| 103 | 2 | 2 | 3 | 13 | 2 | 2'-MOE | 2'-MOE | 2'-MOE | H | H |
| 103 | 2 | 5 | 3 | 10 | 2 | 2'-MOE | 2'-MOE | 2'-MOE | H | H |
| 103 | 2 | 8 | 3 | 7 | 2 | 2'-MOE | 2'-MOE | 2'-MOE | H | H |
| 103 | 2 | 11 | 3 | 4 | 2 | 2'-MOE | 2'-MOE | 2'-MOE | H | H |
| 103 | 2 | 9 | 3 | 6 | 2 | 2'-MOE | 2'-MOE | 2'-MOE | H | H |
| 103 | 2 | 10 | 3 | 5 | 2 | 2'-MOE | 2'-MOE | 2'-MOE | H | H |
| 103 | 2 | 12 | 3 | 3 | 2 | 2'-MOE | 2'-MOE | 2'-MOE | H | H |
| 103 | 2 | 3 | 3 | 12 | 2 | 2'-MOE | 2'-MOE | 2'-MOE | H | H |
| 103 | 2 | 4 | 3 | 11 | 2 | 2'-MOE | 2'-MOE | 2'-MOE | H | H |
| 103 | 2 | 6 | 3 | 9 | 2 | 2'-MOE | 2'-MOE | 2'-MOE | H | H |
| 103 | 2 | 7 | 3 | 8 | 2 | 2'-MOE | 2'-MOE | 2'-MOE | H | H |
| 103 | 2 | 13 | 3 | 2 | 2 | 2'-MOE | 2'-MOE | 2'-MOE | H | H |
| 103 | 2 | 8 | 6 | 4 | 2 | 2'-MOE | 2'-MOE | 2'-MOE | H | H |
| 103 | 2 | 2 | 2 | 14 | 2 | 2'-MOE | 2'-MOE | 2'-MOE | H | H |
| 103 | 2 | 3 | 2 | 13 | 2 | 2'-MOE | 2'-MOE | 2'-MOE | H | H |
| 103 | 2 | 4 | 2 | 12 | 2 | 2'-MOE | 2'-MOE | 2'-MOE | H | H |
| 103 | 2 | 5 | 2 | 11 | 2 | 2'-MOE | 2'-MOE | 2'-MOE | H | H |
| 103 | 2 | 6 | 2 | 10 | 2 | 2'-MOE | 2'-MOE | 2'-MOE | H | H |
| 103 | 2 | 7 | 2 | 9 | 2 | 2'-MOE | 2'-MOE | 2'-MOE | H | H |
| 103 | 2 | 8 | 2 | 8 | 2 | 2'-MOE | 2'-MOE | 2'-MOE | H | H |
| 103 | 2 | 9 | 2 | 7 | 2 | 2'-MOE | 2'-MOE | 2'-MOE | H | H |
| 103 | 2 | 10 | 2 | 6 | 2 | 2'-MOE | 2'-MOE | 2'-MOE | H | H |
| 103 | 2 | 11 | 2 | 5 | 2 | 2'-MOE | 2'-MOE | 2'-MOE | H | H |
| 103 | 2 | 12 | 2 | 4 | 2 | 2'-MOE | 2'-MOE | 2'-MOE | H | H |
| 103 | 2 | 13 | 2 | 3 | 2 | 2'-MOE | 2'-MOE | 2'-MOE | H | H |
| 103 | 2 | 14 | 2 | 2 | 2 | 2'-MOE | 2'-MOE | 2'-MOE | H | H |
| 113 | 2 | 18 | 0 | 0 | 2 | 2'-MOE | 2'-MOE | 2'-MOE | H | H |
| 113 | 2 | 2 | 3 | 13 | 2 | 2'-MOE | 2'-MOE | 2'-MOE | H | H |
| 113 | 2 | 5 | 3 | 10 | 2 | 2'-MOE | 2'-MOE | 2'-MOE | H | H |
| 113 | 2 | 8 | 3 | 7 | 2 | 2'-MOE | 2'-MOE | 2'-MOE | H | H |
| 113 | 2 | 11 | 3 | 4 | 2 | 2'-MOE | 2'-MOE | 2'-MOE | H | H |
| 113 | 2 | 9 | 3 | 6 | 2 | 2'-MOE | 2'-MOE | 2'-MOE | H | H |
| 113 | 2 | 10 | 3 | 5 | 2 | 2'-MOE | 2'-MOE | 2'-MOE | H | H |
| 113 | 2 | 12 | 3 | 3 | 2 | 2'-MOE | 2'-MOE | 2'-MOE | H | H |
| 113 | 2 | 3 | 3 | 12 | 2 | 2'-MOE | 2'-MOE | 2'-MOE | H | H |
| 113 | 2 | 4 | 3 | 11 | 2 | 2'-MOE | 2'-MOE | 2'-MOE | H | H |
| 113 | 2 | 6 | 3 | 9 | 2 | 2'-MOE | 2'-MOE | 2'-MOE | H | H |
| 113 | 2 | 7 | 3 | 8 | 2 | 2'-MOE | 2'-MOE | 2'-MOE | H | H |
| 113 | 2 | 13 | 3 | 2 | 2 | 2'-MOE | 2'-MOE | 2'-MOE | H | H |
| 113 | 2 | 8 | 6 | 4 | 2 | 2'-MOE | 2'-MOE | 2'-MOE | H | H |
| 113 | 2 | 2 | 2 | 14 | 2 | 2'-MOE | 2'-MOE | 2'-MOE | H | H |
| 113 | 2 | 3 | 2 | 13 | 2 | 2'-MOE | 2'-MOE | 2'-MOE | H | H |
| 113 | 2 | 4 | 2 | 12 | 2 | 2'-MOE | 2'-MOE | 2'-MOE | H | H |
| 113 | 2 | 5 | 2 | 11 | 2 | 2'-MOE | 2'-MOE | 2'-MOE | H | H |
| 113 | 2 | 6 | 2 | 10 | 2 | 2'-MOE | 2'-MOE | 2'-MOE | H | H |
| 113 | 2 | 7 | 2 | 9 | 2 | 2'-MOE | 2'-MOE | 2'-MOE | H | H |
| 113 | 2 | 8 | 2 | 8 | 2 | 2'-MOE | 2'-MOE | 2'-MOE | H | H |
| 113 | 2 | 9 | 2 | 7 | 2 | 2'-MOE | 2'-MOE | 2'-MOE | H | H |
| 113 | 2 | 10 | 2 | 6 | 2 | 2'-MOE | 2'-MOE | 2'-MOE | H | H |
| 113 | 2 | 11 | 2 | 5 | 2 | 2'-MOE | 2'-MOE | 2'-MOE | H | H |
| 113 | 2 | 12 | 2 | 4 | 2 | 2'-MOE | 2'-MOE | 2'-MOE | H | H |
| 113 | 2 | 13 | 2 | 3 | 2 | 2'-MOE | 2'-MOE | 2'-MOE | H | H |
| 113 | 2 | 14 | 2 | 2 | 2 | 2'-MOE | 2'-MOE | 2'-MOE | H | H |

In certain embodiments, oligomeric compounds can have the following pairings of nucleotide sequence and formula I, as shown in Table 3, wherein each nucleoside is linked by phosphorothioate internucleoside linkages. In other embodiments, the examples of formula I shown in Table 3 are applied to any oligomeric compound comprising 21 linked nucleosides.

TABLE 3

| SEQ ID NO | n1 | n2 | n3 | n4 | n5 | $Nu_1$ | $Nu_3$ | $Nu_5$ | $T_1$ | $T_2$ |
|---|---|---|---|---|---|---|---|---|---|---|
| 463 | 2 | 17 | 0 | 0 | 2 | 2'-MOE | 2'-MOE | 2'-MOE | H | H |
| 463 | 2 | 2 | 3 | 12 | 2 | 2'-MOE | 2'-MOE | 2'-MOE | H | H |
| 463 | 2 | 5 | 3 | 9 | 2 | 2'-MOE | 2'-MOE | 2'-MOE | H | H |
| 463 | 2 | 8 | 3 | 6 | 2 | 2'-MOE | 2'-MOE | 2'-MOE | H | H |
| 463 | 2 | 11 | 3 | 3 | 2 | 2'-MOE | 2'-MOE | 2'-MOE | H | H |
| 463 | 2 | 9 | 3 | 5 | 2 | 2'-MOE | 2'-MOE | 2'-MOE | H | H |
| 463 | 2 | 10 | 3 | 4 | 2 | 2'-MOE | 2'-MOE | 2'-MOE | H | H |
| 463 | 2 | 12 | 3 | 2 | 2 | 2'-MOE | 2'-MOE | 2'-MOE | H | H |
| 463 | 2 | 3 | 3 | 11 | 2 | 2'-MOE | 2'-MOE | 2'-MOE | H | H |
| 463 | 2 | 4 | 3 | 10 | 2 | 2'-MOE | 2'-MOE | 2'-MOE | H | H |
| 463 | 2 | 6 | 3 | 8 | 2 | 2'-MOE | 2'-MOE | 2'-MOE | H | H |
| 463 | 2 | 7 | 3 | 7 | 2 | 2'-MOE | 2'-MOE | 2'-MOE | H | H |
| 463 | 2 | 8 | 6 | 3 | 2 | 2'-MOE | 2'-MOE | 2'-MOE | H | H |
| 463 | 2 | 2 | 2 | 13 | 2 | 2'-MOE | 2'-MOE | 2'-MOE | H | H |
| 463 | 2 | 3 | 2 | 12 | 2 | 2'-MOE | 2'-MOE | 2'-MOE | H | H |
| 463 | 2 | 4 | 2 | 11 | 2 | 2'-MOE | 2'-MOE | 2'-MOE | H | H |
| 463 | 2 | 5 | 2 | 10 | 2 | 2'-MOE | 2'-MOE | 2'-MOE | H | H |
| 463 | 2 | 6 | 2 | 9 | 2 | 2'-MOE | 2'-MOE | 2'-MOE | H | H |
| 463 | 2 | 7 | 2 | 8 | 2 | 2'-MOE | 2'-MOE | 2'-MOE | H | H |
| 463 | 2 | 8 | 2 | 7 | 2 | 2'-MOE | 2'-MOE | 2'-MOE | H | H |
| 463 | 2 | 9 | 2 | 6 | 2 | 2'-MOE | 2'-MOE | 2'-MOE | H | H |
| 463 | 2 | 10 | 2 | 5 | 2 | 2'-MOE | 2'-MOE | 2'-MOE | H | H |
| 463 | 2 | 11 | 2 | 4 | 2 | 2'-MOE | 2'-MOE | 2'-MOE | H | H |
| 463 | 2 | 12 | 2 | 3 | 2 | 2'-MOE | 2'-MOE | 2'-MOE | H | H |
| 463 | 2 | 13 | 2 | 2 | 2 | 2'-MOE | 2'-MOE | 2'-MOE | H | H |

In certain embodiments, oligomeric compounds can have the following pairings of nucleotide sequence and formula I, as shown in Table 4, wherein each nucleoside is linked by phosphorothioate internucleoside linkages. In other embodiments, the examples of formula I shown in Table 4 are applied to any oligomeric compound comprising 20 linked nucleosides.

TABLE 4

| SEQ ID NO | n1 | n2 | n3 | n4 | n5 | $Nu_1$ | $Nu_3$ | $Nu_5$ | $T_1$ | $T_2$ |
|---|---|---|---|---|---|---|---|---|---|---|
| 64 | 2 | 16 | 0 | 0 | 2 | 2'-MOE | 2'-MOE | 2'-MOE | H | H |
| 64 | 2 | 2 | 3 | 11 | 2 | 2'-MOE | 2'-MOE | 2'-MOE | H | H |
| 64 | 2 | 5 | 3 | 8 | 2 | 2'-MOE | 2'-MOE | 2'-MOE | H | H |
| 64 | 2 | 8 | 3 | 5 | 2 | 2'-MOE | 2'-MOE | 2'-MOE | H | H |
| 64 | 2 | 11 | 3 | 2 | 2 | 2'-MOE | 2'-MOE | 2'-MOE | H | H |
| 64 | 2 | 9 | 3 | 4 | 2 | 2'-MOE | 2'-MOE | 2'-MOE | H | H |
| 64 | 2 | 10 | 3 | 3 | 2 | 2'-MOE | 2'-MOE | 2'-MOE | H | H |
| 64 | 2 | 3 | 3 | 10 | 2 | 2'-MOE | 2'-MOE | 2'-MOE | H | H |

TABLE 4-continued

| SEQ ID NO | n1 | n2 | n3 | n4 | n5 | Nu$_1$ | Nu$_3$ | Nu$_5$ | T$_1$ | T$_2$ |
|---|---|---|---|---|---|---|---|---|---|---|
| 64 | 2 | 4 | 3 | 9 | 2 | 2'-MOE | 2'-MOE | 2'-MOE | H | H |
| 64 | 2 | 6 | 3 | 7 | 2 | 2'-MOE | 2'-MOE | 2'-MOE | H | H |
| 64 | 2 | 7 | 3 | 6 | 2 | 2'-MOE | 2'-MOE | 2'-MOE | H | H |
| 64 | 2 | 8 | 6 | 2 | 2 | 2'-MOE | 2'-MOE | 2'-MOE | H | H |
| 64 | 2 | 2 | 2 | 12 | 2 | 2'-MOE | 2'-MOE | 2'-MOE | H | H |
| 64 | 2 | 3 | 2 | 11 | 2 | 2'-MOE | 2'-MOE | 2'-MOE | H | H |
| 64 | 2 | 4 | 2 | 10 | 2 | 2'-MOE | 2'-MOE | 2'-MOE | H | H |
| 64 | 2 | 5 | 2 | 9 | 2 | 2'-MOE | 2'-MOE | 2'-MOE | H | H |
| 64 | 2 | 6 | 2 | 8 | 2 | 2'-MOE | 2'-MOE | 2'-MOE | H | H |
| 64 | 2 | 7 | 2 | 7 | 2 | 2'-MOE | 2'-MOE | 2'-MOE | H | H |
| 64 | 2 | 8 | 2 | 6 | 2 | 2'-MOE | 2'-MOE | 2'-MOE | H | H |
| 64 | 2 | 9 | 2 | 5 | 2 | 2'-MOE | 2'-MOE | 2'-MOE | H | H |
| 64 | 2 | 10 | 2 | 4 | 2 | 2'-MOE | 2'-MOE | 2'-MOE | H | H |
| 64 | 2 | 11 | 2 | 3 | 2 | 2'-MOE | 2'-MOE | 2'-MOE | H | H |
| 64 | 2 | 12 | 2 | 2 | 2 | 2'-MOE | 2'-MOE | 2'-MOE | H | H |

In certain embodiments, oligomeric compounds can have the following pairings of nucleotide sequence and formula I, as shown in Table 5, wherein each nucleoside is linked by phosphorothioate internucleoside linkages. In other embodiments, the examples of formula I shown in Table 5 are applied to any oligomeric compound comprising 24 linked nucleosides.

TABLE 5

| SEQ ID NO | n1 | n2 | n3 | n4 | n5 | Nu$_1$ | Nu$_3$ | Nu$_5$ | T$_1$ | T$_2$ |
|---|---|---|---|---|---|---|---|---|---|---|
| 47 | 2 | 20 | 0 | 0 | 2 | 2'-MOE | 2'-MOE | 2'-MOE | H | H |
| 47 | 2 | 2 | 3 | 15 | 2 | 2'-MOE | 2'-MOE | 2'-MOE | H | H |
| 47 | 2 | 5 | 3 | 12 | 2 | 2'-MOE | 2'-MOE | 2'-MOE | H | H |
| 47 | 2 | 8 | 3 | 9 | 2 | 2'-MOE | 2'-MOE | 2'-MOE | H | H |
| 47 | 2 | 11 | 3 | 6 | 2 | 2'-MOE | 2'-MOE | 2'-MOE | H | H |
| 47 | 2 | 14 | 3 | 3 | 2 | 2'-MOE | 2'-MOE | 2'-MOE | H | H |
| 47 | 2 | 9 | 3 | 8 | 2 | 2'-MOE | 2'-MOE | 2'-MOE | H | H |
| 47 | 2 | 10 | 3 | 7 | 2 | 2'-MOE | 2'-MOE | 2'-MOE | H | H |
| 47 | 2 | 12 | 3 | 5 | 2 | 2'-MOE | 2'-MOE | 2'-MOE | H | H |
| 47 | 2 | 3 | 3 | 14 | 2 | 2'-MOE | 2'-MOE | 2'-MOE | H | H |
| 47 | 2 | 4 | 3 | 13 | 2 | 2'-MOE | 2'-MOE | 2'-MOE | H | H |
| 47 | 2 | 6 | 3 | 11 | 2 | 2'-MOE | 2'-MOE | 2'-MOE | H | H |
| 47 | 2 | 7 | 3 | 10 | 2 | 2'-MOE | 2'-MOE | 2'-MOE | H | H |
| 47 | 2 | 13 | 3 | 4 | 2 | 2'-MOE | 2'-MOE | 2'-MOE | H | H |
| 47 | 2 | 8 | 6 | 6 | 2 | 2'-MOE | 2'-MOE | 2'-MOE | H | H |
| 47 | 2 | 2 | 2 | 16 | 2 | 2'-MOE | 2'-MOE | 2'-MOE | H | H |
| 47 | 2 | 3 | 2 | 15 | 2 | 2'-MOE | 2'-MOE | 2'-MOE | H | H |
| 47 | 2 | 4 | 2 | 14 | 2 | 2'-MOE | 2'-MOE | 2'-MOE | H | H |
| 47 | 2 | 5 | 2 | 13 | 2 | 2'-MOE | 2'-MOE | 2'-MOE | H | H |
| 47 | 2 | 6 | 2 | 12 | 2 | 2'-MOE | 2'-MOE | 2'-MOE | H | H |
| 47 | 2 | 7 | 2 | 11 | 2 | 2'-MOE | 2'-MOE | 2'-MOE | H | H |
| 47 | 2 | 8 | 2 | 10 | 2 | 2'-MOE | 2'-MOE | 2'-MOE | H | H |
| 47 | 2 | 9 | 2 | 9 | 2 | 2'-MOE | 2'-MOE | 2'-MOE | H | H |
| 47 | 2 | 10 | 2 | 8 | 2 | 2'-MOE | 2'-MOE | 2'-MOE | H | H |
| 47 | 2 | 11 | 2 | 7 | 2 | 2'-MOE | 2'-MOE | 2'-MOE | H | H |
| 47 | 2 | 12 | 2 | 6 | 2 | 2'-MOE | 2'-MOE | 2'-MOE | H | H |
| 47 | 2 | 13 | 2 | 5 | 2 | 2'-MOE | 2'-MOE | 2'-MOE | H | H |
| 47 | 2 | 14 | 2 | 4 | 2 | 2'-MOE | 2'-MOE | 2'-MOE | H | H |
| 47 | 2 | 15 | 3 | 2 | 2 | 2'-MOE | 2'-MOE | 2'-MOE | H | H |
| 47 | 2 | 15 | 2 | 3 | 2 | 2'-MOE | 2'-MOE | 2'-MOE | H | H |
| 47 | 2 | 16 | 2 | 2 | 2 | 2'-MOE | 2'-MOE | 2'-MOE | H | H |

In further embodiments, in addition to having a configuration as described above, the oligomeric compounds are described as having each of Nu$_1$, Nu$_3$, and Nu$_5$ as stabilizing nucleotides. In certain embodiments, oligomeric compounds can have a motif as described above, wherein each of Nu$_1$, Nu$_3$, and Nu$_5$ is 2'-MOE. In further embodiments, each internucleoside linkage is a phosphorothioate internucleoside linkage.

Oligomeric compounds of the invention, having a contiguous sequence of linked nucleosides, can also be described by the following formula:

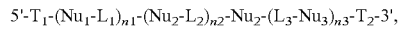

5'-T$_1$-(Nu$_1$-L$_1$)$_{n1}$-(Nu$_2$-L$_2$)$_{n2}$-Nu$_2$-(L$_3$-Nu$_3$)$_{n3}$-T$_2$-3', wherein:

each Nu$_1$ and Nu$_3$ is, independently, a stabilizing nucleoside;

at least 10 Nu$_2$ are β-D-2'-deoxy-2'-fluororibofuranosyl nucleosides;

each L$_1$, L$_2$ and L$_3$ is, independently, an internucleoside linking group;

each T$_1$ and T$_2$ is, independently, H, a hydroxyl protecting group, an optionally linked conjugate group or a capping group;

n$_1$ is from 0 to about 3;

n$_2$ is from about 14 to about 22;

n$_3$ is from 0 to about 3; and provided that if n$_1$ is 0 then T$_1$ is not H or a hydroxyl protecting group, and if n$_3$ is 0, then T$_2$ is not H or a hydroxyl protecting group.

Oligomeric compounds can have a formula described herein applied to a contiguous nucleotide sequence selected from SEQ ID NOs 1-470.

A "stabilizing modification" means providing enhanced stability, in the presence of nucleases, relative to that provided by 2'-deoxynucleosides linked by phosphodiester internucleoside linkages. Thus, such modifications provide "enhanced nuclease stability" to oligomeric compounds. Stabilizing modifications include at least stabilizing nucleosides and stabilizing internucleoside linkage groups.

The term "stability enhancing nucleoside" or "stabilizing nucleoside" is meant to include all manner of nucleosides known to those skilled in the art to provide enhanced nuclease stability of oligomeric compounds. In one embodiment, stabilizing nucleosides can be 2'-modified nucleosides. Examples of such stability enhancing 2'-modified nucleosides include, but are not limited to, 2'-OCH3,2'-methoxyethoxy(2'-O—CH$_2$CH$_2$OCH$_3$, Martin et al., Helv. Chim. Acta, 1995, 78, 486-504), a bicyclic sugar modified nucleoside, 2'-dimethylaminooxyethoxy(O(CH$_2$)$_2$ON(CH$_3$)$_2$, 2'-dimethylaminoethoxyethoxy(2'-O—CH$_2$—O—CH$_2$—N(CH$_3$)$_2$), methoxy (—O—CH$_3$), aminopropoxy (—OCH$_2$CH$_2$CH$_2$NH$_2$), allyl (—CH$_2$—CH=CH$_2$), —O-allyl(—O—CH$_2$—CH=CH$_2$) and 2'-acetamido(2'-O—CH$_2$C(=O)NR1R1 wherein each R1 is independently, H or C1-C1 alkyl.

Representative U.S. patents that teach the preparation of such 2'-modified nucleosides include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with this application, and each of which is herein incorporated by reference.

In one aspect the present invention provides oligomeric compounds having at least one stability enhancing internucleoside linkage. The term "stability enhancing internucleoside linkage" or "stabilizing internucleoside linking group" is meant to include all manner of internucleoside linkages that provide enhanced nuclease stability to oligomeric compounds relative to that provided by phosphodiester internucleoside linkages. Thus, stability enhancing internucleoside linkages are linkages other than phosphodiester internucleoside linkages. An example of such stability enhancing internucleoside linkages includes, but is not limited to, phosphorothioates internucleoside linkages.

Representative U.S. patents that teach the preparation of stability enhancing internucleoside linkages include, but are not limited to, U.S. Pat. Nos. 3,687,808; 5,286,717; 5,587, 361; 5,672,697; 5,489,677; 5,663,312; 5,646,269 and 5,677,439, each of which is herein incorporated by reference.

Exemplary oligomeric compounds provided herein comprise a nucleobase sequence that is substantially complementary, including 100% complementary to a small non-coding RNA. As such, exemplary oligomeric compounds are capable of hybridizing with and modulating the activity of a small non-coding RNA. In one embodiment, the small non-coding RNA to which an oligomeric compound hybridizes is a miRNA.

Further provided are methods for modulating the levels, expression, processing or function of a small non-coding RNA. Oligomeric compounds of the invention can modulate the levels, expression or function of small non-coding RNAs by hybridizing to a nucleic acid comprising or encoding a small non-coding RNA nucleic acid target resulting in alteration of normal function. In one embodiment, alteration of normal function is due to the ability of the oligomeric compound to facilitate destruction of the small non-coding RNA through cleavage, by sequestration, or by sterically occlusion. In other embodiments, the oligomeric compounds stably hybridize to the small non-coding RNA and prevent it from hybrizing to, and regulating the activity of, its normal cellular target. In one embodiment, the modulating comprises inhibiting the function of a miRNA.

The methods provided herein include methods of inhibiting miRNA activity in an animal, comprising contacting an animal with an oligomeric compound having potent activity and improved therapeutic index. In some embodiments, the oligomeric compound comprises at least 18 contiguous nucleotides of a sequence selected from SEQ ID NOs 1-470. In other embodiments, oligomeric compounds comprise at least 20 contiguous nucleotides of sequence selected from SEQ ID NOs 1-470. In other embodiments, oligomeric compounds consist of a sequence selected from SEQ ID NOs 1-470.

Embodiments provided herein include methods of reducing cholesterol in an animal comprising administering an oligomeric compound having potent activity and improved therapeutic index to an animal, particularly a human. In one embodiment, miR-122a is targeted with an oligomeric compound of the invention.

Provided herein are oligomeric compounds and compositions containing the same, wherein the oligomeric compound includes one or more modifications that render the compound capable of supporting modulation of the levels, expression or function of the small non-coding RNA by a degradation or cleavage mechanism.

Also provided herein are oligomeric compounds and compositions containing the same wherein the oligomeric compound includes one or more modifications that render the compound capable of blocking or interfering with the levels, expression or function of one or more small non-coding RNAs by steric occlusion.

"Therapeutic index" means the ratio of the dose of an oligomeric compound which produces an undesired effect to the dose which causes desired effects. In the context of the present disclosure, an oligomeric compound exhibits an "improved therapeutic index" when activity is retained, but undesired effects are reduced or absent. For example, an oligomeric compound having an improved therapeutic index retains the ability to inhibit miRNA activity without resulting in undesired effects such as immunostimulatory activity, or, at least, without resulting in undesired effects to a degree that would prohibit administration of the compound.

As used herein, the term "small non-coding RNA" is used to encompass, without limitation, a polynucleotide molecule ranging from 17 to 29 nucleotides in length. In one embodiment, a small non-coding RNA is a miRNA (also known as microRNAs, Mirs, miRs, mirs, and mature miRNAs.

As used herein, the term "miRNA precursor" is used to encompass any longer nucleic acid sequence from which a miRNA is derived and may include, without limitation, primary RNA transcripts, pri-miRNAs, and pre-miRNAs.

As used herein, the term "miRNA family" refers to a plurality of miRNAs that are related by nucleotide sequence. Thus, the members of an miRNA family are herein termed "related miRNAs". Each member of a miRNA family shares an identical seed sequence. As used herein, the term "seed sequence" refers to nucleotides 2 to 6 or 2 to 7 from the 5'-end of a mature miRNA sequence. Examples of miRNA families are known in the art and include, but are not limited to, the let-7 family (having 9 miRNAs), the miR-15 family (comprising miR-15a, miR-15b, miR-16-1, and miR-195), and the miR-181 family (comprising miR-181a, miR-181b, and miR-181c).

As used herein, the terms "target nucleic acid," "target RNA," "target RNA transcript" or "nucleic acid target" are used to encompass any nucleic acid capable of being targeted including, without limitation, RNA. In a one embodiment, the target nucleic acids are non-coding sequences including, but not limited to, miRNAs and miRNA precursors. In a preferred embodiment, the target nucleic acid is an miRNA, which may also be referred to as the miRNA target. An oligomeric compound is "targeted to a miRNA" when an oligomeric compound comprises a sequence substantially, including 100% complementary to a miRNA.

In the context of the present disclosure, "modulation of function" means an alteration in the function or activity of the small non-coding RNA or an alteration in the function of any cellular component with which the small non-coding RNA has an association or downstream effect. In one embodiment, modulation of function is an inhibition of the activity of a small non-coding RNA.

As used herein, "modulation" and "modulation of expression" mean either an increase (stimulation) or a decrease (inhibition) in the amount, or levels, of a small non-coding RNA, nucleic acid target, an RNA or protein associated with a small non-coding RNA, or a downstream target of the small non-coding RNA (e.g., a mRNA representing a protein-coding nucleic acid that is regulated by a small non-coding RNA). Inhibition is a suitable form of modulation and small non-coding RNA is a suitable nucleic acid target. Small non-coding RNAs whose levels can be modulated include miRNA and miRNA precursors.

Oligomeric Compounds

In the context of the present invention, the term "oligomeric compound(s)" refers to polymeric structures which are capable of hybridizing to at least a region of a nucleic acid target. In one embodiment, a nucleic acid target is a miRNA. The term "oligomeric compound" includes, but is not limited to, compounds comprising oligonucleotides, oligonucleosides, oligonucleotide analogs, oligonucleotide mimetics and combinations of these. Oligomeric compounds also include, but are not limited to, antisense oligomeric compounds, antisense oligonucleotides, siRNAs, alternate splicers, primers, probes and other compounds that hybridize to at least a portion of the target nucleic acid. An oligomeric compound or oligonucleotide is "antisense" when its nucleobase sequence, written in the 5' to 3' direction, comprises the reverse complement of the corresponding region of a target nucleic acid.

In general, an oligomeric compound comprises a backbone of linked monomeric subunits where each linked monomeric subunit is directly or indirectly attached to a heterocyclic base moiety. The linkages joining the monomeric subunits, the sugar moieties or sugar surrogates and the heterocyclic base moieties can be independently modified giving rise to a plurality of motifs for the resulting oligomeric compounds including, without limitation, uniform, hemimers, gapmers and positionally modified oliomeric compounds.

Modified oligomeric compounds are often preferred over native forms because of desirable properties such as, for example, enhanced cellular uptake, enhanced affinity for a nucleic acid target, increased stability in the presence of nucleases and increased ability to modulate the function of a small non-coding RNA. As used herein, the term "modification" includes substitution and/or any change from a starting or natural oligomeric compound, such as an oligonucleotide. Modifications to oligomeric compounds encompass substitutions or changes to internucleoside linkages, sugar moieties, or base moieties, such as those described below.

Oligomeric compounds are routinely prepared linearly but can be joined or otherwise prepared to be circular and may also include branching. Separate oligomeric compounds can hybridize to form double stranded compounds that can be blunt-ended or may include overhangs on one or both termini.

The oligomeric compounds in accordance with this invention can comprise from about 12 to about 50 monomeric subunits (i.e. from about 12 to about 50 linked nucleosides). One of ordinary skill in the art will appreciate that the invention embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 subunits in length.

In one embodiment, the oligomeric compounds of the invention are 15 to 30 monomeric subunits in length, as exemplified above.

In one embodiment, the oligomeric compounds of the invention are 17 to 29 subunits in length, as exemplified herein.

In one embodiment, the oligomeric compounds of the invention are 18 to 26 monomeric subunits in length, as exemplified above.

In one embodiment, the oligomeric compounds of the invention are 19, 20, 21, 22, 23, or 24 subunits in length, or alternatively the oligomeric compounds of the invention range from 19 to 24 subunits in length.

In one embodiment, the oligomeric compounds of the invention are 21, 22, 23, or 24 subunits in length, or alternatively the oligomeric compounds of the invention range from 21 to 24 subunits in length.

As used herein, the term "about" means±5% of the variable thereafter.

Hybridization

In the context of this invention, "hybridization" means the pairing of complementary strands of oligomeric compounds. In the present invention, the mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An oligomeric compound is "specifically hybridizable" when there is a sufficient degree of complementarity to avoid non-specific binding of the oligomeric compound to non-target nucleic acid sequences under conditions in which specific hybridization is desired, i.e., under physiological conditions in the case of in vivo assays or therapeutic treatment, and under standard assay conditions in the case of in vitro assays. An oligomeric compound that is specifically hybridizable to a nucleic acid target interferes with the normal function of the nucleic acid target and consequently alters the activity, disrupts the function, or modulates the level of the target nucleic acid, and The phrase "stringent hybridization conditions" or "stringent conditions" refers to conditions under which an oligomeric compound of the invention will specifically hybridize to its nucleic acid target. Stringent conditions are sequence-dependent and will vary with different circumstances and in the present context; "stringent conditions" under which oligomeric compounds hybridize to a nucleic acid target are determined by the nature and composition of the oligomeric compounds and the assays in which they are being investigated. One having ordinary skill in the art will understand variability in the experimental protocols and be able to determine when conditions are optimal for stringent hybridization with minimal non-specific hybridization events.

"Complementarity," as used herein, refers to the capacity for precise pairing of one nucleobase with another. For example, if a monomeric subunit at a certain position of an oligomeric compound is capable of hydrogen bonding with a monomeric subunit at a certain position of a nucleic acid target, then the position is considered to be a complementary position. Conversely, a position is considered "non-complementary" when monomeric subunits are not capable of hydrogen bonding. The oligomeric compound and the target nucleic acid are "substantially complementary" to each other when a sufficient number of complementary positions in each molecule are occupied by monomeric subunits that can hydrogen bond with each other. Thus, the term "substantially complementary" is used to indicate a sufficient degree of precise pairing over a sufficient number of monomeric subunits such that stable and specific binding occurs between the oligomeric compound and a target nucleic acid. The terms "substantially complementary" and "sufficiently complementary" are herein used interchangeably.

An oligomeric compound need not be 100% complementary to that of its target nucleic acid to be specifically hybridizable. Moreover, an oligomeric compound may hybridize over one or more segments such that intervening or adjacent segments are not involved in the hybridization (e.g., a bulge, a loop structure or a hairpin structure). A "non-complementary nucleobase" means a nucleobase of an antisense oligonucleotide that is unable to undergo precise base pairing with a nucleobase at a corresponding position in a target nucleic acid. In some embodiments there are non-complementary positions, also known as "mismatches", between the oligomeric compound and the target nucleic acid, and such non-complementary positions may be tolerated between an oligomeric compound and the target nucleic acid provided that the oligomeric compound remains substantially complementary to the target nucleic acid. As used herein, the terms "non-complementary" and "mismatch" are used interchangeably. Up to 3 mismatches are often tolerated in an oligomeric compound without causing a significant decrease in the ability of the oligomeric compound to modulate the activity of the target nucleic acid. In some embodiments, mismatches are preferred outside of the region of the oligomeric compound which is complementary to the seed sequence of the target miRNA. In a preferred embodiment, the oligomeric compound contains 0, 1 or 2 mismatches to the target miRNA. In a more preferred embodiment, the oligomeric compound contains at most 1 mismatch to the target miRNA.

An oligomeric compound and a nucleic acid target are "fully complementary" to each other when each nucleobase of an oligomeric compound is capable of undergoing base-pairing with corresponding positions in a nucleic acid target. As used herein, the term "full length complementarity" means that an oligomeric compound comprises a contiguous sequence of nucleosides with the same length as the target miRNA and is fully complementary to the target miRNA (for example if the miRNA is 22 nucleotides in length, an oligomeric compound with full length complementary oligomeric compound is also 22 nucleotides in length). In some embodiments, an oligomeric compound has full length complementarity to a target miRNA.

As used herein the term "essentially full length complementarity" is intended to include full length complementarity between the two strands as well as up to 3 mismatches between the oligomeric compound and the target miRNA such that the oligomeric compound is still capable of hybridizing with the target miRNA and the function of the oligomeric compound is not substantially impaired. The term is also meant to include oligomeric compounds with a truncation or expansion with respect to the length of target miRNA by up to 6 nucleosides, the truncation or expansion being a deletion or addition of nucleosides to either the 3' or 5' end of the oligomeric compound or at both the 3' and 5' end of the oligomeric compound. In certain embodiments, the oligomeric compound is truncated by 1 or 2 nucleosides compared with the length of the target miRNA. As a non-limiting example, if the target miRNA is 22 nucleotides in length, the oligomeric compound which has essentially full length complementarity may be 20 or 21 nucleotides in length. In a preferred embodiment, the oligomeric compound is truncated by 1 nucleotide on either the 3' or 5' end of the oligomeric compound.

In some embodiments, oligomeric compounds comprise at least at least 85%, at least 90%, or at least 95% sequence complementarity to a target region within the target nucleic acid. In other embodiments, oligomeric compounds are 100% complementary to a nucleic acid target.

Oligomeric compounds, or portions thereof, may have a defined percent identity to an oligomeric compound. This identity may be over the entire length of the oligomeric compound, or in a portion of the oligomeric compound (e.g., nucleobases 1-20 of a 27-mer may be compared to a 20-mer to determine percent identity of the oligomeric compound to the oligonucleotide). An oligomeric compound need not have an identical sequence to those described herein to function similarly to the oligomeric compounds described herein. Shortened (i.e., deleted, and therefore non-identical) versions of oligonucleotides taught herein, or non-identical (i.e., one base replaced with another) versions of the oligonucleotides taught herein fall within the scope of the invention. Percent identity is calculated according to the number of bases that are identical to the oligomeric compound to which it is being compared. The non-identical bases may be adjacent to each other, dispersed through out the oligonucleotide, or both.

A "target region" is defined as a portion of the target nucleic acid having at least one identifiable sequence, structure, function, or characteristic. "Target segments" are defined as smaller or sub-portions of target regions within a target nucleic acid. "Sites," as used in the present invention, are defined as specific positions within a target nucleic acid. A "5' target site" is the 5'-most nucleotide to which an oligomeric compound is complementary. A "3' target site" is the 3'-most nucleotide to which an oligomeric compound is complementary. In some embodiments, a target segment is a full length miRNA. In other embodiments, a target segment is the seed sequence of the target miRNA. As used herein, the term "seed sequence" is defined as nucleobases 2 through 7 at the 5'-end of a miRNA.

The locations on the target nucleic acid to which compounds and compositions of the invention hybridize are herein referred to as "suitable target segments." As used herein the term "suitable target segment" is defined as at least a 6-nucleobase portion of a target region to which an oligomeric compound is targeted. In one embodiment, a suitable target segment of the target miRNA is the seed sequence of the miRNA.

The oligomeric compounds of the invention can be in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or proteins to effect modulation of the levels, expression or function of the target nucleic acid.

One non-limiting example of such a protein is the Drosha RNase III enzyme. Drosha is a nuclear enzyme that processes long primary RNA transcripts (pri-miRNAs) from approximately 70 to 450 nucleotides in length into pre-miRNAs (from about 50 to about 80 nucleotides in length) which are exported from the nucleus to encounter the human Dicer enzyme which then processes pre-miRNAs into miRNAs.

A further non-limiting example involves the enzymes of the RISC complex. Use of the RISC complex to effect cleavage of RNA targets thereby greatly enhances the efficiency of oligonucleotide-mediated inhibition of gene expression. Similar roles have been postulated for other ribonucleases such as those in the RNase III and ribonuclease L family of enzymes.

Oligomeric Compound Modifications

As is known in the art, a nucleoside is a base-sugar combination. The base (or nucleobase) portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the unmodified oligonucleotide structure, the phosphate groups are commonly referred to as forming the internucleoside linkages of the oligonucleotide. The unmodified internucleoside linkage of RNA and DNA is a 3' to 5' phosphodiester linkage.

In the context of this invention, the term "unmodified oligonucleotide" refers generally to an oligomer or polymer of ribonucleic acid (RNA) or deoxyribonucleic acid (DNA). This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases. The term "oligonucleotide" can be used to refer to unmodified oligonucleotides or oligonucleotide analogs.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts. In addition to the modifications described above, the nucleosides of the oligomeric compounds of the invention can have a variety of other modifications.

Modified Internucleoside Linking Groups

Specific examples of oligomeric compounds include oligonucleotides containing modified, i.e. non-naturally occurring internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases.

Oligomeric compounds of the invention can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

One suitable phosphorus-containing modified internucleoside linkage is the phosphorothioate internucleoside linkage. A number of other modified oligonucleotide backbones (internucleoside linkages) are known in the art and may be useful in the context of this invention.

Representative U.S. patents that teach the preparation of phosphorus-containing internucleoside linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,6975,625,050, 5,489,677, and 5,602,240 each of which is herein incorporated by reference.

Modified oligonucleoside backbones (internucleoside linkages) that do not include a phosphorus atom therein have internucleoside linkages that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having amide backbones; and others, including those having mixed N, O, S and $CH_2$ component parts.

Representative U.S. patents that teach the preparation of the above non-phosphorous-containing oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Oligomeric compounds can also include oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring with for example a morpholino ring, is also referred to in the art as being a sugar surrogate. The heterocyclic base moiety or a modified heterocyclic base moiety is maintained for hybridization with an appropriate target nucleic acid. Oligonucleotide mimetics can include oligomeric compounds such as peptide nucleic acids (PNA) and cyclohexenyl nucleic acids (known as CeNA, see Wang et al., J. Am. Chem. Soc., 2000, 122, 8595-8602) Representative U.S. patents that teach the preparation of oligonucleotide mimetics include, but are not limited to, U.S. Pat. Nos. 5,539,082; 5,714,331; and 5,719, 262, each of which is herein incorporated by reference. Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Another oligonucleotide mimetic has been reported wherein the furanosyl ring has been replaced by a cyclobutyl moiety.

Modified Sugar Moieties

Oligomeric compounds of the invention can also contain one or more modified or substituted sugar moieties. The base moieties are maintained for hybridization with an appropriate nucleic acid target compound. Sugar modifications can impart nuclease stability, binding affinity or some other beneficial biological property to the oligomeric compounds. Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. A large number of sugar modifications are known in the art, sugars modified at the 2' position and those which have a bridge between any 2 atoms of the sugar (such that the sugar is bicyclic) are particularly useful in this invention. Examples of sugar modifications useful in this invention include, but are not limited to compounds comprising a sugar substituent group selected from: OH; F; O-, S-, or N-alkyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are: 2-methoxyethoxy (also known as 2'-O-methoxyethyl, 2'-MOE, or 2'-$OCH_2CH_2OCH_3$), 2'-O-methyl(2'-O—$CH_3$), 2'-fluoro (2'-F) or bicyclic sugar modified nucleosides having a bridging group connecting the 4' carbon atom to the 2' carbon atom wherein example bridge groups include —$CH_2$—O—, —$(CH_2)_2$—O— or —$CH_2$—N($R_3$)—O— wherein $R_3$ is H or $C_1$-$C_{12}$ alkyl.

In one embodiment, oligomeric compounds include one or more nucleosides having a substituent group at the 2'-position. Examples of 2'-sugar substituent groups useful in this invention include, but are not limited to: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nNH_2$, $O(CH_2)_nCH_3$, $O(CH_2)_nONH_2$, $OCH_2C(=O)N(H)CH_3$ and $O(CH_2)_nONRCH_2)_nCH_3h$, where n and m are from 1 to about 10. Other 2'-sugar substituent groups include: $C_1$ to $C_{10}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

One modification that imparts increased nuclease resistance and a very high binding affinity to nucleotides is the 2'-MOE side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

2'-Sugar substituent groups may be in the arabino (up) position or ribo (down) position. One 2'-arabino modification is 2'-F. Similar modifications can also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative sugar substituents groups are disclosed in U.S. Pat. No. 6,172,209 entitled "Capped 2'-Oxyethoxy Oligonucleotides," hereby incorporated by reference in its entirety.

Representative cyclic sugar substituent groups are disclosed in U.S. Pat. No. 6,271,358 entitled "RNA Targeted 2'-Oligomeric compounds that are Conformationally Preorganized," hereby incorporated by reference in its entirety.

Representative guanidino substituent groups are disclosed in U.S. Pat. No. 6,593,466 entitled "Functionalized Oligomers," hereby incorporated by reference in its entirety.

Representative acetamido substituent groups are disclosed in U.S. Pat. No. 6,147,200 which is hereby incorporated by reference in its entirety.

Another group of modifications includes nucleosides having sugar moieties that are bicyclic thereby locking the sugar conformational geometry. Such modifications may impart nuclease stability, binding affinity or some other beneficial biological property to the oligomeric compounds. The most studied of these nucleosides is a bicyclic sugar moiety modified nucleoside having a 4'-$CH_2$—O-2' bridge. This bridge attaches under the sugar as shown forcing the sugar ring into a locked 3'-endo conformation geometry. The alpha-L nucleoside has also been reported wherein the linkage is above the ring and the heterocyclic base is in the alpha rather than the beta-conformation (see U.S. patent application Publication No.: Application 2003/0087230). The xylo analog has also been prepared (see U.S. Patent Application Publication No.: 2003/0082807). Another bicyclic sugar modified nucleoside having similar properties to the 4'-$CH_2$—O-2' bridged nucleoside has one added methylene group in the bridge 4'-$(CH_2)_2$—O-2' (Kaneko et al., U.S. Patent Application Publication No.: US 2002/0147332, Singh et al., Chem. Commun., 1998, 4, 455-456, also see U.S. Pat. Nos. 6,268,490 and 6,670,461 and U.S. Patent Application Publication No.: US 2003/0207841). Oligomeric compounds incorporating these bicyclic sugar modified nucleosides (4'-$(CH_2)_{1(or 2)}$—O-2') display very high duplex thermal stabilities with complementary DNA and RNA (Tm=+3 to +10 C), stability towards 3'-exonucleolytic degradation and good solubility properties. The synthesis and preparation of the bicyclic sugar modified monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630; WO 98/39352 and WO 99/14226).

Other bicyclic sugar modified nucleoside analogs such as the 4'-$CH_2$—S-2' analog have also been prepared (Kumar et al., Bioorg. Med. Chem. Lett., 1998, 8, 2219-2222). Preparation of other bicyclic sugar analogs containing oligodeoxyribonucleotide duplexes as substrates for nucleic acid polymerases has also been described (Wengel et al., PCT International Application WO 98-DK393 19980914).

Nucleobase Modifications

Oligomeric compounds of the invention can also contain one or more nucleobase (often referred to in the art simply as "base") modifications or substitutions which are structurally distinguishable from, yet functionally interchangeable with, naturally occurring or synthetic unmodified nucleobases. Such nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Heterocyclic base moieties can also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2 aminopropyladenine, 5-propynyluracil and 5-propynylcytosine.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs.

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov, et al., *Nucleosides and Nucleotides*, 1997, 16, 1837-1846), 1,3-diazaphenothiazine-2-one ($R_{10}$=S, $R_{11}$-$R_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one ($R_{10}$=O, $R_{11}$-$R_{14}$=F) (Wang, J.; Lin, K.-Y., Matteucci, M. Tetrahedron Lett. 1998, 39, 8385-8388). When incorporated into oligonucleotides, these base modifications were shown to hybridize with complementary guanine and the latter was also shown to hybridize with adenine and to enhance helical thermal stability by extended stacking interactions (also see U.S. Patent Application Publication 20030207804 and U.S. Patent Application Publication 20030175906, both of which are incorporated herein by reference in their entirety).

Helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Tricyclic heterocyclic compounds and methods of using them that are amenable to the present invention are disclosed in U.S. Pat. No. 6,028,183, and U.S. Pat. No. 6,007,992, the contents of both are incorporated herein in their entirety.

The enhanced binding affinity of the phenoxazine derivatives together with their sequence specificity makes them valuable nucleobase analogs for the development of more potent antisense-based drugs. The activity enhancement was even more pronounced in case of G-clamp, as a single substitution was shown to significantly improve the in vitro potency of a 20mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Patent Application Publication 20030158403, each of which is incorporated herein by reference in its entirety.

Certain nucleobase substitutions, including 5-methylcytosinse substitutions, are particularly useful for increasing the binding affinity of the oligonucleotides of the invention. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Conjugated Oligomeric Compounds

One substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, carbohydrates, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety and a variety of others known in the art.

Furthermore, the oligomeric compounds of the invention can have one or more moieties bound or conjugated, which facilitates the active or passive transport, localization, or compartmentalization of the oligomeric compound. Cellular localization includes, but is not limited to, localization to within the nucleus, the nucleolus, or the cytoplasm. Compartmentalization includes, but is not limited to, any directed movement of the oligonucleotides of the invention to a cellular compartment including the nucleus, nucleolus, mitochondrion, or imbedding into a cellular membrane. Furthermore, the oligomeric compounds of the invention comprise one or more conjugate moieties which facilitate posttranscriptional modification.

Conjugate groups can be attached to various positions of an oligomeric compound directly or via an optional linking group. The term linking group is intended to include all groups amenable to attachment of a conjugate group to an oligomeric compound. Linking groups are bivalent groups useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glyol or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted C2-C10 alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl. Further representative linking groups are disclosed for example in WO 94/01550 and WO 94/01550.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications can protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. For double-stranded oligomeric compounds, the cap may be present at either or both termini of either strand. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitolnucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; amino hexyl phosphate; 3'-phosphate; 3'-phosphorothioate; phosphorodithioate; or bridging or non-bridging methylphosphonate moiety (see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide; carbocyclic nucleotide; 5'-amino-alkyl phosphate; 1,3-di-amino-2-propyl phosphate, 3-aminopropyl phosphate; 6-aminohexyl phosphate; 1,2-aminododecyl phosphate; hydroxypropyl phosphate; 1,5-anhydrohexitolnucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Oligomeric Compound Chemical Motifs

Oligomeric compounds can have chemically modified subunits arranged in specific orientations along their length. A "chemical motif" is defined as the arrangement of chemical modifications throughout an oligomeric compound In certain embodiments, oligomeric compounds of the invention are uniformly modified. As used herein, in a "uniformly modified" oligomeric compound a chemical modification of a sugar, base, internucleoside linkage, or combination thereof, is applied to each subunit of the oligomeric compound. In one embodiment, each sugar moiety of a uniformly modified oligomeric compound is modified. In other embodiments, each internucleoside linkage of a uniformly modified oligomeric compound is modified. In further embodiments, each sugar and each internucleoside linkage of uniformly modified oligomeric compounds bears a modification. Examples of uniformly modified oligomeric compounds include, but are not limited to, uniform 2'-MOE sugar moieties; uniform 2'-MOE and uniform phosphorothioate backbone; uniform 2'-OMe; uniform 2'-OMe and uniform phosphorothioate backbone; uniform 2'-F; uniform 2'-F and uniform phosphorothioate backbone; uniform phosphorothioate backbone; uniform deoxynucleotides; uniform ribonucleotides; uniform phosphorothioate backbone; and combinations thereof.

As used herein the term "positionally modified motif" is meant to include a sequence of uniformly sugar modified nucleosides wherein the sequence is interrupted by two or more regions comprising from 1 to about 8 sugar modified nucleosides wherein internal regions are generally from 1 to about 6 or from 1 to about 4. The positionally modified motif includes internal regions of sugar modified nucleoside and can also include one or both termini. Each particular sugar modification within a region of sugar modified nucleosides essentially uniform. The nucleotides of regions are distinguished by differing sugar modifications. Positionally modified motifs are not determined by the nucleobase sequence or the location or types of internucleoside linkages. The term positionally modified oligomeric compound includes many different specific substitution patterns. A number of these substitution patterns have been prepared and tested in compositions. In one embodiment the positionally modified oligomeric compounds may comprise phosphodiester internucleotide linkages, phosphorothioate internucleotide linkages, or a combination of phosphodiester and phosphorothioate internucleotide linkages.

In some embodiments, positionally modified oligomeric compounds include oligomeric compounds having clusters of a first modification interspersed with a second modification, as follows 5'-MMmmMmMMMmmmmMMMMmmmmm-3'; and 5'-MMmMMmMMmMMmMMmMMmMM-mMM-3'; wherein "M" represent the first modification, and "m" represents the second modification. In one embodiment, "M" is 2'-MOE and "m" is a bicyclic sugar modified nucleoside having a 4'-(CH$_2$)—O-2' where n is 1 or 2. In other embodiments, "M" is 2'-MOE and "m" is 2'-F. In other embodiments, "M" is 2'-OMe and "m" is 2'-F.

In some embodiment, oligomeric compounds are chimeric oligomeric compounds. "Chimeric oligomeric compounds" or "chimeras" are oligomeric compounds that at least 2 chemically distinct regions, each made up of at least one monomer unit, i.e., a nucleotide or nucleoside in the case of a nucleic acid based oligomeric compound. Methods of synthesizing chimeric oligonucleotides are well known in the art.

In certain embodiments, chimeric oligomeric compounds are gapmer oligomeric compounds. A "gapmer" means an oligomeric compound having contiguous sequence of nucleosides that are divided into 3 regions, an internal region (also referred to as a "gap" or "gap segment") which is flanked by two external regions (referred to as "wing" or "wing segment"). The internal and external regions are differentiated by sugar moieties, internucleoside linkages, or a combination thereof. The types of sugar moieties that are used to differentiate the regions of a gapmer oligomeric compound include β-D-ribonucleosides, β-D-deoxyribonucleosides, or 2'-modified nucleosides disclosed herein, including, without limitation, 2'-MOE, 2'-fluoro, 2'-O—CH$_3$, and bicyclic sugar modified nucleosides. In one embodiment, each region is uniformly modified. In another embodiment, the nucleosides of the internal region uniform sugar moieties that are different than the sugar moieties in an external region. In one non-limiting example, the gap is uniformly comprised of a first 2'-modified nucleoside and each of the wings is uniformly comprised of a second 2'-modified nucleoside.

Gapmer oligomeric compounds are further defined as being either "symmetric" or "asymmetric". A gapmer having the same uniform sugar modification in each of the wings is termed a "symmetric gapmer oligomeric compound." A gapmer having different uniform modifications in each wing is termed an "asymmetric gapmer oligomeric compound." In one embodiment, gapmer oligomeric compounds such as these can have, for example, both wings comprising 2'-MOE modified nucleosides (symmetric gapmer) and a gap comprising β-D-ribonucleosides or β-D-deoxyribonucleosides. In another embodiment, a symmetric gapmer can have both wings comprising 2'-MOE modified nucleosides and a gap comprising 2'-modified nucleosides other than 2'-MOE modified nucleosides. Asymmetric gapmer oligomeric compounds, for example, can have one wing comprising 2'-OCH$_3$ modified nucleosides and the other wing comprising 2'-MOE modified nucleosides with the internal region (gap) comprising β-D-ribonucleosides, β-D-deoxyribonucleosides or 2'-modified nucleosides that are other than 2'-MOE or 2'-OCH3 modified nucleosides. These gapmer oligomeric compounds may comprise phosphodiester internucleotide linkages, phosphorothioate internucleotide linkages, or a combination of phosphodiester and phosphorothioate internucleotide linkages.

In some embodiments, each wing of a gapmer oligomeric compounds comprises the same number of subunits. In other embodiments, one wing of a gapmer oligomeric compound comprises a different number of subunits than the other wing of a gapmer oligomeric compound. In one embodiment, the wings of gapmer oligomeric compounds have, independently, from 1 to about 3 nucleosides. Suitable wings comprise from 2 to about 3 nucleosides. In one embodiment, the wings can comprise 2 nucleosides. In another embodiment, the 5'-wing can comprise 1 or 2 nucleosides and the 3'-wing can comprise 2 or 3 nucleosides. The present invention therefore includes gapped oligomeric compounds wherein each wing independently comprises 1, 2 or 3 sugar modified nucleosides. In one embodiment, the internal or gap region comprises from 15 to 23 nucleosides, which is understood to include 15, 16, 17, 18, 19, 20, 21, 22 and 23 nucleotides. In a further embodiment, the internal or gap region is understood to comprise from 17 to 21 nucleosides, which is understood to include 17, 18, 19, 20, or 21 nucleosides. In another embodiment, the internal or gap region is understood to comprise from 18 to 20 nucleosides, which is understood to include 18, 19 or 20 nucleosides. In one preferred embodiment, the gap region comprises 19 nucleosides. In one embodiment, the oligomeric compound is a gapmer oligonucleotides with full length complementarity to its target miRNA. In a further embodiment, the wings are 2'-MOE modified nucleosides and the gap comprises 2'-fluoro modified nucleosides. In one embodiment one wing is 2 nucleosides in length and the other wing is 3 nucleosides in length. In an additional embodiment, the wings are each 2 nucleosides in length and the gap region is 19 nucleotides in length.

Examples of chimeric oligomeric compounds include, but are not limited to, a 23 nucleobase oligomeric compound having a central region comprised of a first modification and wing regions comprised of a second modification (5'MMm-mmmmmmmmmmmmmmmmmmmMM3'); a 22 nucleobase compound having a central region comprised of a first modification and wing regions comprised of a second modification (5'MMmmmmmmmmmmmmmmmmmmmMM3'); and a 21 nucleobase compound having a central region comprised of a first modification and wing regions comprised of a second modification (5'MMmmmmmmmmmmm-mmmmmmmmMM3'); wherein "M" represents the first modification and "m" represents the second modification. In one non-limiting example, "M" may be 2'-O-methoxyethyl and "m" may be 2'-fluoro.

In one embodiment, chimeric oligomeric compounds are "hemimer oligomeric compounds" wherein chemical modifications to sugar moieties and/or internucleoside linkage distinguish a region of subunits at the 5' terminus from a region of subunits at the 3' terminus of the oligomeric compound.

Chimeric oligomeric compounds typically contain at least one region modified so as to confer increased resistance to nuclease degradation, increased cellular uptake, and/or increased binding affinity for the target nucleic acid. An additional region of the oligomeric compound can, for example, contain a different modification, and in some cases may serve as a substrate for enzymes capable of cleaving RNA:DNA or RNA:RNA hybrids. By way of example, an oligomeric compound can be designed to comprise a region that serves as a substrate for RNase H. RNase H is a cellular endonuclease which cleaves the RNA strand of an RNA:DNA duplex. Activation of RNase H by an oligomeric compound having a cleavage region, therefore, results in cleavage of the RNA target, thereby enhancing the efficiency of the oligomeric compound. Alternatively, the binding affinity of the oligomeric compound for its target nucleic acid can be varied along the length of the oligomeric compound by including regions of chemically modified nucleosides which have exhibit either increased or decreased affinity as compared to the other regions. Consequently, comparable results can often be obtained with shorter oligomeric compounds having substrate regions when chimeras are used, compared to for example phosphorothioate deoxyoligonucleotides hybridizing to the same target region.

Chimeric oligomeric compounds of the invention can be formed as composite structures of two or more oligonucleotides, oligonucleotide mimics, oligonucleotide analogs, oligonucleosides and/or oligonucleoside mimetics as described above. Such oligomeric compounds have also been referred to in the art as hybrids, hemimers, gapmers or inverted gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

In another aspect of the chimeric oligomeric compound there is a "gap-disabled" motif (also referred to as "gap-ablated motif"). In the gap-disabled motif, the internal region is interrupted by a chemical modification distinct from that of the internal region. The wing regions can be uniformly sized or differentially sized as also described above. Examples of gap-disabled motifs are as follows: 5'MMMMMMmmmMMMmmmmMMMM3'; 5'MMMM-mmmmmmMmmmmmmMM3'; 5'MMmmmmmmmmm-mMMMmmmMM3'; wherein "m" represents one sugar modification and "M" represents a different sugar modification As used in the present invention the term "alternating motif" is meant to include a contiguous sequence of nucleosides comprising two different nucleosides that alternate for essentially the entire sequence of the oligomeric compound. The pattern of alternation can be described by the formula: 5'-A(-L-B-L-A)n(-L-B)nn-3' where A and B are nucleosides differentiated by having at least different sugar groups, each L is an internucleoside linking group, nn is 0 or 1 and n is from about 7 to about 11. This permits alternating oligomeric compounds from about 17 to about 24 nucleosides in length. This length range is not meant to be limiting as longer and shorter oligomeric compounds are also amenable to the present invention. This formula also allows for even and odd lengths for alternating oligomeric compounds wherein the 3' and 5'-terminal nucleosides are the same (odd) or different (even). These alternating oligomeric compounds may comprise phosphodiester internucleotide linkages, phosphorothioate internucleotide linkages, or a combination of phosphodiester and phosphorothioate internucleotide linkages.

The "A" and "B" nucleosides comprising alternating oligomeric compounds of the present invention are differentiated from each other by having at least different sugar moieties. Each of the A and B nucleosides has a modified sugar moiety selected from β-D-ribonucleosides, β-D-deoxyribonucleosides, 2'-modified nucleosides (such 2'-modified nucleosides may include 2'-MOE, 2'-fluoro, and 2'-O—CH3, among others), and bicyclic sugar modified nucleosides. The alternating motif is independent from the nucleobase sequence and the internucleoside linkages. The internucleoside linkage can vary at each position or at particular selected positions or can be uniform or alternating throughout the oligomeric compound.

As used in the present invention the term "fully modified motif" is meant to include a contiguous sequence of sugar modified nucleosides wherein essentially each nucleoside is modified to have the same modified sugar moiety. Suitable sugar modified nucleosides for fully modified strands of the invention include, but are not limited to, 2'-Fluoro (2'F), 2'-O(CH$_2$)$_2$O CH$_3$ (2'-MOE), 2'-OCH$_3$ (2'-O-methyl), and bicyclic sugar modified nucleosides. In one aspect the 3' and 5'-terminal nucleosides are left unmodified. In a preferred embodiment, the modified nucleosides are either 2'-MOE, 2'-F, 2'-O-Me or a bicyclic sugar modified nucleoside.

As used in the present invention the term "hemimer motif" is meant to include a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified oligomeric compound. An example of a typical hemimer is an oligomeric compound comprising β-D-ribonucleosides or β-D-deoxyribonucleosides that have a sequence of sugar modified nucleosides at one of the termini. One hemimer motif includes a sequence of β-D-ribonucleosides or β-D-deoxyribonucleosides having from 2-12 sugar modified nucleosides located at one of the termini. Another hemimer motif includes a sequence of β-D-ribonucleosides or β-D-deoxyribonucleosides having from 2-6 sugar modified nucleosides located at one of the termini with from 2-4 being suitable. In a preferred embodiment of the invention, the oligomeric compound comprises a region of 2'-MOE modified nucleotides and a region of β-D-deoxyribonucleosides. In one embodiment, the β-D-deoxyribonucleosides comprise less than 13 contiguous nucleotides within the oligomeric compound. These hemimer oligomeric compounds may comprise phosphodiester internucleotide linkages, phosphorothioate internucleotide linkages, or a combination of phosphodiester and phosphorothioate internucleotide linkages.

As used in the present invention the term "blockmer motif" is meant to include a sequence of nucleosides that have uniform sugars (identical sugars, modified or unmodified) that is internally interrupted by a block of sugar modified nucleosides that are uniformly modified and wherein the modification is different from the other nucleosides. More generally, oligomeric compounds having a blockmer motif comprise a sequence of β-D-ribonucleosides or β-D-deoxyribonucleosides having one internal block of from 2 to 6, or from 2 to 4 sugar modified nucleosides. The internal block region can be at any position within the oligomeric compound as long as it is not at one of the termini which would then make it a hemimer. The base sequence and internucleoside linkages can vary at any position within a blockmer motif.

Nucleotides, both native and modified, have a certain conformational geometry which affects their hybridization and affinity properties. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as, but not limited to, antisense mechanisms, including RNase H-mediated and RNA interference mechanisms, as these mechanisms involved the hybridization of a synthetic sequence strand to an RNA target strand. In the case of RNase H, effective inhibition of the mRNA requires that the antisense sequence achieve at least a threshold of hybridization.

One routinely used method of modifying the sugar puckering is the substitution of the sugar at the 2'-position with a substituent group that influences the sugar geometry. The influence on ring conformation is dependent on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoroadenosine) is also correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry. Properties that are enhanced by using more stable 3'-endo nucleosides include but are not limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

The conformation of modified nucleosides and their oligomers can be estimated by various methods such as molecular dynamics calculations, nuclear magnetic resonance spectroscopy and CD measurements. Hence, modifications predicted to induce RNA-like conformations (A-form duplex geometry in an oligomeric context), are useful in the oligomeric compounds of the present invention. The synthesis of modified nucleosides amenable to the present invention are known in the art (see for example, Chemistry of Nucleosides and Nucleotides Vol 1-3, ed. Leroy B. Townsend, 1988, Plenum Press.)

In one aspect, the present invention is directed to oligomeric compounds that are designed to have enhanced properties compared to native RNA or DNA. One method to design optimized or enhanced oligomeric compounds involves each nucleoside of the selected sequence being scrutinized for possible enhancing modifications. One modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention may include at least one 5'-modified phosphate group on a single strand or on at least one 5'-position of a double-stranded sequence or sequences. Other modifications considered are internucleoside linkages, conjugate groups, substitute sugars or bases, substitution of one or more nucleosides with nucleoside mimetics and any other modification that can enhance the desired property of the oligomeric compound.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups (see substituent group list below).

The term "alkenyl," as used herein, refers to a straight or branched hydrocarbon chain radical containing up to twenty four carbon atoms having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butyryl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl or amino portions of the aminoalkyl group can be further substituted with substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines, for example. Aliphatic groups as used herein may optionally include further substituent groups.

The term "alicyclic" refers to a cyclic ring system wherein the ring is aliphatic. The ring system can comprise one or more rings and wherein at least one ring is aliphatic. Alicyclics include rings having any degree of saturation. Preferred alicyclics include rings having from about 5 to about 9 carbon atoms in the ring. Alicyclic as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20, or even from about 6 to about 14 carbon atoms in one or more rings. Aryl groups as used herein may optionally include further substituent groups.

Unless otherwise defined herein, "aralkyl" and "arylalkyl," refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The term "heterocyclic," or "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups. In certain embodiments, heterocycle groups will have, for example, from about 3 to about 50 carbon atoms with from about 4 to about 14 carbon atoms being preferred and from 1 to 4 heteroatoms independently selected form oxygen, nitrogen or sulfur.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups. In certain embodiments, heteroaryl groups will have, for example, from about 3 to about 50 carbon atoms with from about 4 to about 14 carbon atoms being preferred and from 1 to 4 heteroatoms independently selected form oxygen, nitrogen or sulfur.

The term "heteroarylalkyl," as used herein, refers to a heteroaryl group as previously defined, attached to a parent molecule via an alkyl group. Examples include, but are not limited to, pyridinylmethyl, pyrimidinylethyl and the like. Heteroarylalkyl groups as used herein may optionally include further substituent groups.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

Unless otherwise defined herein amide means —C(=O)NH$_2$ and substituted amide means —C(=O)NR$_a$R$_b$ wherein at least one of R$_a$ and R$_b$ is a substituent group other than H.

Unless otherwise defined herein aminoalkyl means a radical group having an amino group attached to an alkyl group wherein one or both groups can be further substituted with one or more substituent groups. The radical group can attach to a parent group from the alkyl or the amino group.

Unless otherwise defined herein aminoalkoxy means a radical group having an amino group attached to an alkyl group which is further attached to an oxy(aminoalkyl-O—) wherein the amino and or the alkyl groups can be further substituted with one or more substituent groups.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

The oligomeric compounds described herein contain a plurality of asymmetric centers and thus give rise to enantiomers, diastereomers, and other stereoisomeric forms that may be defined, in terms of absolute stereochemistry, as (R)- or (S)—, or as (D)- or (L)- for furanosyl sugar groups. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used in herein a substituted group can have one or more substituent groups attached thereto. The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to the parent compound. Such groups include without limitation, halogen, hydroxyl, alkyl, alkenyl, alkynyl, acyl (—C(O)R$_a$), carboxyl (—C(O)O—R$_a$), aliphatic, alicyclic, alkoxy, substituted oxo (—O—R$_a$), aryl, aralkyl, heterocyclic, heteroaryl, heteroarylalkyl, amino (—NR$_b$R$_c$), imino(=NR$_b$), amido (—C(O)NR$_b$R$_c$ or —N(R$_b$)C(O)R$_a$), azido (—N$_3$), nitro (—NO$_2$), cyano (—CN), carbamido (—OC(O)NR$_b$R$_c$ or —N(R$_b$)C(O)OR$_a$), ureido (—N(R$_b$)C(O)—NR$_b$R$_c$), thioureido (—N(R$_b$)C(S)NR$_b$R$_c$), guanidinyl (—N(R$_b$)C(=NR$_b$)NR$_b$R$_c$), amidinyl (—C(=NRO—NR$_b$R$_c$ or —N(R$_b$)C(NR$_b$)R$_a$), thiol (—SR$_b$), sulfinyl (—S(O)R$_b$), sulfonyl (—S(O)$_2$R$_b$), sulfonamidyl (—S(O)$_2$NR$_b$R$_c$ or —N(R$_b$)S(O)$_2$R$_b$) and conjugate groups. Wherein each R$_a$, R$_b$ and R$_c$ is a further substituent group with a preferred list including without limitation alkyl, alkenyl, alkynyl, aliphatic, alkoxy, acyl, aryl, aralkyl, heteroaryl, alicyclic, heterocyclic and heteroarylalkyl.

Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

Screening Oligomeric Compounds

Screening methods for the identification of effective modulators of small non-coding RNAs, including miRNAs, are also comprehended by the instant invention and comprise the steps of contacting a small non-coding RNA, or portion thereof, with one or more candidate modulators, and selecting for one or more candidate modulators which decrease or increase the levels, expression or alter the function of the small non-coding RNA. As described herein, the candidate modulator can be an oligomeric compound targeted to a miRNA, or any portion thereof. Once it is shown that the candidate modulator or modulators are capable of modulating (e.g. either decreasing or increasing) the levels, expression or altering the function of the small non-coding RNA, the modulator may then be employed in further investigative studies, or for use as a target validation, research, diagnostic, or therapeutic agent in accordance with the present invention. In one embodiment, the candidate modulator is screened for its ability to modulate the function of specific miRNA.

Oligonucleotide Synthesis

Oligomeric compounds and phosphoramidites are made by methods well known to those skilled in the art. Oligomerization of modified and unmodified nucleosides is performed according to literature procedures for DNA like compounds (Protocols for Oligonucleotides and Analogs, Ed. Agrawal (1993), Humana Press) and/or RNA like compounds (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. Alternatively, oligomers may be purchased from various oligonucleotide synthesis companies such as, for example, Dharmacon Research Inc., (Lafayette, Colo.).

Irrespective of the particular protocol used, the oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed (including solution phase synthesis).

Methods of isolation and analysis of oligonucleotides are well known in the art. A 96-well plate format is particularly useful for the synthesis, isolation and analysis of oligonucleotides for small scale applications.

Design and Screening of Duplexed Oligomeric Compounds

In screening and target validation studies, oligomeric compounds of the invention can be used in combination with their respective complementary strand oligomeric compound to form stabilized double-stranded (duplexed) oligonucleotides. In accordance with the present invention, a series of duplexes comprising the oligomeric compounds of the present invention and their complements can be designed to target a small non-coding RNA. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in some embodiments, both strands of the duplex would be complementary over the central nucleobases, each having overhangs at one or both termini, as described supra.

In some embodiments, a duplex comprising an antisense strand having the sequence CGAGAGGCG-GACGGGACCG (SEQ ID NO: 1) may be prepared with blunt ends (no single stranded overhang) as shown:

```
cgagaggcggacgggaccg Antisense Strand (SEQ ID NO: 1)
|||||||||||||||||||
gctcuccgccugcccuggc Complement (SEQ ID NO: 2)
```

In other embodiments, a duplex comprising an antisense strand having the sequence CGAGAGGCG-GACGGGACCG (SEQ ID NO: 1), having a two-nucleobase overhang of deoxythymidine (dT) and its complement sense strand may be prepared with overhangs as shown:

```
cgagaggcggacgggaccgTT Antisense Strand (SEQ ID NO: 3)
|||||||||||||||||||
  TTgcucuccgccugcccuggc  Complement Sense Strand (SEQ ID NO: 4)
```

These sequences are shown to contain uracil (U) but one of skill in the art will appreciate that uracil (U) is generally replaced by thymine (T) in DNA sequences. RNA strands of the duplex can be synthesized by methods disclosed herein or purchased from Dharmacon Research Inc. (Lafayette, Colo.).

Diagnostics, Drug Discovery and Therapeutics

The oligomeric compounds and compositions of the present invention can additionally be utilized for research, drug discovery, kits and diagnostics, and therapeutics.

For use in research, oligomeric compounds of the present invention are used to interfere with the normal function of the nucleic acid molecules to which they are targeted. Expression patterns within cells or tissues treated with one or more oligomeric compounds or compositions of the invention are compared to control cells or tissues not treated with the compounds or compositions and the patterns produced are analyzed for differential levels of nucleic acid expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

For use in drug discovery, oligomeric compounds of the present invention are used to elucidate relationships that exist between small non-coding RNAs, genes or proteins and a disease state, phenotype, or condition. These methods include detecting or modulating a target comprising contacting a sample, tissue, cell, or organism with the oligomeric compounds and compositions of the present invention, measuring the levels of the target and/or the levels of downstream gene products including mRNA or proteins encoded thereby, a related phenotypic or chemical endpoint at some time after treatment, and optionally comparing the measured value to an untreated sample, a positive control or a negative control. These methods can also be performed in parallel or in combination with other experiments to determine the function of unknown genes for the process of target validation or to determine the validity of a particular gene product as a target for treatment or prevention of a disease.

For use in kits and diagnostics, the oligomeric compounds and compositions of the present invention, either alone or in combination with other compounds or therapeutics, can be used as tools in differential and/or combinatorial analyses to elucidate expression patterns of a portion or the entire complement of non-coding or coding nucleic acids expressed within cells and tissues.

The specificity and sensitivity of compounds and compositions can also be harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, preferably a human, suspected of having a disease or disorder presenting conditions that can be treated, ameliorated, or improved by modulating the expression of a selected small non-coding target nucleic acid is treated by administering the compounds and compositions. Exemplary compounds of the instant invention exhibit potent activity and improved therapeutic index and are thus suitable for therapeutic applications. For example, in one non-limiting embodiment, the methods comprise the step of administering to or contacting the animal, an effective amount of a modulator to treat, ameliorate or improve the conditions associated with the disease or disorder. Exemplary compounds of the present invention effectively modulate the activity or function of the small non-coding RNA target or inhibit the expression or levels of the small non-coding RNA target. In preferred embodiments, the small non-coding RNA target is a miRNA, a pre-miRNA, or a polycistronic or monocistronic pri-miRNA. In additional embodiments, the small non-coding RNA target is a single member of a miRNA family. Alternatively, two or more members of an miRNA family are selected for modulation. In one embodiment, the level, activity or expression of the target in an animal is inhibited by about 10%. In another embodiment the level, activity or expression of a target in an animal is inhibited by about 30%. Further, the level, activity or expression of a target in an animal is inhibited by 50% or more, by 60% or more, by 70% or more, by 80% or more, by 90% or more, or by 95% or more. In another embodiment, the present invention provides for the use of a compound of the invention in the manufacture of a medicament for the treatment of any and all conditions associated with miRNAs and miRNA families.

The reduction of target levels can be measured in serum, adipose tissue, liver or any other body fluid, tissue or organ of the animal known to contain the small non-coding RNA or its precursor. Further, the cells contained within the fluids, tissues or organs being analyzed contain a nucleic acid molecule of a downstream target regulated or modulated by the small non-coding RNA target itself.

Compositions and Methods for Formulating Pharmaceutical Compositions

The present invention also include pharmaceutical compositions and formulations that include the oligomeric compounds, small non-coding RNAs and compositions of the invention. Compositions and methods for the formulation of pharmaceutical compositions are dependent upon a number of criteria, including, but not limited to, route of administration, extent of disease, or dose to be administered. Such considerations are well understood by those skilled in the art.

The oligomeric compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

The oligomeric compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salts" refers to physiologically and pharmaceutically acceptable salts of the compounds and compositions of the invention: i.e., salts that retain the desired biological activity of the parent compound and do not impart undesired toxicological effects thereto. Suitable examples include, but are not limited to, sodium and potassium salts.

In some embodiments, an oligomeric compound can be administered to a subject via an oral route of administration. The subject may be a mammal, such as a mouse, a rat, a dog, a guinea pig, or a non-human primate. In some embodiments, the subject may be a human or a human patient. In certain embodiments, the subject may be in need of modulation of the level or expression of one or more pri-miRNAs as discussed in more detail herein. In some embodiments, compositions for administration to a subject will comprise modified oligonucleotides having one or more modifications, as described herein.

Cell Culture and Oligonucleotide Treatment

The effects of oligomeric compounds on target nucleic acid expression or function can be tested in any of a variety of cell types provided that the target nucleic acid is present at measurable levels. This can be readily determined by methods routine in the art, for example Northern blot analysis, ribonuclease protection assays, or real-time PCR. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to: T-24 cells, A549 cells, normal human mammary epithelial cells (HMECs), MCF7 cells, T47D cells, BJ cells, B16-F10 cells, human vascular endothelial cells (HUVECs), human neonatal dermal fibroblast (NHDF) cells, human embryonic keratinocytes (HEK), 293T cells, HepG2, human preadipocytes, human differentiated adipocytes (preapidocytes differentiated according to methods known in the art), NT2 cells (also known as NTERA-2 cl.D1), and HeLa cells.

Treatment with Antisense Oligomeric Compounds

In general, when cells reach approximately 80% confluency, they are treated with oligomeric compounds of the invention. Oligomeric compounds are introduced into cells using the cationic lipid transfection reagent LIPOFECTIN® (Invitrogen, Carlsbad, Calif.). Oligomeric compounds are mixed with LIPOFECTIN® in OPTI-MEM® 1 (Invitrogen, Carlsbad, Calif.) to achieve the desired final concentration of oligomeric compound and LIPOFECTIN®. Before adding to cells, the oligomeric compound, LIPOFECTIN® and OPTI-MEM® 1 are mixed thoroughly and incubated for approximately 0.5 hrs. The medium is removed from the plates and the plates are tapped on sterile gauze. Each well of a 96-well plate is washed with 150 µl of phosphate-buffered saline or Hank's balanced salt solution. Each well of a 24-well plate is washed with 250 µL of phosphate-buffered saline or Hank's balanced salt solution. The wash buffer in each well is replaced with 100 µL or 250 µL of the oligomeric compound/OPTI-MEM® 1/LIPOFECTIN® cocktail for 96-well or 24-well plates, respectively. Untreated control cells receive LIPOFECTIN® only. The plates are incubated for approximately 4 to 7 hours at 37° C., after which the medium is removed and the plates are tapped on sterile gauze. 100 µl or 1 mL of full growth medium is added to each well of a 96-well plate or a 24-well plate, respectively. Cells are harvested 16-24 hours after oligonucleotide treatment, at which time RNA can be isolated and target reduction measured by real-time PCR, or other phenotypic assays performed. In general, data from treated cells are obtained in triplicate, and results presented as an average of the three trials.

Alternatively, cells are transfected using LIPOFECTAMINE® (Invitrogen, Carlsbad, Calif.). When cells reached 65-75% confluency, they are treated with oligonucleotide. Oligonucleotide is mixed with LIPOFECTAMINE® in OPTI-MEM® 1 reduced serum medium (Invitrogen, Carlsbad, Calif.) to achieve the desired concentration of oligonucleotide and a LIPOFECTAMINE® concentration of ranging from 2 to 12 µg/mL per 100 nM oligonucleotide. This transfection mixture is incubated at room temperature for approximately 0.5 hours. For cells grown in 96-well plates, wells are washed once with 100 µL OPTI-MEM® 1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh medium. Cells were harvested 16-24 hours after oligonucleotide treatment.

In some embodiments, cells are transiently transfected with oligomeric compounds of the instant invention. In some embodiments, cells are transfected and selected for stable expression of an oligomeric compound of the instant invention.

The concentration of oligonucleotide used varies from cell line to cell line. Methods to determine the optimal oligonucleotide concentration for a particular cell line are well known in the art. For example, the cells are treated with a positive control oligonucleotide targeting a gene such as H-ras, at a range of concentrations. Controls may be unmodified, uniformly modified, or chimeric oligomeric compounds. The concentration of positive control oligonucleotide that results in, for example, 80% inhibition of the control target RNA is then be utilized as the screening concentration for new oligonucleotides in subsequent experiments for that cell line. If 80% inhibition is not achieved, the lowest concentration of positive control oligonucleotide that results in 60% inhibition of target expression or function is then utilized as the oligonucleotide screening concentration in subsequent experiments for that cell line. The concentrations of oligonucleotides used herein can range from 1 nM to 300 nM.

Analysis of Oligonucleotide Inhibition of Target Levels or Expression

Modulation of target levels or expression can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Additional examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression)(Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904), and mass spectrometry methods (To, Comb. Chem. High Throughput Screen, 2000, 3, 235-41).

RNA Isolation

RNA is prepared from cell lines such as HeLa, NT2, T-24, and A549 using methods well known in the art, for example, using the TRIZOL® (Invitrogen, Carlsbad, Calif.) according to the manufacturer's recommended protocols. Briefly, cell monolayers are washed twice with cold PBS, and cells are lysed using TRIZOL® (Invitrogen, Carlsbad, Calif.) at a volume of 1 mL per 10 cm$^2$ culture dish surface area, and total RNA is prepared according to the TRIZOL® protocol.

Quantitative Real-Time PCR Analysis of Target RNA Levels

Quantitation of target RNA levels is accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene (or RNA) target quantities obtained by real time PCR are normalized using either the expression level of a gene whose expression is constant, such as GAPDH, or by quantifying total RNA using RIBOGREEN® (Molecular Probes, Inc. Eugene, Oreg.). GAPDH expression is quantified by real time PCR, by being run simultaneously with the target, multiplexing, or separately. Total RNA is quantified using RIBOGREEN® RNA quantification reagent (Molecular Probes, Inc. Eugene, Oreg.). Methods of RNA quantification by RIBOGREEN® are taught in Jones, L. J., et al, (Analytical Biochemistry, 1998, 265, 368-374).

In this assay, 170 μL of RIBOGREEN® working reagent (RIBOGREEN® reagent diluted 1:350 in 10 mM Tris-HCl, 1 mM EDTA, pH 7.5) is pipetted into a 96-well plate containing 30 μL purified, cellular RNA. The plate is read in a CYTOFLUOR® 4000 (PE Applied Biosystems) with excitation at 485 nm and emission at 530 nm.

Probes and primers are designed to hybridize to the target sequence. Methods for designing real-time PCR probes and primers are well known in the art, and may include the use of software such as PRIMER EXPRESS® Software (Applied Biosystems, Foster City, Calif.). Such software can be used to design probes and primers for the detection of mRNA such as ALDOA and GYS1.

Northern Blot Analysis of Target RNA Levels

Northern blot analysis is performed according to routine procedures known in the art. Fifteen to twenty micrograms of total RNA is fractionated by electrophoresis through 10% acrylamide urea gels using a TBE buffer system (Invitrogen). RNA is transferred from the gel to HYBOND™-N+ nylon membranes (Amersham Pharmacia Biotech, Piscataway, N.J.) by electroblotting in an Xcell SURELOCK™ Minicell (Invitrogen, Carlsbad, Calif.). Membranes are fixed by UV cross-linking using a STRATALINKER® UV Crosslinker 2400 (Stratagene, Inc, La Jolla, Calif.) and then probed using RAPID-HYB™ buffer solution (Amersham) using manufacturer's recommendations for oligonucleotide probes.

A target specific DNA oligonucleotide probe with the sequence is used to detect the RNA of interest. Probes used to detect miRNAs are synthesized by commercial vendors such as IDT (Coralville, Iowa). The probe is 5' end-labeled with T4 polynucleotide kinase with ($\gamma$-$^{32}$P) ATP (Promega, Madison, Wis.). To normalize for variations in loading and transfer efficiency membranes are stripped and re-probed for U6 RNA. Hybridized membranes are visualized and quantitated using a STORM® 860 PHOSPHORIMAGER® System and IMAGEQUANT® Software V3.3 (Molecular Dynamics, Sunnyvale, Calif.).

Analysis of Protein Levels

Protein levels of a downstream target modulated or regulated by a small non-coding RNA can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

Phenotypic Assays

Once modulators are designed or identified by the methods disclosed herein, the oligomeric compounds are further investigated in one or more phenotypic assays, each having measurable endpoints predictive or suggestive of efficacy in the treatment, amelioration or improvement of physiologic conditions associated with a particular disease state or condition.

Phenotypic assays, kits and reagents for their use are well known to those skilled in the art and are herein used to investigate the role and/or association of a target in health and disease. Representative phenotypic assays include cell cycle assays, apoptosis assays, angiogenesis assays (e.g. endothelial tube formation assays, angiogenic gene expression assays, matrix metalloprotease activity assays), adipocyte assays (e.g. insulin signaling assays, adipocyte differentiation assays), inflammation assays (e.g. cytokine signaling assays, dendritic cell cytokine production assays); examples of such assays are readily found in the art (e.g., U.S. Application Publication No. 2005/0261218, which is hereby incorporated by reference in its entirety). Additional phenotypic assays include those that evaluate differentiation and dedifferentiation of stem cells, for example, adult stem cells and embryonic stem cells; protocols for these assays are also well known in the art (e.g. Turksen, Embryonic Stem Cells: Methods and Protocols, 2001, Humana Press; Totowa, N.J.; Klug, Hematopoietic Stem Cell Protocols, 2001, Humana Press, Totowa, N.J.; Zigova, Neural Stem Cells: Methods and Protocols, 2002, Humana Press, Totowa, N.J.).

Luciferase Reporter Assay.

The activity of oligomeric compounds targeted to miRNAs can be evaluated in vitro using a DUAL-LUCIFERASE® Reporter Assay (Promega, Madison, Wis.) in which luciferase activity is inhibited by normal miRNA activity (i.e., binding to its complementary sequence). An oligomeric compound targeted to a miRNA prevents the miRNA from binding to its complementary sequence in the luciferase reporter, thus promoting luciferase activity. The luciferase reporter can be engineered using a miRNA sequence of interest.

A miRNA luciferase sensor construct is engineered by inserting a sequence complementary to a miRNA of interest into the 3'-UTR of pGL3-Control (Promega, Madison, Wis.). On day one of the assay, HeLa cells (from ATCC, Manassas, Va.) are seeded in T-170 flasks (BD Biosciences, Franklin Lakes, N.J.) at 3.5*10$^6$ cells/flask. HeLa cells are grown in Dulbecco's Modified Eagle Medium with High Glucose (Invitrogen, Carlsbad, Calif.). On day two, each flask of HeLa cells is transfected with 10 ug miRNA luciferase sensor construct. Each flask is also transfected with 0.5 ug of a phRL sensor plasmid (Promega, Madison, Wis.) expressing Renilla, to be used in normalization of the luciferase signal. HeLa cells are transfected using 20 uL LIPOFECTAMINE® 2000 per flask (Invitrogen, Carlsbad, Calif.). After 4 hours of transfection, the cells are washed with PBS and then trypsinized. The transfected HeLa cells are re-plated at 40,000 per well in 24 well plates (BD Falcon) and left overnight. On day 3, HeLa cells are transfected with oligomeric compounds using LIPOFECTIN® (Invitrogen, Carlsbad, Calif.) at 2.5 ul LIPOFECTIN® per 100 nM ASO in 1 mL OPTI-MEM®-1 Reduced Serum Medium (Invitrogen, Carlsbad, Calif.) for 4 hours. After ASO transfection, the oligomeric compound-containing medium is replaced with Dulbecco's Modified Eagle Medium with High Glucose (Invitrogen, Carlsbad, Calif.). On day four, HeLa cells are passively lysed and luciferase activity is measured using the DUAL-LUCIFERASE® Reporter Assay (Promega, Madison, Wis.).

In Vivo Studies

Experimental animal models are used to evaluate the efficacy, potency and therapeutic index of oligomeric compounds targeted to miRNAs.

Animals are obtained from commercial suppliers, such as Jackson Laboratories. Oligomeric compounds are generally in a saline solution, and are administered intraperitoneally. At the end of a study, organs are weighed, RNA is isolated from various tissues for quantitative PCR analysis, and serum or blood is collected for measurements of serum markers such as cholesterol, triglycerides, and glucose. Liver tissue triglycerides may also be measured.

Additional analyses that are performed in such in vivo studies included histological analysis of liver sections, to evaluate changes in morphology. Histological analysis of liver is carried out via routine procedures known in the art. Briefly, liver is fixed in 10% buffered formalin and embedded in paraffin wax. 4-mm sections are cut and mounted on glass slides. After dehydration, the sections are stained with hematoxylin and eosin. Morphological analysis may also include evaluation of hepatic steatosis, using oil Red 0 staining procedures known in the art.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is specifically incorporated herein by reference in its entirety.

In order that the invention disclosed herein may be more efficiently understood, examples are provided below. Throughout these examples, molecular cloning reactions, and other standard recombinant DNA techniques, were carried out according to routine methods, such as those described in Maniatis et al., Molecular Cloning—A Laboratory Manual, 2nd ed., Cold Spring Harbor Press (1989), using commercially available reagents, except where otherwise noted.

It should be understood that these examples are for illustrative purposes only and are not to be construed as limiting the invention in any manner. Those of ordinary skill in the art will readily adopt the underlying principles of this discovery to design various compounds without departing from the spirit of the current invention.

EXAMPLES

Example 1

Anti-miRNA Activity of Uniformly Modified Oligomeric Compounds

Uniformly modified oligomeric compounds targeted to miRNAs were tested for their ability to modulate miRNA activity in the luciferase reporter assay. The uniformly modified compounds comprised uniform sugar modifications, uniform internucleoside linkage modifications, or combinations thereof. Following treatment of cultured cells with oligomeric compounds, luciferase activity is measured; an increase in luciferase activity indicates that the oligomeric compound inhibits miRNA activity.

A miR-21 luciferase sensor construct was engineered by inserting the 22 nucleotide complement of miR-21 (TAGCTTATCAGACTGATGTTGA; SEQ ID NO: 113) into the 3'-UTR of pGL3-Control (Promega). The dual-luciferase assay was performed as described herein.

HeLa cells were transfected with anti-miR-21 oligomeric compounds (having the nucleotide sequence TCAACATCAGTCTGATAAGCTA, SEQ ID NO: 113) having the following uniformly modified motifs: uniform 2'-MOE and uniform phosphorothioate; uniform 2'-MOE and uniform phosphodiester; uniform 2'-O-Me and uniform phosphorothioate; uniform 2'-OMe and uniform phosphodiester; uniform 2'-F and uniform phosphorothioate. Among the oligomeric compounds with phosphorothioate backbones, the uniform 2'-F oligomeric compound had the greatest anti-miR-21 activity, followed by uniform 2'-MOE and 2'-OMe oligomeric compounds. The overall greatest anti-miR-21 activity was achieved with a uniform 2'-MOE oligomeric compound with a phosphodiester.

Uniformly modified compounds having mismatches with respect to miR-21 were also tested. HeLa cells were treated with anti-miR-21 oligomeric compounds comprising uniform 2'-MOE modifications and uniform phosphorothioate internucleoside linkages. A total of one to six mismatches was introduced into the oligomeric compounds. Introduction of a single mismatch into an oligomeric compound reduced its ability to inhibit miR-21. The introduction of a single mismatch into the 3' end of the oligomeric compound, which is complementary to the 5' seed region of the miRNA, resulted in additional loss of activity relative to the other oligomeric compounds containing a single mismatch. The introduction of two or more mismatches resulted in poor activity, and the introduction of three or more mismatches ablated activity. Thus, the strength of modulation of a target miRNA by an oligomeric compound can be regulated by introduction of mismatches.

The effect of truncations on the inhibitory of oligomeric compounds was also tested. Hela cells were treated with anti-miR-21 oligomeric compounds comprising uniform 2'-MOE and uniform phosphorothioate internucleoside linkages, into which 5' end or 3' end subunit truncations were introduced. Truncating the ASOs from either the 5' or 3' end by a single subunit was well tolerated. A single subunit truncation from the 3' end of the oligomeric compound modestly improved the inhibitory activity of the anti-miR-21 oligomeric compound. Truncations of 2 or more subunits resulted in a significant loss of anti-miR-21 activity. Thus, the strength of modulation of a target miRNA by an oligomeric compound can be regulated by truncations.

The duration of action of a uniformly modified oligomeric compound was evaluated. HeLa cells were treated with anti-miR-21 oligomeric compounds modified as follows: uniform 2'-MOE and uniform phosphodiester; uniform 2'-MOE and phosphorothioate; uniform 2'-OMe and uniform phosphodiester; uniform 2'-OMe and uniform phosphorothioate. Luciferase activity was measured 4, 8, 24, and 48 hours after oligomeric compound transfection. At early time points, each uniformly modified oligomeric compound showed comparable anti-miR-21 activity. However, after 24 and 48 hours, the uniform 2'-MOE oligomeric compound with a phosphodiester backbone was the most active in this assay, followed by the uniform 2'-F and then uniform 2'-MOE oligomeric compounds, each with phosphorothioate backbones.

These results demonstrate that uniformly modified compounds effectively inhibit miR-21 activity. Accordingly, in one embodiment are uniformly modified oligomeric compounds targeted to miRNAs. In a further embodiment are methods of inhibiting miRNA activity comprising contacting cells with oligomeric compounds targeted to miRNAs.

Example 2

Chimeric Oligomeric Compounds

Chimeric oligomeric compounds are oligomeric compounds comprising two or more regions of chemical modifications. One example of a chimeric oligomeric compound is a "gapmer." In a gapmer the oligomeric compound has a motif that comprises a central region and two flanking regions, termed "wings." In one aspect, the nucleotides of the central region comprise one sugar modification, while the nucleotides of the wing regions comprise a different sugar modification. Typically, the wing regions are uniform in their nucleobase lengths; however, such is not necessarily a requirement for a gapmer.

By way of example, a suitable motif for a chimeric oligomeric compound is as follows:

$T_1$-$(Nu_1)_{n1}$-$(Nu_2)_{n2}$-$(Nu_3)_{n3}$-$(Nu_4)_{n4}$-$(Nu_5)_{n5}$-$T_2$, where $T_1$ is H, T2 is H, $Nu_1$ is 2'-MOE, $Nu_2$ is 2'-F, $Nu_5$ is 2'-MOE, n1 is 2, n2 is 19, n3 is 0, n4 is 0, and n5 is 2. The oligomeric compound ISIS 393206 has this motif applied to the nucleobase sequence of SEQ ID NO: 19. In other words, ISIS 393206 has an internal region comprised of 19 2'-F modified nucleotides flanked on each end by external regions each having two 2'-MOE modified nucleotides (2'-MOE/2'-F/2'-MOE).

Chimeric oligomeric compounds targeted to miR-122 were tested for their ability to inhibit miR-122 activity in vivo. In this example, oligomeric compounds targeted to miR-122 are illustrated; however, the modifications in the oligomeric compounds of the invention are not limited to those oligomeric compounds that modulate miR-122.

Single Dosage Amount Study

Male C57BL/6 mice were obtained from a commercial supplier. The mice were separated into the following treatment groups: treatment with ISIS 327895; treatment with ISIS 393206; and treatment with saline. Each oligomeric compound has the nucleobase sequence 5'-ACAAACAC-CATTGTCACACTCCA-3' (SEQ ID NO: 19). ISIS 327895 comprises uniform 2'-MOE sugar modifications, and uniform phosphorothioate internucleoside linkage modifications. The saline-treated mice served as controls. Mice received intraperitoneal injections of 25 mg/kg dose of oligomeric compound, twice per week for 3 weeks. The mice appeared healthy and normal at the end of treatment with plasma AST and ALT levels in the normal range.

The levels of a miR-122 target mRNA, ALDOA, were evaluated in liver tissue using Taqman real-time PCR and compared to ALDOA mRNA levels in saline-treated animals. Treatment with ISIS 327985 and ISIS 393206 resulted in approximately 4-fold and 7-fold increases in ALDOA, respectively. Thus, it is demonstrated herein that the chimeric oligomeric compound exhibits enhanced anti-miR activity relative to the uniformly 2'-MOE modified oligomeric compound. Increased spleen weights were observed following treatment with the 2'-F containing oligomeric compound, suggesting an immunostimulatory activity. As the uniform 2'-MOE oligomeric compound and 2'-MOE/2'-F/2'-MOE oligomeric compound have similar melting temperatures, the two oligomeric compounds were expected to yield similar increases in ALDOA mRNA levels. Accordingly, it is unexpected that an oligomeric compound comprising an internal region of 19 2'-F modified nucleotides and external regions of 2 2'-MOE modified nucleotides would possess significantly greater anti-miR activity than a uniformly 2'-MOE modified oligomeric compound.

Plasma levels of total cholesterol were also monitored using methods known in the art (for example, via Olympus AU400e automated clinical chemistry analyzer, Melville, N.Y.). Reductions in total cholesterol were observed in mice treated with ISIS 327985 and ISIS 393206, relative to saline-treated animals.

Onset of Action Study

To compare the onset of miR-122 inhibitory activity following treatment with uniformly modified or chimeric oligomeric compounds, ISIS 327895 and ISIS 393206 were administered to mice at a dose of 25 mg/kg, two times per week, for up to 5 weeks. Groups of 4 mice per treatment group were sacrificed 24 hours following doses 1, 2, 3, 4, 5, 6, 8, and 10. Measurements of ALDOA mRNA levels and plasma cholesterol studies after each indicated that the 2'-MOE/2'-F/2'-MOE oligomeric compound exhibited greater anti-miR-122 activity, i.e. an increase in ALDOA mRNA levels and a decrease in plasma cholesterol levels. Furthermore, ALDOA increases and lowered plasma cholesterol levels were observed at earlier timepoints following treatment with the 2'-MOE/2'-F72'-MOE oligomeric compound, relative to the uniform 2'-MOE oligomeric. Thus, it is demonstrated that a 2'-MOE/2'-F/2'-MOE oligomeric compound exhibited greater efficacy and an earlier onset of action relative to a 2'-MOE oligomeric compound.

Dose Response Study

To evaluate the dose dependency of anti-miRNA oligomeric compounds, the uniform 2'-MOE and 2'-MOE/2'-F/2'-MOE oligomeric compounds were administered to mice at doses of 6.25, 12.5, 25, or 50 mg/kg, twice weekly, for 3 weeks. The 6.25, 12.5, 25 and 50 mg/kg doses of the 2'-MOE/2'-F/2'-MOE oligomeric compound resulted in ALDOA mRNA increases approximately 4, 5, 4.25, and 5 times that measured in saline-treated animals, respectively. The same doses of the uniform 2'-MOE oligomeric compound resulted in ALDOA mRNA increases approximately 0.25, 1.5, 2. and 3 times that measured in saline-treated animals, respectively. Plasma cholesterol levels were similarly reduced in a dose responsive manner; the 2'-MOE/2'-F/2'-MOE oligomeric compound at doses of 6.25, 12.5, 25 and 50 mg/kg reduced plasma cholesterol levels by approximately 40%, 45%, 45% and 48% relative to plasma cholesterol levels in saline-treated animals, respectively. The 3 lower doses of the 2'-MOE oligomeric compound resulted in a plasma cholesterol levels reduction of approximately 5%, while the highest dose reduced plasma cholesterol levels by at least 40%. Thus, it demonstrated that the 2'-MOE/2'-F/2'-MOE oligomeric compounds demonstrated significantly improved efficacy and potency relative to the 2'-MOE oligomeric compound.

The chimeric oligomeric compounds provided demonstrated enhanced anti-miRNA activity. Accordingly, provided herein are methods for inhibiting miRNA activity comprising administering to an animal an oligomeric compound having enhanced anti-miRNA activity, such as those described herein. In some embodiments, the oligomeric compounds are chimeric oligomeric compounds comprising an internal region comprising 2'-F modified nucleotides and external regions comprising stability enhancing modifications. In one embodiment, the oligomeric compound comprises an internal region comprising a first 2'-modified nucleotide and external regions each comprising a second 2'-modified nucleotide. In a further embodiment, the gap region comprises 2'-fluoro modifications and the wing regions comprise 2'-methoxyethyl modifications. In one embodiment, the oligomeric compound is ISIS 393206.

Example 3

Oligomeric Compounds Having Potent Activity

Oligomeric compounds targeted to miRNAs and having a positionally modified motif were tested for their ability to inhibit miRNA activity in vivo.

Oligomeric compounds comprising 10-12 2'-F sugar modifications and an additional modification in an internal region were tested. The additional modification comprised 2'-OMe, 2'-MOE or a 4'-CH2-O-2' bridged sugar modification. The oligomeric compounds comprised the sequence of SEQ ID NO: 19. ISIS 396608 has the positionally modified motif 5'-MMLFFLFFLFFLFFLFFLFFLFFLMM-3', where M is 2'-MOE, L is a bicyclic nucleic acid having a 4'-CH2-O-2' bridge; ISIS 397303 has the positionally modified motif 5'-MMFMFMFMFMFMFMFMFMFMFMFMM-3', where M is 2'-MOE and F is 2'-F; ISIS 397404 has the positionally modified motif 5'-MMFOFOFOFOFOFOFOFOFOFMM-3', where M is 2'-MOE, F is 2'-F and O is 2'-OMe.

The oligomeric compounds were administered to mice at doses of 25 mg/kg, twice per week for 3 weeks. ALDOA mRNA levels in liver were measured. The oligomeric compounds having 2'-MOE or 2'-OMe introduced into the 2'-F internal region increased ALDOA mRNA levels 2-2.5 times that of saline-treated animals. The introduction of a 4'-CH2-O-2' bridged sugar modification resulted in ALDOA mRNA levels approximately 3.5 times those in saline-treated animals, and also reduced cholesterol by approximately 40%. The 2'-MOE/2'-F/2'-MOE resulted in the highest increase in ALDOA mRNA levels and the greatest decreases in plasma total cholesterol (approximately 60%), as well as in higher spleen weights.

Example 4

Oligomeric Compounds Having Potent Activity and Improved Therapeutic Index

The incorporation of a 2'-MOE/2'-F/2'-MOE motif into an oligomeric compound targeting a miRNA yielded high efficacy and potency in vivo, thus this motif is desirable to incorporate into anti-miR oligomeric compounds for, among other uses, therapeutic applications. To further improve the therapeutic index of this motif, positionally modified oligomeric compounds were designed to have 2'-modifications other than 2'-F incorporated into the internal region of a chimeric motif. A subset of the oligomeric compounds tested as described below are shown in Table A. An additional compound tested was ISIS 400129, having modified nucleosides linked by phosphorothioate internucleoside linkages, as follows: arranged as follows: two 2'-MOE, three 2'-F, one 2'-MOE, five 2'-F, one 2'-MOE, five 2'-F, one 2'-MOE, three 2'-F, two 2'-MOE.

were measured by quantitative PCR and compared to those measured in livers of saline-treated mice. ISIS 393206 increased ALDOA mRNA by approximately 4-fold, and decreased cholesterol by approximately 50%. Treatment with each of ISIS 400124, 400125, 400126, 400127, 400128, 400129, and 400130 oligomeric compound resulted in increased ALDOA mRNA levels above those measured in livers of saline-treated mice by at least 2-fold. Reductions in total plasma cholesterol were between 20% and 40%. Notably, ISIS 400124, 400126, and 400127 were able to increase ALDOA mRNA levels as effectively as ISIS 393206, by approximately 4-fold relative to saline-treated liver ALDOA levels. Furthermore, these oligomeric compounds did not significantly increase spleen weights, whereas ISIS 393206 treatment did raise spleen weights. ISIS 400125, ISIS 400129, and ISIS 400128 increased ALDOA mRNA levels by approximately 3-fold, 2.5-fold and 2-fold, respectively, but did not increase spleen weights. While ISIS 400130, containing one 2'-F in the internal region of the oligomeric compound, increased ALDOA mRNA levels by approximately 3-fold, but also resulted in increased spleen weights comparable to those observed in mice treated with ISIS 393206.

Single Administration Study

A study was performed to evaluate the effects of a single administration of oligomeric compounds targeted to miR-122. The oligomeric compounds comprised the following motifs: uniformly modified 2'-MOE; 2'-MOE/2'-F/2'-MOE; and positionally modified having at least 16 2'-F in an internal region. Mice (Balb/c female, n=4 per treatment group) were given a single intraperitoneal dose of 11, 33, or 100 mg/kg, and sacrificed 4 days later. ALDOA mRNA levels and GYS1 mRNA levels, both of which are known to be increased following miR-122 antisense inhibition, were measured in liver, and compared to respective mRNA levels in livers of saline-treated mice. Table B summarizes the data from this study; ALDOA and GYS1 mRNA levels are shown as percent of saline control; CHOL is cholesterol as percent of baseline (beginning of study); SD is standard deviation.

TABLE A

| ISIS No | SEQ ID NO | n1 | n2 | n3 | n4 | n5 | Nu$_1$ | Nu$_3$ | Nu$_5$ | T$_1$ | T$_2$ |
|---|---|---|---|---|---|---|---|---|---|---|---|
| 393206 | 19 | 2 | 19 | 0 | 0 | 2 | 2'-MOE | 2'-MOE | 2'-MOE | H | H |
| 400124 | 19 | 2 | 2 | 3 | 14 | 2 | 2'-MOE | 2'-MOE | 2'-MOE | H | H |
| 400125 | 19 | 2 | 5 | 3 | 11 | 2 | 2'-MOE | 2'-MOE | 2'-MOE | H | H |
| 400126 | 19 | 2 | 8 | 3 | 8 | 2 | 2'-MOE | 2'-MOE | 2'-MOE | H | H |
| 400127 | 19 | 2 | 11 | 3 | 5 | 2 | 2'-MOE | 2'-MOE | 2'-MOE | H | H |
| 400128 | 19 | 2 | 14 | 3 | 2 | 2 | 2'-MOE | 2'-MOE | 2'-MOE | H | H |
| 400130 | 19 | 2 | 10 | 1 | 8 | 2 | 2'-MOE | 2'-MOE | 2'-MOE | H | H |

Single Dosage Study

In vivo studies were performed using positionally modified oligomeric compounds having at least 16 2'-F modified nucleotides in an internal region. The oligomeric compounds comprised the sequence of SEQ ID NO: 19. The oligomeric compounds tested included ISIS 393206, ISIS 400124, 400125, 400126, 400127, 400128, 400129, and 400130. The oligomeric compounds were intraperitoneally administered to mice at a dose of 25 mg/kg, twice per week, for 3 weeks. ISIS 393206 was also administered. ALDOA mRNA levels in livers of oligomeric compound-treated mice

TABLE B

| | ALDOA % saline | SD | GYS1 % saline | SD | CHOL % baseline | SD |
|---|---|---|---|---|---|---|
| 393206-11 mg/kg | 178 | 25 | 141 | 12 | 71 | 8 |
| 393206-33 mg/kg | 212 | 73 | 163 | 21 | 87 | 12 |
| 393206-100 mg/kg | 445 | 116 | 259 | 60 | 58 | 6 |
| 400124-11 mg/kg | 151 | 51 | 129 | 16 | 90 | 11 |
| 400124-33 mg/kg | 279 | 121 | 193 | 84 | 70 | 10 |

TABLE B-continued

| | ALDOA % saline | SD | GYS1 % saline | SD | CHOL % baseline | SD |
|---|---|---|---|---|---|---|
| 400124-100 mg/kg | 242 | 94 | 180 | 45 | 89 | 8 |
| 400125-11 mg/kg | 104 | 13 | 97 | 7 | 107 | 6 |
| 400125-33 mg/kg | 242 | 86 | 144 | 23 | 86 | 4 |
| 400125-100 mg/kg | 447 | 21 | 237 | 4 | 73 | 6 |
| 400126-11 mg/kg | 166 | 7 | 108 | 4 | 84 | 3 |
| 400126-33 mg/kg | 274 | 27 | 152 | 16 | 72 | 5 |
| 400126-100 mg/kg | 454 | 5 | 270 | 8 | 66 | 5 |
| 400127-11 mg/kg | 400 | 43 | 224 | 15 | 69 | 6 |
| 400127-33 mg/kg | 419 | 112 | 232 | 42 | 78 | 7 |
| 327895-11 mg/kg | 107 | 2 | 126 | 8 | 100 | 3 |
| 327895-33 mg/kg | 104 | 11 | 137 | 7 | 96 | 2 |
| 327895-100 mg/kg | 169 | 28 | 147 | 17 | 80 | 6 |

As has been described herein, the uniform 2'-MOE compound increased ALDOA mRNA levels at the highest dose (approx. 2-fold), and increased GYS1 mRNA at each dose tested (approx. 1.5- to 2-fold). ISIS 393206, 400125, and 400126 at the 100 mg/kg dose increased ALDOA mRNA levels by approximately 4-fold. Notably, ISIS 400127 at both the 11 and 33 mg/kg (100 mg/kg was not assayed due to technical problems) increased ALDOA mRNA by approximately 4-fold, which is comparable to the increases observed with the highest doses of other compounds. ISIS 400125 and 400126 resulted in comparable increases in ALDOA mRNA. ISIS 400124 also increased ALDOA levels.

As was observed in the single dosage study, the introduction of 2'-modifications other than 2'-F into the internal region of a chimeric oligomeric compound ameliorated immunostimulatory activity, as evidenced by a lack of increase in spleen weights.

These data demonstrate that the oligomeric compounds of the invention exhibit potent activity and improved therapeutic index. As such, the oligomeric compounds, targeted to miRNAs, possess therapeutically desirable properties, including efficacy and potency.

What is claimed:

1. An oligomeric compound comprising a contiguous sequence of nucleotides having the formula:
   5'-MMmmMmMMMmmmmMMMMmmmmm-3' or
   5'-MMmMMmMMmMMmMMmMMmMMmMM-3',
   wherein
   M and m are each 2'-modified nucleosides, wherein the 2'-modified nucleosides of M and m are not the same.

2. The oligomeric compound of claim 1, wherein
   M is a 2'-MOE modified nucleoside and
   m is a bicyclic sugar modified nucleoside.

3. The oligomeric compound of claim 1, wherein
   M is a 2'-MOE modified nucleoside,
   m is a bicyclic sugar modified nucleoside having a 4'-$(CH_2)_n$—O-2' bridge, and
   n is 1 or 2.

4. The oligomeric compound of claim 1, wherein
   M is a 2'-MOE modified nucleoside and
   m is a 2'-F modified nucleoside.

5. The oligomeric compound of claim 1, wherein
   M is a 2'-OMe modified nucleoside and
   m is a 2'-F modified nucleoside.

6. The oligomeric compound of claim 1, wherein M is a 2'-modified nucleoside that comprises a 2'-substituent group selected from O—$C_1$-$C_{12}$ alkyl, substituted O—$C_1$-$C_{12}$ alkyl, O—$C_2$-$C_{12}$ alkenyl, substituted O—$C_2$-$C_{12}$ alkenyl, O—$C_2$-$C_{12}$ alkynyl, substituted O—$C_2$-$C_{12}$ alkynyl, amino, substituted amino, amide, substituted amide, aralkyl, substituted aralkyl, O-aralkyl, substituted O-aralkyl, $N_3$, SH, CN, OCN, $CF_3$, $OCF_3$, $SOCH_3$, —$SO_2CH_3$, heterocycloalkyl, heterocycloalkaryl, aminoalkylamino and polyalkylamino; and wherein each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, O—$C_1$-$C_{12}$ alkyl, substituted O—$C_1$-$C_{12}$ alkyl, S—$C_1$-$C_{12}$ alkyl, substituted S—$C_1$-$C_{12}$ alkyl, acyl (C(=O)—H), substituted acyl, amino, substituted amino, amide, substituted amide, $C_1$-$C_{12}$ alkylamino, substituted $C_1$-$C_{12}$ alkylamino, $C_1$-$C_{12}$ aminoalkoxy, substituted $C_1$-$C_{12}$ aminoalkoxy, $C_1$-$C_{12}$ alkylaminooxy, substituted $C_1$-$C_{12}$ alkylaminooxy, guanidinyl, substituted guanidinyl or a protecting group.

7. The oligomeric compound of claim 6 wherein M is a 2'-modified nucleoside that independently comprises a 2'-substituent group selected from $O(CH_2)_{0-2}CH_3$, $O(CH_2)_2OCH_3$, $O(CH_2)_2SCH_3$, $OCH_2C(H)CH_2$, $O(CH_2)_2ON(CH_3)_2$ and $OCH_2C(=O)N(H)CH_3$.

8. The oligomeric compound of claim 7, wherein m is a bicyclic sugar modified nucleoside.

9. The oligomeric compound of claim 7, wherein m is a 2'-F modified nucleoside.

10. The oligomeric compound of claim 1 wherein m is a bicyclic sugar modified nucleoside that independently comprises a bridge group between the 2' and the 4'-carbon atoms comprising from 1 to 8 linked biradical groups independently selected from —O—, —S—, —N($R_1$)—, —C($R_1$)($R_2$)—, —C($R_1$)=C($R_1$)—, —C(=N$R_1$)—, —S(=O)$_2$—, —S(=O)—, —C(=O)— and —C(=S)—;

each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and wherein each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

11. The oligomeric compound of claim 10, wherein M is a 2'-MOE modified nucleoside.

12. The oligomeric compound of claim 1, wherein M is a 2'-F modified nucleoside.

13. The oligomeric compound of claim 12, wherein M is a bicyclic sugar modified nucleoside.

14. The oligomeric compound of claim 1, comprising at least one phosphorothioate internucleoside linkage group.

15. The oligomeric compound of claim 14, wherein each internucleoside linkage group is a phosphorothioate internucleoside linkage group.

\* \* \* \* \*

```
                        SEQUENCE LISTING

<160> NUMBER OF SEQ ID NOS: 470

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 1
aactatacaa cctactacct ca                                             22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 2
aaccacacaa cctactacct ca                                             22

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 3
aaccatacaa cctactacct ca                                             22

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 4
actatgcaac ctactacctc t                                              21

<210> SEQ ID NO 5
<211> LENGTH: 21
```

```
<212> TYPE: DNA
<213> ORGANISM: Artificial Sequence
<220> FEATURE:
<223> OTHER INFORMATION: Synthetic Oligomeric Compound

<400> SEQUENCE: 5
actatacaac ctcctacctc a                                              21

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 6
aactatacaa tctactacct ca                                             22

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 7
actgtacaaa ctactacctc a                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 8
acagcacaaa ctactacctc a                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 9
tacatacttc tttacattcc a                                              21

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 10
cacaagttcg gatctacggg tt                                             22

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 11
```

```
cttcagttat cacagtactg ta                                                  22

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 12
tcatagccct gtacaatgct gct                                                 23

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 13
acaggagtct gagcatttga                                                     20

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 14
gctacctgca ctgtaagcac tttt                                                24

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 15
atctgcactg tcagcacttt a                                                   21

<210> SEQ ID NO 16
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 16
tgatagccct gtacaatgct gct                                                 23

<210> SEQ ID NO 17
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 17
cacaaattcg gatctacagg gta                                                 23

<210> SEQ ID NO 18
<211> LENGTH: 22
<212> TYPE: DNA
<213> ORGANISM: Artificial Sequence
```

```
<220> FEATURE:
<223> OTHER INFORMATION: Synthetic Oligomeric Compound

<400> SEQUENCE: 18
acaaattcgg ttctacaggg ta                                              22

<210> SEQ ID NO 19
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 19
acaaacacca ttgtcacact cca                                             23

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 20
tggcattcac cgcgtgcctt aa                                              22

<210> SEQ ID NO 21
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 21
cacaggttaa agggtctcag gga                                             23

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 22
tcacaagtta gggtctcagg ga                                              22

<210> SEQ ID NO 23
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 23
gcattattac tcacggtacg a                                               21

<210> SEQ ID NO 24
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 24
cgcgtaccaa aagtaataat g                                               21
```

```
<210> SEQ ID NO 25
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 25
agccaagctc agacggatcc ga                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 26
aaaagagacc ggttcactgt ga                                              22

<210> SEQ ID NO 27
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 27
gaaagagacc ggttcactgt ga                                              22

<210> SEQ ID NO 28
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 28
gcaagcccag accgcaaaaa g                                               21

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 29
atgccctttt aacattgcac tg                                              22

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 30 atgcccttc atcattgcac tg                                               22

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligomeric Compound
```

```
<400> SEQUENCE: 31
cgaccatggc tgtagactgt ta                                              22

<210> SEQ ID NO 32
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 32
acagctggtt gaaggggacc aa                                              22

<210> SEQ ID NO 33
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 33
tagctggttg aagggggacca a                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 34
ccctctggtc aaccagtcac a                                               21

<210> SEQ ID NO 35
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 35
tcacatagga ataaaaagcc ata                                             23

<210> SEQ ID NO 36
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 36
cacataggaa tgaaaagcca ta                                              22

<210> SEQ ID NO 37
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 37
tccatcatca aaacaaatgg agt                                             23

<210> SEQ ID NO 38
```

```
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 38
ctacgcgtat tcttaagcaa ta                                          22

<210> SEQ ID NO 39
<211> LENGTH: 17
<212> TYPE: DNA
<213> ORGANISM: Artificial Sequence
<220> FEATURE:
<223> OTHER INFORMATION: Synthetic Oligomeric Compound

<400> SEQUENCE: 39
gattcacaac accagct                                                17

<210> SEQ ID NO 40
<211> LENGTH: 18
<212> TYPE: DNA
<213> ORGANISM: Artificial Sequence
<220> FEATURE:
<223> OTHER INFORMATION: Synthetic Oligomeric Compound

<400> SEQUENCE: 40
agacacgtgc actgtaga                                               18

<210> SEQ ID NO 41
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 41
ctaccatagg gtaaaaccac t                                           21

<210> SEQ ID NO 42
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 42
ccatctttac cagacagtgt ta                                          22

<210> SEQ ID NO 43
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 43
tccataaagt aggaaacact aca                                         23

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 44
```

-continued gtagtgctttt ctactttatg                                       20

<210> SEQ ID NO 45
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 45
tgagctacag tgcttcatct ca                                     22

<210> SEQ ID NO 46
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 46
ctagtacatc atctatactg ta                                     22

<210> SEQ ID NO 47
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 47
aagggattcc tgggaaaact ggac                                   24

<210> SEQ ID NO 48
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 48
aacccatgga attcagttct ca                                     22

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 49
agcctatgga attcagttct ca                                     22

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 50
gcagaagcat ttccacacac                                        20

<210> SEQ ID NO 51
<211> LENGTH: 22
<212> TYPE: DNA

```
<213> ORGANISM: Artificial Sequence
<220> FEATURE:
<223> OTHER INFORMATION: Synthetic Oligomeric Compound

<400> SEQUENCE: 51
acaaagttct gtagtgcact ga                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 52
acaaagttct gtgatgcact ga                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 53
ggagtgaaga cacggagcca ga                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 54
cactggtaca agggttggga ga                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 55
cctcaaggag cttcagtcta gt                                              22

<210> SEQ ID NO 56
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 56
cccaagttct gtcatgcact ga                                              22

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 57
tcactttTgt gactatgcaa                                                 20
```

<210> SEQ ID NO 58
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 58
cgaaggcaac acggataacc ta                                              22

<210> SEQ ID NO 59
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 59
aataggtcaa ccgtgtatga tt                                              22

<210> SEQ ID NO 60
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 60
cccctatcac gattagcatt aa                                              22

<210> SEQ ID NO 61
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 61
cacaaaccat tatgtgctgc ta                                              22

<210> SEQ ID NO 62
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 62
tgtaaaccat gatgtgctgc ta                                              22

<210> SEQ ID NO 63
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 63
cgccaatatt tacgtgctgc ta                                              22

<210> SEQ ID NO 64
<211> LENGTH: 20
<212> TYPE: DNA
<213> ORGANISM: Artificial Sequence
<220> FEATURE:

<223> OTHER INFORMATION: Synthetic Oligomeric Compound

<400> SEQUENCE: 64
acaagtgcct tcactgcagt						20

<210> SEQ ID NO 65
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 65
actacctgca ctgtaagcac tttg					24

<210> SEQ ID NO 66
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 66
actcaccgac agcgttgaat gtt					23

<210> SEQ ID NO 67
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 67
ggtacaatca acggtcgatg gt					22

<210> SEQ ID NO 68
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 68
cccaccgaca gcaatgaatg tt					22

<210> SEQ ID NO 69
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 69
actcaccgac aggttgaatg tt					22

<210> SEQ ID NO 70
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 70
aacccaccga caacaatgaa tgtt					24

```
<210> SEQ ID NO 71
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 71
tgtgagttct accattgcca aa                                             22

<210> SEQ ID NO 72
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 72
tagttggcaa gtctagaacc a                                              21

<210> SEQ ID NO 73
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 73
cagtgaattc taccagtgcc ata                                            23

<210> SEQ ID NO 74
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 74
acccttatca gttctccgtc ca                                             22

<210> SEQ ID NO 75
<211> LENGTH: 18
<212> TYPE: DNA
<213> ORGANISM: Artificial Sequence
<220> FEATURE:
<223> OTHER INFORMATION: Synthetic Oligomeric Compound

<400> SEQUENCE: 75
gaactgcctt tctctcca                                                  18

<210> SEQ ID NO 76
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 76
aagcccaaaa ggagaattct ttg                                            23

<210> SEQ ID NO 77
<211> LENGTH: 21
<212> TYPE: DNA
<213> ORGANISM: Artificial Sequence
<220> FEATURE:
<223> OTHER INFORMATION: Synthetic Oligomeric Compound
```

```
<400> SEQUENCE: 77
cggctgcaac acaagacacg a                                              21

<210> SEQ ID NO 78
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 78
accctccacc atgcaaggga tg                                             22

<210> SEQ ID NO 79
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 79
actgatatca gctcagtagg cac                                            23

<210> SEQ ID NO 80
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 80
tatctgcact agatgcacct ta                                             22

<210> SEQ ID NO 81
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 81
agaaggagca cttagggcag t                                              21

<210> SEQ ID NO 82
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 82
taactgcact agatgcacct ta                                             22

<210> SEQ ID NO 83
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 83
acctaatata tcaaacatat ca                                             22

<210> SEQ ID NO 84
<211> LENGTH: 22
```

-continued

<210> SEQ ID NO 84
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 84
agctgctttt gggattccgt tg                                              22

<210> SEQ ID NO 85
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 85
ggggacgaaa tccaagcgca gc                                              22

<210> SEQ ID NO 86
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 86
ggctgtcaat tcataggtca g                                               21

<210> SEQ ID NO 87
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 87
ctgggacttt gtaggccagt t                                               21

<210> SEQ ID NO 88
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 88
aaagcgggac tttgagggcc agtt                                            24

<210> SEQ ID NO 89
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 89
tccacatgga gttgctgtta ca                                              22

<210> SEQ ID NO 90
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 90

```
gccaatattt ctgtgctgct a                                              21
```

<210> SEQ ID NO 91
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 91

```
ccaacaacat gaaactacct a                                              21
```

<210> SEQ ID NO 92
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 92

```
ccaacaacag gaaactacct a                                              21
```

<210> SEQ ID NO 93
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 93

```
gctgggtgga gaaggtggtg aa                                             22
```

<210> SEQ ID NO 94
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 94

```
cctatctccc ctctggacc                                                 19
```

<210> SEQ ID NO 95
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 95

```
gaacaggtag tctgaacact ggg                                            23
```

<210> SEQ ID NO 96
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 96

```
aaccaatgtg cagactactg ta                                             22
```

<210> SEQ ID NO 97
<211> LENGTH: 23
<212> TYPE: DNA
<213> ORGANISM: Artificial Sequence

```
<220> FEATURE:
<223> OTHER INFORMATION: Synthetic Oligomeric Compound

<400> SEQUENCE: 97
gaacagatag tctaaacact ggg                                              23

<210> SEQ ID NO 98
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 98
tcagttttgc atagatttgc aca                                              23

<210> SEQ ID NO 99
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 99
tcagttttgc atggatttgc aca                                              23

<210> SEQ ID NO 100
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 100
acatcgttac cagacagtgt ta                                               22

<210> SEQ ID NO 101
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 101
tccagcactg tccggtaaga tg                                               22

<210> SEQ ID NO 102
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 102
gtcatcatta ccaggcagta tta                                              23

<210> SEQ ID NO 103
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 103
ccatcattac ccggcagtat ta                                               22
```

```
<210> SEQ ID NO 104
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 104
ttttcccatg ccctatacct ct                                               22

<210> SEQ ID NO 105
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 105
aaagaagtat atgcatagga aa                                               22

<210> SEQ ID NO 106
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 106
ctagtggtcc taaacatttc ac                                               22

<210> SEQ ID NO 107
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 107
aggcatagga tgacaaaggg aa                                               22

<210> SEQ ID NO 108
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 108
cagactccgg tggaatgaag ga                                               22

<210> SEQ ID NO 109
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 109
ccacacactt ccttacattc ca                                               22

<210> SEQ ID NO 110
<211> LENGTH: 22
<212> TYPE: DNA
<213> ORGANISM: Artificial Sequence
<220> FEATURE:
<223> OTHER INFORMATION: Synthetic Oligomeric Compound
```

```
<400> SEQUENCE: 110
acaagctttt tgctcgtctt at                                              22

<210> SEQ ID NO 111
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 111
ctacctgcac tataagcact tta                                             23

<210> SEQ ID NO 112
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 112
ctacctgcac tatgagcact ttg                                             23

<210> SEQ ID NO 113
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 113
tcaacatcag tctgataagc ta                                              22

<210> SEQ ID NO 114
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 114
tcagccgctg tcacacgcac ag                                              22

<210> SEQ ID NO 115
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 115
aggcgaagga tgacaaaggg aa                                              22

<210> SEQ ID NO 116
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 116
ggccgtgact ggagactgtt a                                               21

<210> SEQ ID NO 117
```

```
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 117
ctgcctgtct gtgcctgctg t                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 118
gtctgtcaat tcataggtca t                                              21

<210> SEQ ID NO 119
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 119
cacagttgcc agctgagatt a                                              21

<210> SEQ ID NO 120
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 120
atccaatcag ttcctgatgc agta                                           24

<210> SEQ ID NO 121
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 121
acatggttag atcaagcaca a                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 122
agaattgcgt ttggacaatc a                                              21

<210> SEQ ID NO 123
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 123
```
acagttcttc aactggcagc tt                                             22

<210> SEQ ID NO 124
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 124
aaagtgtcag atacggtgtg g                                              21

<210> SEQ ID NO 125
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 125
gaaacccagc agacaatgta gct                                            23

<210> SEQ ID NO 126
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 126
gagacccagt agccagatgt agct                                           24

<210> SEQ ID NO 127
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 127
ggggtatttg acaaactgac a                                              21

<210> SEQ ID NO 128
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 128
taaacggaac cactagtgac ttg                                            23

<210> SEQ ID NO 129
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 129
ggaaatccct ggcaatgtga t                                              21

<210> SEQ ID NO 130
<211> LENGTH: 21
<212> TYPE: DNA

```
<213> ORGANISM: Artificial Sequence
<220> FEATURE:
<223> OTHER INFORMATION: Synthetic Oligomeric Compound

<400> SEQUENCE: 130
ggtaatccct ggcaatgtga t                                              21

<210> SEQ ID NO 131
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 131
ctgttcctgc tgaactgagc ca                                             22

<210> SEQ ID NO 132
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 132
tcagaccgag acaagtgcaa tg                                             22

<210> SEQ ID NO 133
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 133
gcctatcctg gattacttga a                                              21

<210> SEQ ID NO 134
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 134
aacctatcct gaattacttg aa                                             22

<210> SEQ ID NO 135
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 135
gcggaactta gccactgtga a                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 136
gcagaactta gccactgtga a                                              21
```

<210> SEQ ID NO 137
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 137
ctcaatagac tgtgagctcc tt                                           22

<210> SEQ ID NO 138
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 138
acaggattga gggggggccc t                                            21

<210> SEQ ID NO 139
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 139
aagcggttta ccatcccaca ta                                           22

<210> SEQ ID NO 140
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 140
atgtatgtgg gacggtaaac ca                                           22

<210> SEQ ID NO 141
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 141
aaccgatttc agatggtgct a                                            21

<210> SEQ ID NO 142
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 142
aacactgatt tcaaatggtg cta                                          23

<210> SEQ ID NO 143
<211> LENGTH: 20
<212> TYPE: DNA
<213> ORGANISM: Artificial Sequence
<220> FEATURE:

```
<223> OTHER INFORMATION: Synthetic Oligomeric Compound

<400> SEQUENCE: 143
accgatttca aatggtgcta                                              20

<210> SEQ ID NO 144
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 144
gctttgacaa tactattgca ctg                                          23

<210> SEQ ID NO 145
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 145
tcaccaaaac atggaagcac tta                                          23

<210> SEQ ID NO 146
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 146
aaagcaagta catccacgtt ta                                           22

<210> SEQ ID NO 147
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 147
ctactaaaac atggaagcac tta                                          23

<210> SEQ ID NO 148
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 148
agaaagcact tccatgttaa agt                                          23

<210> SEQ ID NO 149
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 149
ccactgaaac atggaagcac tta                                          23
```

```
<210> SEQ ID NO 150
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 150
cagcaggtac ccccatgtta aa                                              22

<210> SEQ ID NO 151
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 151
acactcaaac atggaagcac tta                                             23

<210> SEQ ID NO 152
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 152
gctgcaaaca tccgactgaa ag                                              22

<210> SEQ ID NO 153
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 153
cttccagtcg aggatgttta ca                                              22

<210> SEQ ID NO 154
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 154
agctgagtgt aggatgttta ca                                              22

<210> SEQ ID NO 155
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 155
gctgagagtg taggatgttt aca                                             23

<210> SEQ ID NO 156
<211> LENGTH: 22
<212> TYPE: DNA
<213> ORGANISM: Artificial Sequence
<220> FEATURE:
<223> OTHER INFORMATION: Synthetic Oligomeric Compound
```

```
<400> SEQUENCE: 156
cttccagtcg gggatgttta ca                                              22

<210> SEQ ID NO 157
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 157
gctgtaaaca tccgactgaa ag                                              22

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 158
tccagtcaag gatgtttaca                                                 20

<210> SEQ ID NO 159
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 159
cagctatgcc agcatcttgc c                                               21

<210> SEQ ID NO 160
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 160
gcaacttagt aatgtgcaat a                                               21

<210> SEQ ID NO 161
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 161
ttcgccctct caacccagct ttt                                             23

<210> SEQ ID NO 162
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 162
agaggtcgac cgtgtaatgt gc                                              22

<210> SEQ ID NO 163
<211> LENGTH: 22
```

<210> SEQ ID NO 164
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 163
ccagcagcac ctggggcagt gg                                    22

<210> SEQ ID NO 164
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 164
acaccaatgc cctaggggat gcg                                   23

<210> SEQ ID NO 165
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 165
acacttactg gacacctact agg                                   23

<210> SEQ ID NO 166
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 166
ctggaggaag ggcccagagg                                       20

<210> SEQ ID NO 167
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 167
acggaagggc agagagggcc ag                                    22

<210> SEQ ID NO 168
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 168
aaagaggtta accaggtgtg tt                                    22

<210> SEQ ID NO 169
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 169
caatgcaact acaatgcac                                                  19

<210> SEQ ID NO 170
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 170
tctctgcagg ccgtgtgctt tgc                                             23

<210> SEQ ID NO 171
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 171
ttctaggata ggcccagggg c                                               21

<210> SEQ ID NO 172
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 172
acatttttcg ttattgctct tga                                             23

<210> SEQ ID NO 173
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 173
aaaggcatca tataggagct gga                                             23

<210> SEQ ID NO 174
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 174
tcaacaaaat cactgatgct gga                                             23

<210> SEQ ID NO 175
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 175
tgagctcctg gaggacaggg a                                               21

<210> SEQ ID NO 176
<211> LENGTH: 21
<212> TYPE: DNA
<213> ORGANISM: Artificial Sequence

```
<220> FEATURE:
<223> OTHER INFORMATION: Synthetic Oligomeric Compound

<400> SEQUENCE: 176
tgcaatgcaa cagcaatgca c                                              21

<210> SEQ ID NO 177
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 177
ggctataaag taactgagac gga                                            23

<210> SEQ ID NO 178
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 178
gacgggtgcg atttctgtgt gaga                                           24

<210> SEQ ID NO 179
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 179
gccctggact aggagtcagc a                                              21

<210> SEQ ID NO 180
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 180
agaggcaggc atgcgggcag aca                                            23

<210> SEQ ID NO 181
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 181
aacaaccagc taagacactg cca                                            23

<210> SEQ ID NO 182
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 182
caatcagcta atgacactgc cta                                            23
```

<210> SEQ ID NO 183
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 183
gcaatcagct aactacactg cct					23

<210> SEQ ID NO 184
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 184
gtacccctgg agattctgat aa					22

<210> SEQ ID NO 185
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 185
actcacacct aggttccaag gatt					24

<210> SEQ ID NO 186
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 186
tacagatgga taccgtgcaa tt					22

<210> SEQ ID NO 187
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 187
aaattgcatc gtgatccacc cg					22

<210> SEQ ID NO 188
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 188
ataaggattt ttagggcat ta					22

<210> SEQ ID NO 189
<211> LENGTH: 22
<212> TYPE: DNA
<213> ORGANISM: Artificial Sequence
<220> FEATURE:
<223> OTHER INFORMATION: Synthetic Oligomeric Compound -continued

<400> SEQUENCE: 189
tcaccattgc taaagtgcaa tt                                              22

<210> SEQ ID NO 190
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 190
aaacgtggaa tttcctctat gt                                              22

<210> SEQ ID NO 191
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 191
aaagatcaac catgtattat t                                               21

<210> SEQ ID NO 192
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 192
gcgaatataa cacggtcgat ct                                              22

<210> SEQ ID NO 193
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 193
ccaggttcca ccccagcagg c                                               21

<210> SEQ ID NO 194
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 194
acactcaaaa gatggcggca c                                               21

<210> SEQ ID NO 195
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 195
acgctcaaat gtcgcagcac ttt                                             23

<210> SEQ ID NO 196

```
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 196
acaccccaaa atcgaagcac ttc                                            23

<210> SEQ ID NO 197
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 197
ggaaagcgcc cccattttga gt                                             22

<210> SEQ ID NO 198
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 198
cacttatcag gttgtattat aa                                             22

<210> SEQ ID NO 199
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 199
tcacgcgagc cgaacgaaca aa                                             22

<210> SEQ ID NO 200
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 200
acgtggattt tcctctatga t                                              21

<210> SEQ ID NO 201
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 201
ctcatagaag gagaatctac c                                              21

<210> SEQ ID NO 202
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 202
```
aacatggatt ttcctctatg at                                              22

<210> SEQ ID NO 203
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 203
acaaaagttg cctttgtgtg at                                              22

<210> SEQ ID NO 204
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 204
acacaggacc tggagtcagg ag                                              22

<210> SEQ ID NO 205
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 205
tacgttccat agtctacca                                                  19

<210> SEQ ID NO 206
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 206
aagatgtgga ccatattaca ta                                              22

<210> SEQ ID NO 207
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 207
gcgcatgttc tatggtcaac ca                                              22

<210> SEQ ID NO 208
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 208
acagagagct tgcccttgta ta                                              22

<210> SEQ ID NO 209
<211> LENGTH: 22
<212> TYPE: DNA

```
<213> ORGANISM: Artificial Sequence
<220> FEATURE:
<223> OTHER INFORMATION: Synthetic Oligomeric Compound

<400> SEQUENCE: 209
cgaatccacc acgaacaact tc                                              22

<210> SEQ ID NO 210
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 210
agccacaatc accttctgat ct                                              22

<210> SEQ ID NO 211
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 211
tatgaacaat ttctaggaat                                                 20

<210> SEQ ID NO 212
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 212
aggggttcac cgagcaacat tcg                                             23

<210> SEQ ID NO 213
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 213
tgcaaagttg ctcgggtaac ct                                              22

<210> SEQ ID NO 214
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 214
acaggccatc tgtgttatat t                                               21

<210> SEQ ID NO 215
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 215
cgtacgctat acggtctact a                                               21
```

<210> SEQ ID NO 216
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 216
acggctagtg gaccaggtga agt                                    23

<210> SEQ ID NO 217
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 217
gcgcccaatt aatgtctgtt gat                                    23

<210> SEQ ID NO 218
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 218
ggccttctga ccctaagtcc ag                                     22

<210> SEQ ID NO 219
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 219
ggccttctga ctccaagtcc ag                                     22

<210> SEQ ID NO 220
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 220
ctgaggggcc tcagaccgag ct                                     22

<210> SEQ ID NO 221
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 221
ttcaaaacat gaattgctgc tg                                     22

<210> SEQ ID NO 222
<211> LENGTH: 21
<212> TYPE: DNA
<213> ORGANISM: Artificial Sequence
<220> FEATURE:

```
<223> OTHER INFORMATION: Synthetic Oligomeric Compound

<400> SEQUENCE: 222
ggcggacacg acattcccga t                                          21

<210> SEQ ID NO 223
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 223
tcaacgggag tgatcgtgtc att                                        23

<210> SEQ ID NO 224
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 224
acggttttac cagacagtat ta                                         22

<210> SEQ ID NO 225
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 225
tgcatgacgg cctgcaagac a                                          21

<210> SEQ ID NO 226
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 226
ccacccaatg acctactcca aga                                        23

<210> SEQ ID NO 227
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 227
agacatggag gagccatcca g                                          21

<210> SEQ ID NO 228
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 228
acaccgagga gcccatcatg at                                         22
```

```
<210> SEQ ID NO 229
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 229
atgggacatc ctacatatgc aa                                              22

<210> SEQ ID NO 230
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 230
accagctaac aatacactgc ca                                              22

<210> SEQ ID NO 231
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 231
gccagctaac aatacactgc ct                                              22

<210> SEQ ID NO 232
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 232
tattaggaac acatcgcaaa aa                                              22

<210> SEQ ID NO 233
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 233
aaactcagta atggtaacgg ttt                                             23

<210> SEQ ID NO 234
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 234
gtctcagttt cctctgcaaa ca                                              22

<210> SEQ ID NO 235
<211> LENGTH: 21
<212> TYPE: DNA
<213> ORGANISM: Artificial Sequence
<220> FEATURE:
<223> OTHER INFORMATION: Synthetic Oligomeric Compound
```

```
<400> SEQUENCE: 235
cttctttgca gatgagactg a                                      21

<210> SEQ ID NO 236
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 236
cgaactcacc acggacaacc tc                                     22

<210> SEQ ID NO 237
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 237
aaaccctata agcaatattg cacta                                  25

<210> SEQ ID NO 238
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 238
gcagagacaa tattgatagg gt                                     22

<210> SEQ ID NO 239
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 239
cgatgtagtc caaaggcaca ta                                     22

<210> SEQ ID NO 240
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 240
agaagacggg aggagaggag tga                                    23

<210> SEQ ID NO 241
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 241
atcgggaggg gactgagcct ga                                     22

<210> SEQ ID NO 242
<211> LENGTH: 22
```

```
<212> TYPE: DNA
<213> ORGANISM: Artificial Sequence
<220> FEATURE:
<223> OTHER INFORMATION: Synthetic Oligomeric Compound

<400> SEQUENCE: 242
agagaggaga gccgtgtatg ac                                              22

<210> SEQ ID NO 243
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 243
gaattcatca cggccagcct ct                                              22

<210> SEQ ID NO 244
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 244
ctcggggcag ctcagtacag ga                                              22

<210> SEQ ID NO 245
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 245
aactggatgt ccctgtatga tt                                              22

<210> SEQ ID NO 246
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 246
aagtggatga ccctgtacga tt                                              22

<210> SEQ ID NO 247
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 247
ttgagagtgc cattatctgg g                                               21

<210> SEQ ID NO 248
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 248
```
gctgccgtat atgtgatgtc act 23

<210> SEQ ID NO 249
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 249
cagcatggag tcctccaggt tg 22

<210> SEQ ID NO 250
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 250
tcctcatgga agggttcccc act 23

<210> SEQ ID NO 251
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 251
aagaatcttg tcccgcaggt cct 23

<210> SEQ ID NO 252
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 252
ctggcacaca gtagaccttc a 21

<210> SEQ ID NO 253
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 253
aatgaaagcc taccatgtac aa 22

<210> SEQ ID NO 254
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 254
aagaggtttc ccgtgtatgt ttca 24

<210> SEQ ID NO 255
<211> LENGTH: 23
<212> TYPE: DNA
<213> ORGANISM: Artificial Sequence

```
<220> FEATURE:
<223> OTHER INFORMATION: Synthetic Oligomeric Compound

<400> SEQUENCE: 255
aaagaagtgc accatgtttg ttt                                              23

<210> SEQ ID NO 256
<211> LENGTH: 17
<212> TYPE: DNA
<213> ORGANISM: Artificial Sequence
<220> FEATURE:
<223> OTHER INFORMATION: Synthetic Oligomeric Compound

<400> SEQUENCE: 256
gagattggcc atgtaat                                                     17

<210> SEQ ID NO 257
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 257
acaaaccaca gtgtgctgct g                                                21

<210> SEQ ID NO 258
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 258
gaaaaacgcc ccctggcttg aaa                                              23

<210> SEQ ID NO 259
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 259
ttaaacatca ctgcaagtct taa                                              23

<210> SEQ ID NO 260
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 260
cagaatcctt gcccaggtgc at                                               22

<210> SEQ ID NO 261
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 261
tctcacccag ggacaaagga tt                                               22
```

<210> SEQ ID NO 262
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 262
tagcacccag atagcaagga t                                              21

<210> SEQ ID NO 263
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 263
ctgcagaact gttcccgctg cta                                            23

<210> SEQ ID NO 264
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 264
atagagtgca gaccagggtc t                                              21

<210> SEQ ID NO 265
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 265
gaggaaacca gcaagtgttg ac                                             22

<210> SEQ ID NO 266
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 266
tctactcaga agggtgcctt a                                              21

<210> SEQ ID NO 267
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 267
ttcactccaa aaggtgcaaa a                                              21

<210> SEQ ID NO 268
<211> LENGTH: 23
<212> TYPE: DNA
<213> ORGANISM: Artificial Sequence
<220> FEATURE:
<223> OTHER INFORMATION: Synthetic Oligomeric Compound

```
<400> SEQUENCE: 268
tctactccaa aaggctacaa tca                                          23

<210> SEQ ID NO 269
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 269
tctacccaca gacgtaccaa tca                                          23

<210> SEQ ID NO 270
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 270
tgtgattgcc actctcctga gta                                          23

<210> SEQ ID NO 271
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 271
tgactgcaga gcaaaagaca c                                            21

<210> SEQ ID NO 272
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 272
gacctcagct atgacagcac tt                                           22

<210> SEQ ID NO 273
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 273
gaaagtgccc tcaaggctga gtg                                          23

<210> SEQ ID NO 274
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 274
ataaatgaca cctccctgtg aa                                           22

<210> SEQ ID NO 275
```

```
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 275
ctactcacag aagtgtcaat                                              20

<210> SEQ ID NO 276
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 276
acgctccaaa agaaggcact c                                            21

<210> SEQ ID NO 277
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 277
cagaaagtgc tttcttttgg agaa                                         24

<210> SEQ ID NO 278
<211> LENGTH: 18
<212> TYPE: DNA
<213> ORGANISM: Artificial Sequence
<220> FEATURE:
<223> OTHER INFORMATION: Synthetic Oligomeric Compound

<400> SEQUENCE: 278
accctctgaa aggaagca                                                18

<210> SEQ ID NO 279
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 279
aaagtgcttc ttacctccag atg                                          23

<210> SEQ ID NO 280
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 280
agacagtgct tccatctaga gg                                           22

<210> SEQ ID NO 281
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 281
```

```
aacactctaa agggatgcac gat                                              23

<210> SEQ ID NO 282
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 282
aacactctaa agggatgcac ga                                               22

<210> SEQ ID NO 283
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 283
acactctaaa aggatgcacg at                                               22

<210> SEQ ID NO 284
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 284
tccagcaaag ggaagcgctt t                                                21

<210> SEQ ID NO 285
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 285
acctctaaag gggagcgctt tg                                               22

<210> SEQ ID NO 286
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 286
cactctaaag agaagcgctt tg                                               22

<210> SEQ ID NO 287
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 287
cagaaagtgc ttccctccag aga                                              23

<210> SEQ ID NO 288
<211> LENGTH: 21
<212> TYPE: DNA
```

```
<213> ORGANISM: Artificial Sequence
<220> FEATURE:
<223> OTHER INFORMATION: Synthetic Oligomeric Compound

<400> SEQUENCE: 288
gctccaaagg gaagcgcttt g                                          21

<210> SEQ ID NO 289
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 289
acactctgaa gggaagcgct tt                                         22

<210> SEQ ID NO 290
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 290
tcctctaaag agaagcgctt t                                          21

<210> SEQ ID NO 291
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 291
agagaaagtg cttccctcta gag                                        23

<210> SEQ ID NO 292
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 292
gtaacactct aaaaggatgc acttt                                      25

<210> SEQ ID NO 293
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 293
aaacctctaa aaggatgcac ttt                                        23

<210> SEQ ID NO 294
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 294
atcctctaaa aagatgcact tt                                         22
```

```
<210> SEQ ID NO 295
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 295
acactctaaa gggaggcact ttg                                              23

<210> SEQ ID NO 296
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 296
acactctaaa aggaggcact tt                                               22

<210> SEQ ID NO 297
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 297
gaaagtgctc ccttttggag aa                                               22

<210> SEQ ID NO 298
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 298
acagtccaaa gggaagcact tt                                               22

<210> SEQ ID NO 299
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 299
agaaagtact tccctctgga g                                                21

<210> SEQ ID NO 300
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 300
ccctctaaaa ggaagcactt t                                                21

<210> SEQ ID NO 301
<211> LENGTH: 23
<212> TYPE: DNA
<213> ORGANISM: Artificial Sequence
<220> FEATURE:
```

<223> OTHER INFORMATION: Synthetic Oligomeric Compound

<400> SEQUENCE: 301
aaccctctaa aaggaagcac ttt                                        23

<210> SEQ ID NO 302
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 302
aacccaccaa agagaagcac ttt                                        23

<210> SEQ ID NO 303
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 303
cagaaagggc ttccctttgt aga                                        23

<210> SEQ ID NO 304
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 304
ccctcaaaaa ggaagcactt t                                          21

<210> SEQ ID NO 305
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 305
aaccctctaa aaggaagcac tt                                         22

<210> SEQ ID NO 306
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 306
acactctaaa gggaagcact ttgt                                       24

<210> SEQ ID NO 307
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 307
actctaaagg gaagcacttt gt                                         22

```
<210> SEQ ID NO 308
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 308
acactctaaa gggaagtgcg tt                                              22

<210> SEQ ID NO 309
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 309
aacactctaa agggaaccat ttt                                             23

<210> SEQ ID NO 310
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 310
ccctctatag ggaagcgcgt t                                               21

<210> SEQ ID NO 311
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 311
actccaaagg gaagcgcctt c                                               21

<210> SEQ ID NO 312
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 312
gagaaagtgc ttccctttgt ag                                              22

<210> SEQ ID NO 313
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 313
agaaagtgca tccctctgga g                                               21

<210> SEQ ID NO 314
<211> LENGTH: 21
<212> TYPE: DNA
<213> ORGANISM: Artificial Sequence
<220> FEATURE:
<223> OTHER INFORMATION: Synthetic Oligomeric Compound
```

<400> SEQUENCE: 314
gctctaaagg gaagcgcctt c                                              21

<210> SEQ ID NO 315
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 315
agaaagtgct tccctctaga g                                              21

<210> SEQ ID NO 316
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 316
aacagaaagt gcttccctca agag                                           24

<210> SEQ ID NO 317
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 317
gcctctaaaa ggaagcactt t                                              21

<210> SEQ ID NO 318
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 318
aacagaaagc gcttccctct agag                                           24

<210> SEQ ID NO 319
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 319
agaaagggct tccctttgca g                                              21

<210> SEQ ID NO 320
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 320
acggtcctac actcaaggca tg                                             22

<210> SEQ ID NO 321
<211> LENGTH: 22

```
<212> TYPE: DNA
<213> ORGANISM: Artificial Sequence
<220> FEATURE:
<223> OTHER INFORMATION: Synthetic Oligomeric Compound

<400> SEQUENCE: 321
acacaccaag gataatttct cc                                           22

<210> SEQ ID NO 322
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 322
tttcagttat caatctgtca ca                                           22

<210> SEQ ID NO 323
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 323
ctcgtgacat gatgatcccc ga                                           22

<210> SEQ ID NO 324
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 324
acttgctaaa aatgcagaat                                              20

<210> SEQ ID NO 325
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 325
cacacaataa atgtttgctg at                                           22

<210> SEQ ID NO 326
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 326
gcaaaagtaa ttgccagttt tg                                           22

<210> SEQ ID NO 327
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 327
```

```
acaaaagcaa ctgaggttct tg                                              22

<210> SEQ ID NO 328
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 328
gcaaaagtaa ttgagatttt tg                                              22

<210> SEQ ID NO 329
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 329
gcaaaagaaa ctgtggtttt tg                                              22

<210> SEQ ID NO 330
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 330
agagctcatc catagttgtc a                                               21

<210> SEQ ID NO 331
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 331
atgtgcctga gggagtaaga ca                                              22

<210> SEQ ID NO 332
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 332
tggaaaccaa gagtgggtcg c                                               21

<210> SEQ ID NO 333
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 333
ctgaaaccaa gtatgggtcg c                                               21

<210> SEQ ID NO 334
<211> LENGTH: 21
<212> TYPE: DNA
<213> ORGANISM: Artificial Sequence
```

```
<220> FEATURE:
<223> OTHER INFORMATION: Synthetic Oligomeric Compound

<400> SEQUENCE: 334
ttgtctaacc agtcacctgt t                                              21

<210> SEQ ID NO 335
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 335
aaaacaaaat ctcaccgttt t                                              21

<210> SEQ ID NO 336
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 336
actggctgag tcaggactag c                                              21

<210> SEQ ID NO 337
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 337
atcagaggtt cagcttaccc t                                              21

<210> SEQ ID NO 338
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 338
catattacaa tgagctcatc                                                20

<210> SEQ ID NO 339
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 339
agacaaggcc cacccgtgca aac                                            23

<210> SEQ ID NO 340
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 340
attttggtac agcagctca                                                 19
```

```
<210> SEQ ID NO 341
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 341
ttttggtgca tatttacttt a                                              21

<210> SEQ ID NO 342
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 342
ggcggccggc cggcgcacgc                                                20

<210> SEQ ID NO 343
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 343
acttcaagga tcttaaactt tg                                             22

<210> SEQ ID NO 344
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 344
gcaaatggta cagctacttt                                                20

<210> SEQ ID NO 345
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 345
gggaaacgta tgtcaacct                                                 19

<210> SEQ ID NO 346
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 346
gcctgctgac accgtgcct                                                 19

<210> SEQ ID NO 347
<211> LENGTH: 22
<212> TYPE: DNA
<213> ORGANISM: Artificial Sequence
<220> FEATURE:
<223> OTHER INFORMATION: Synthetic Oligomeric Compound
```

<400> SEQUENCE: 347
aaacagacat cgcgagccag cc                                              22

<210> SEQ ID NO 348
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 348
gttgggatca caggcgccc                                                  19

<210> SEQ ID NO 349
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 349
gttctgtcct ggaagaacat act                                             23

<210> SEQ ID NO 350
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 350
gtgtgtatac atttatacat                                                 20

<210> SEQ ID NO 351
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 351
actttccagg attcattaac t                                               21

<210> SEQ ID NO 352
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 352
tgcaaaggta attgctgttt tc                                              22

<210> SEQ ID NO 353
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 353
ctcactcaga tggccaactc a                                               21

<210> SEQ ID NO 354

```
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 354
tgggccaccg ccgagcggac                                         20

<210> SEQ ID NO 355
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 355
ctgatcagtt acacatcact tcag                                    24

<210> SEQ ID NO 356
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 356
gtgggtgtgt gcatgagcgt g                                       21

<210> SEQ ID NO 357
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 357
gctcctgtcc aactggctc                                          19

<210> SEQ ID NO 358
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 358
caaagacgtg gagaaattag aat                                     23

<210> SEQ ID NO 359
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 359
caggtaccaa tattttatct a                                       21

<210> SEQ ID NO 360
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 360
```
acaatcctag agcacaagaa g                          21

<210> SEQ ID NO 361
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 361
atcgcggttt ataccaaatg aat                        23

<210> SEQ ID NO 362
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 362
cctaatgatt catcattctc aa                         22

<210> SEQ ID NO 363
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 363
actgatctag agaacacaag a                          21

<210> SEQ ID NO 364
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 364
agtaactggt tgaacaactg taa                        23

<210> SEQ ID NO 365
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 365
gtaatgggac cttcctctttt g                         21

<210> SEQ ID NO 366
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 366
ctcagtccca ggcaaaccat aa                         22

<210> SEQ ID NO 367
<211> LENGTH: 19
<212> TYPE: DNA

```
<213> ORGANISM: Artificial Sequence
<220> FEATURE:
<223> OTHER INFORMATION: Synthetic Oligomeric Compound

<400> SEQUENCE: 367
tagcatacag atacgccca                                               19

<210> SEQ ID NO 368
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 368
ggacctaaaa atacaatgca ta                                           22

<210> SEQ ID NO 369
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 369
gtgactcatc acctatggaa a                                            21

<210> SEQ ID NO 370
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 370
gttctaaccc attgtggcca a                                            21

<210> SEQ ID NO 371
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 371
tctgggaacc ggcatttgtt ctga                                         24

<210> SEQ ID NO 372
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 372
ctgcactttt atgaataagc tc                                           22

<210> SEQ ID NO 373
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 373
acaatgagaa cccatggtct                                              20
```

<210> SEQ ID NO 374
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 374
acatcatcgc atattgacac aa                                           22

<210> SEQ ID NO 375
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 375
gctgagcaat gcctggctgg tgcct                                        25

<210> SEQ ID NO 376
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 376
aaagtcacag gccaccccag atggg                                        25

<210> SEQ ID NO 377
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 377
agacacacca cggcacactt c                                            21

<210> SEQ ID NO 378
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 378
cccgaggagc cgggcaggct t                                            21

<210> SEQ ID NO 379
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 379
acagtggtca tcgagtgaca ca                                           22

<210> SEQ ID NO 380
<211> LENGTH: 22
<212> TYPE: DNA
<213> ORGANISM: Artificial Sequence
<220> FEATURE:

<223> OTHER INFORMATION: Synthetic Oligomeric Compound

<400> SEQUENCE: 380
tgacgatgac aacgatgacg ta                                              22

<210> SEQ ID NO 381
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 381
gtttgataaa ctgacacaac                                                 20

<210> SEQ ID NO 382
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 382
gagcaaggct cttgtctgta agt                                             23

<210> SEQ ID NO 383
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 383
ctcctccaac aatcctagac ca                                              22

<210> SEQ ID NO 384
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 384
gggccgcagc tgtcgcccgt gtc                                             23

<210> SEQ ID NO 385
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 385
gcaaaagtaa ttgcagtgtg tg                                              22

<210> SEQ ID NO 386
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 386
gtcctgaatt ccgcagcct                                                  19

```
<210> SEQ ID NO 387
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 387
aggagaaggc accatgggat tta                                          23

<210> SEQ ID NO 388
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 388
atctttgatt ttcagtagtt t                                            21

<210> SEQ ID NO 389
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 389
gttatagatc tggatttgaa c                                            21

<210> SEQ ID NO 390
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 390
acggagctgt cccaacacca cccct                                        25

<210> SEQ ID NO 391
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 391
agagatgaga gaaacaccct                                              20

<210> SEQ ID NO 392
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 392
tcccagcaca catttagctc a                                            21

<210> SEQ ID NO 393
<211> LENGTH: 23
<212> TYPE: DNA
<213> ORGANISM: Artificial Sequence
<220> FEATURE:
<223> OTHER INFORMATION: Synthetic Oligomeric Compound
```

```
<400> SEQUENCE: 393
gtcagacccc gagggtcct cgc                                      23

<210> SEQ ID NO 394
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 394
aaggagctca gaagccctgc ccagc                                   25

<210> SEQ ID NO 395
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 395
ggcaaagaag gaacattcct                                         20

<210> SEQ ID NO 396
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 396
ccacctggca agaacaggcg ttc                                     23

<210> SEQ ID NO 397
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 397
agagggagac ccaggctcgg a                                       21

<210> SEQ ID NO 398
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 398
aagtcactga agggttttga gt                                      22

<210> SEQ ID NO 399
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 399
gccaccttca aatgggaagt ct                                      22

<210> SEQ ID NO 400
<211> LENGTH: 23
```

-continued

```
<212> TYPE: DNA
<213> ORGANISM: Artificial Sequence
<220> FEATURE:
<223> OTHER INFORMATION: Synthetic Oligomeric Compound

<400> SEQUENCE: 400
actcagaagg acaagtagag ttt                                              23

<210> SEQ ID NO 401
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 401
actgggcaca aacatgtcca ggtc                                             24

<210> SEQ ID NO 402
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 402
atttctatat ctatctccat                                                  20

<210> SEQ ID NO 403
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 403
aggtaagcgc tgttgctagc c                                                21

<210> SEQ ID NO 404
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 404
gctccaacct cagcagactg t                                                21

<210> SEQ ID NO 405
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 405
acccaacagc ccctgcaagg gat                                              23

<210> SEQ ID NO 406
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 406
```

```
tgaacacaag gtactggtac ta                                              22

<210> SEQ ID NO 407
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 407
aggactatag aactttcccc ct                                              22

<210> SEQ ID NO 408
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 408
aagacatttt cagacagct                                                  19

<210> SEQ ID NO 409
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 409
tcctcttttc ttagagactc ac                                              22

<210> SEQ ID NO 410
<211> LENGTH: 20
<212> TYPE: DNA
<213> ORGANISM: Artificial Sequence
<220> FEATURE:
<223> OTHER INFORMATION: Synthetic Oligomeric Compound

<400> SEQUENCE: 410
cgactgccac tcttactaga                                                 20

<210> SEQ ID NO 411
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 411
gctgggctta cgttgggaga ac                                              22

<210> SEQ ID NO 412
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 412
accttccctg gtacagaata ct                                              22

<210> SEQ ID NO 413
<211> LENGTH: 21
<212> TYPE: DNA
<213> ORGANISM: Artificial Sequence
```

```
<220> FEATURE:
<223> OTHER INFORMATION: Synthetic Oligomeric Compound

<400> SEQUENCE: 413
gctgaggtct gggccaggtc t                                              21

<210> SEQ ID NO 414
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 414
tcccacagga agcagacac                                                 19

<210> SEQ ID NO 415
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 415
tttattgtgg tagatactat tag                                            23

<210> SEQ ID NO 416
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 416
gtccaaagtt ggggtgctgg tt                                             22

<210> SEQ ID NO 417
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 417
ggacattgtt tcagtgccca agt                                            23

<210> SEQ ID NO 418
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 418
ctgcgggcgg gacgagcaag caca                                           24

<210> SEQ ID NO 419
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 419
acgcagagcc cgaaagcccc cagt                                           24
```

<210> SEQ ID NO 420
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 420
aggccgccac ccgcccgcga tccct                               25

<210> SEQ ID NO 421
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 421
acagcgctcg caaccgcagc gat                                 23

<210> SEQ ID NO 422
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 422
agaggcaggt tcctggatca t                                   21

<210> SEQ ID NO 423
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 423
gaggtgactc tatcctatgt cttt                                24

<210> SEQ ID NO 424
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 424
caagacacat ttggagaggg ac                                  22

<210> SEQ ID NO 425
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 425
ctacctgagc tagcatacaa gt                                  22

<210> SEQ ID NO 426
<211> LENGTH: 19
<212> TYPE: DNA
<213> ORGANISM: Artificial Sequence
<220> FEATURE:
<223> OTHER INFORMATION: Synthetic Oligomeric Compound

```
<400> SEQUENCE: 426
gctctaagaa agccacact                                                19

<210> SEQ ID NO 427
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 427
tcagcagtac cagcctaga                                                19

<210> SEQ ID NO 428
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 428
gcctcagagg cagctgctt                                                19

<210> SEQ ID NO 429
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 429
gaaggaagtg agtgcagcca c                                             21

<210> SEQ ID NO 430
<211> LENGTH: 19
<212> TYPE: DNA
<213> ORGANISM: Artificial Sequence
<220> FEATURE:
<223> OTHER INFORMATION: Synthetic Oligomeric Compound

<400> SEQUENCE: 430
accagtgccc tgcacactt                                                19

<210> SEQ ID NO 431
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 431
gactcttgaa caacacaggt tt                                            22

<210> SEQ ID NO 432
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 432
gtcctgagag cgctgcctcc t                                             21

<210> SEQ ID NO 433
```

```
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 433
caaaagtcaa gcttatccta aa                                          22

<210> SEQ ID NO 434
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 434
tgcacaaccc tagtggcgcc att                                         23

<210> SEQ ID NO 435
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 435
gttcagtaga gattgtttca a                                           21

<210> SEQ ID NO 436
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 436
gcacatgttc tgcggcccac ca                                          22

<210> SEQ ID NO 437
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 437
aaagaggtta accatgtatt at                                          22

<210> SEQ ID NO 438
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 438
agaggttgac tgtataatat t                                           21

<210> SEQ ID NO 439
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 439
```

```
cctagagagg gtgagaacct gcc                                             23

<210> SEQ ID NO 440
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 440
accaacggac ctacttccct ccgcc                                           25

<210> SEQ ID NO 441
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 441
tggggaccct ccctgaacca ag                                              22

<210> SEQ ID NO 442
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 442
caactccgat atgcaatggg ta                                              22

<210> SEQ ID NO 443
<211> LENGTH: 24
<212> TYPE: DNA
<213> ORGANISM: Artificial Sequence
<220> FEATURE:
<223> OTHER INFORMATION: Synthetic Oligomeric Compound

<400> SEQUENCE: 443
acgcgcaggc cagagaccca ggca                                            24

<210> SEQ ID NO 444
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 444
ctgctgggcc acaacgtggg a                                               21

<210> SEQ ID NO 445
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 445
gcggtcccgc ggcgccccgc ct                                              22

<210> SEQ ID NO 446
<211> LENGTH: 23
<212> TYPE: DNA
```

```
<213> ORGANISM: Artificial Sequence
<220> FEATURE:
<223> OTHER INFORMATION: Synthetic Oligomeric Compound

<400> SEQUENCE: 446
gtagtgggcc gagccgagtg aca                                          23

<210> SEQ ID NO 447
<211> LENGTH: 25
<212> TYPE: DNA
<213> ORGANISM: Artificial Sequence
<220> FEATURE:
<223> OTHER INFORMATION: Synthetic Oligomeric Compound

<400> SEQUENCE: 447
acctccagcc cctccagggc ttcct                                        25

<210> SEQ ID NO 448
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 448
caacaaaatc actagtcttc ca                                           22

<210> SEQ ID NO 449
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 449
ggttagtgga ccaggtcaca aa                                           22

<210> SEQ ID NO 450
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 450
catcaccttc cttctcctcc a                                            21

<210> SEQ ID NO 451
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 451
gctgaggctg tggggctgga gt                                           22

<210> SEQ ID NO 452
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 452
agaaaccatg gggtatgagc aga                                          23
```

<210> SEQ ID NO 453
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 453
catgctcaga caaccatggt gca                                          23

<210> SEQ ID NO 454
<211> LENGTH: 28
<212> TYPE: DNA
<213> ORGANISM: Artificial Sequence
<220> FEATURE:
<223> OTHER INFORMATION: Synthetic Oligomeric Compound

<400> SEQUENCE: 454
gtcagcagtt tgagtgtcag cattgtga                                     28

<210> SEQ ID NO 455
<211> LENGTH: 26
<212> TYPE: DNA
<213> ORGANISM: Artificial Sequence
<220> FEATURE:
<223> OTHER INFORMATION: Synthetic Oligomeric Compound

<400> SEQUENCE: 455
atcactccgt actttcatcc tccaac                                       26

<210> SEQ ID NO 456
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 456
aaccaagacc ccggagatcc cag                                          23

<210> SEQ ID NO 457
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 457
agctcagaac ccagaggtct ca                                           22

<210> SEQ ID NO 458
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 458
tggccctgac acgtggtact gga                                          23

<210> SEQ ID NO 459
<211> LENGTH: 24
<212> TYPE: DNA
<213> ORGANISM: Artificial Sequence
<220> FEATURE:

<223> OTHER INFORMATION: Synthetic Oligomeric Compound

<400> SEQUENCE: 459
gtcgattccg cacgcagagc aatc                                              24

<210> SEQ ID NO 460
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 460
acaaggatga atctttgtta ctg                                               23

<210> SEQ ID NO 461
<211> LENGTH: 23
<212> TYPE: DNA
<213> ORGANISM: Artificial Sequence
<220> FEATURE:
<223> OTHER INFORMATION: Synthetic Oligomeric Compound

<400> SEQUENCE: 461
tcatacagct agataaccaa aga                                               23

<210> SEQ ID NO 462
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 462
actttcggtt atctagcttt a                                                 21

<210> SEQ ID NO 463
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 463
caggccggga caagtgcaat a                                                 21

<210> SEQ ID NO 464
<211> LENGTH: 21
<212> TYPE: DNA
<213> ORGANISM: Artificial Sequence
<220> FEATURE:
<223> OTHER INFORMATION: Synthetic Oligomeric Compound

<400> SEQUENCE: 464
gaggccggga cgagtgcaat a                                                 21

<210> SEQ ID NO 465
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 465
ctacctgcac gaacagcact tt                                                22

```
<210> SEQ ID NO 466
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 466
tgctcaataa atacccgttg aa                                              22

<210> SEQ ID NO 467
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 467
gcaaaaatgt gctagtgcca aa                                              22

<210> SEQ ID NO 468
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 468
aacaatacaa cttactacct ca                                              22

<210> SEQ ID NO 469
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 469
cacaagatcg gatctacggg tt                                              22

<210> SEQ ID NO 470
<211> LENGTH: 22
<212> TYPE: DNA
<213> ORGANISM: Artificial Sequence
<220> FEATURE:
<223> OTHER INFORMATION: Synthetic Oligomeric Compound

<400> SEQUENCE: 470
cgcaaggtcg gttctacggg tg                                              22
```